United States Patent
Jung et al.

(10) Patent No.: US 10,214,593 B2
(45) Date of Patent: Feb. 26, 2019

(54) ANTI-IDIOTYPE ANTIBODY AGAINST ANTI-C-MET ANTIBODY

(71) Applicant: SAMSUNG ELECTRONICS CO., LTD., Suwon-si, Gyeonggi-do (KR)

(72) Inventors: Soo Yeon Jung, Seongnam-si (KR); Yun Jeong Song, Seongnam-si (KR); Mi Young Cho, Seoul (KR); Han Na Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 903 days.

(21) Appl. No.: 14/243,751

(22) Filed: Apr. 2, 2014

(65) Prior Publication Data

US 2014/0302517 A1    Oct. 9, 2014

(30) Foreign Application Priority Data

Apr. 2, 2013 (KR) .................. 10-2013-0036053
Mar. 31, 2014 (KR) .................. 10-2014-0037574

(51) Int. Cl.
| | | |
|---|---|---|
| *G01N 33/53* | (2006.01) | |
| *C07K 16/32* | (2006.01) | |
| *C07K 16/42* | (2006.01) | |
| *G01N 33/68* | (2006.01) | |
| *C07K 16/28* | (2006.01) | |

(52) U.S. Cl.
CPC ..... *C07K 16/4258* (2013.01); *G01N 33/6806* (2013.01); *G01N 33/686* (2013.01); *C07K 16/2863* (2013.01); *C07K 2317/24* (2013.01); *C07K 2317/53* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,041,288 B2 | 5/2006 | Kricek et al. |
| 7,892,550 B2 | 2/2011 | Dennis et al. |
| 8,563,696 B2 | 10/2013 | Cheong et al. |
| 2007/0092520 A1 | 4/2007 | Dennis et al. |
| 2008/0118939 A1 | 5/2008 | Stubenrauch et al. |
| 2011/0104176 A1 | 5/2011 | Cheong et al. |
| 2011/0110642 A1 | 5/2011 | Salomons et al. |
| 2012/0149031 A1 | 6/2012 | Goetsch et al. |
| 2012/0156206 A1 | 6/2012 | Hultberg et al. |

FOREIGN PATENT DOCUMENTS

| | | |
|---|---|---|
| EP | 2 316 484 A1 | 5/2011 |
| KR | 10-20110047698 A | 5/2011 |
| WO | 2011/110642 A2 | 9/2011 |
| WO | WO 2012/030982 A1 | 3/2012 |

OTHER PUBLICATIONS

Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Lamminmaki et al. (JBC 2001, 276:36687-36694).*
Padlan et al. (PNAS 1989, 86:5938-5942).*
Lloyd et al. Protein Engineering, Design & Selection 2009, 22:159-168.*
European Search Report for Application No. 14162847.9 dated Jul. 28, 2014.
Oh et al., "A new anti-c-Met Antibody Selected by a Mechanism-Based Dual-Screening Method:Therapeutic Potential in Cancer," *Molecules and Cells*, 34 (6): 523-529 (2012).
Pacchiana et al., "Monovalency Unleashes the Full Therapeutic Potential of the DN-30 Anti-Met Antibody," *Journal of Biological Chemistry*, 285 (46): 36149-36157 (2010).
European Office Action for Application No. 14162847.9 dated Oct. 11, 2016.

* cited by examiner

*Primary Examiner* — Sharon X Wen
(74) *Attorney, Agent, or Firm* — Leydig, Voit & Mayer, Ltd.

(57) ABSTRACT

Disclosed are an anti-idiotype antibody that specifically binds to an idiotope site of an anti-c-Met antibody, the use of the anti-idiotype antibody for detecting the anti-c-Met antibody, and methods, polypeptides, polynucleotides, compositions, and vaccines related thereto.

9 Claims, 8 Drawing Sheets

Specification includes a Sequence Listing.

ANTI-IDIOTYPE ANTIBODY AGAINST ANTI-C-MET ANTIBODY

CROSS-REFERENCE TO RELATED APPLICATIONS

This application claims the benefits of Korean Patent Application No. 10-2013-0036053 filed on Apr. 2, 2013 in the Korean Intellectual Property Office, and Korean Patent Application No. 10-2014-0037574 filed on Mar. 31, 2014 in the Korean Intellectual Property Office, the entire disclosures of which are hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 234,710 byte ASCII (Text) file named "715886_ST25.TXT" created on Sep. 26, 2018.

BACKGROUND

1. Field

Provided are anti-idiotype antibodies, polypeptides, compositions, vaccines and polynucleotides useful for the analysis, binding, and detection of anti-c-Met antibodies. Additionally, methods of detection and characterization of anti-c-Met antibodies are also provided.

2. Description of the Related Art

In antibody therapy, it is essential to measure the half-life of a therapeutic antibody and an effective concentration thereof after it is administered into body Thus, a technique capable of measuring the amount of an antibody remaining in the body is necessary. When an antibody which functions at the fragment crystallizable (Fc) portion or fragment antigen-binding (Fab) portion of the antibody is used for such a measurement, a polyclonal antibody specific to human immunoglobulin G (IgG) is generally used. If a human serum or a monkey serum is to be analyzed using a polyclonal antibody specific to human IgG, the polyclonal antibody has a limitation in its application and may show high background, thereby causing a decrease in accuracy. Additionally there exist methods of measuring the amount of a remaining antibody using an antigen as a capture, but concerns of probability of missing antigen-antibody complex and causing change in antigen-antibody binding affinity due to a conformational change of the antigen have arisen. Therefore, there is a need for the development of an antibody having specificity against an antibody which needs to be detected.

SUMMARY

Provided is an anti-idiotype antibody, wherein the anti-idiotype antibody specifically binds to an idiotope site of an anti-c-Met antibody.

Additionally, provided are compositions for detecting an anti-c-Met antibody. Related antigen binding fragments, vaccines, polypeptides, polynucleotides, and methods are also provided.

DETAILED DESCRIPTION

Figure 1:
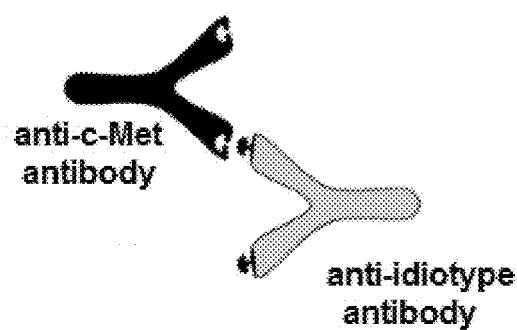
FIG. 1 is a schematic illustrating the interaction between an anti-c-Met antibody and anti-idiotype antibodies according to embodiments of the present invention.

Reference will now be made in detail to embodiments, examples of which are illustrated in the accompanying drawings, wherein like reference numerals refer to like elements throughout. In this regard the present embodiments may have different forms and should not be construed as being limited to the descriptions set forth herein. Accordingly, the embodiments are merely described below, by referring to the figures, to explain aspects of the present description.

An anti-idiotype antibody against an anti-c-Met antibody or antigen-binding fragment (i.e., an antibody or antigen-binding fragment thereof that specifically binds to an idiotope of an anti-c-Met antibody) and uses thereof are provided.

In order to monitor treatment progress during the treatment of c-Met related diseases using an anti-c-Met antibody, a technique for measuring the in vivo state (half-life of antibody, effective concentration, targeting degree, etc.) of the anti-c-Met antibody after the administration thereof into the living body is needed. An anti-idiotype antibody that specifically binds to an idiotope site of an anti-c-Met antibody enables one to measure in vivo state of the anti-c-Met antibody in a simple and accurate way.

In addition, as all therapeutic proteins, including therapeutic antibodies are substances having a potential antigenicity, they all have the possibility of causing an immune response when administered into the body. Once an antibody specific for the therapeutic protein administered into the body (anti-drug antibody; ADA) is generated, there is a high possibility that an antibody-drug (therapeutic protein) complex is formed, and that the drug efficacy of the therapeutic protein is diminished and side effects are caused. Hence, it is very important to monitor and measure any production of such an anti-drug antibody in subjects undergoing treatment with therapeutic proteins, as such an antibody can disrupt the stability and drug efficacy of a therapeutic regimen. Generally, an antibody drug is used to capture and/or a detect molecules of interest (e.g., an antigen), wherein it is possible to utilize an anti-idiotype antibody as a positive control for the quantification of the antibody drug or a basis for quantification.

In order to address problems associated with anti-drug antibodies, provided is an anti-idiotype antibody capable of specifically binding an idiotope site of an anti-c-Met antibody useful for the detection and/or the quantification of an anti-drug antibody.

In another embodiment, there is provided a method for detecting an anti-c-Met antibody present in a clinical sample using anti-idiotype antibodies.

In another embodiment, there is provided a method for the quantitative analysis of an anti-drug antibody using anti-idiotype antibody.

In some embodiments, the variable region (e.g., CDRs) of the anti-idieotypic antibody has a binding site that is structurally similar to a portion of an antigen of the subject antibody. Accordingly, when the subject antibody is an antibody for the treatment of a particular disease, the anti-idiotype antibody thereof may be used as a vaccine capable of inducing an immune response by replacing the antigen which is a protein that causes the disease.

Accordingly, in another embodiment, there is provided a vaccine composition for c-Met related diseases including the anti-idiotype antibody against a anti-c-Met antibody.

Hereafter, the present invention will be described in more detail.

Figure 7:
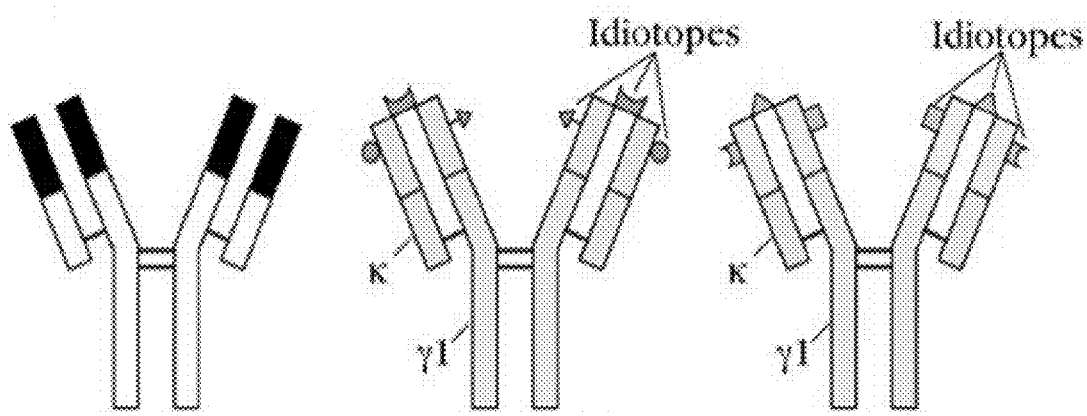
FIG. 7 is a schematic illustrating the location of potential binding sites of an anti-idiotype antibody.

In the leftmost drawing of FIG. 7, anti-c-Met antibody portions shaded in black, which are the variable regions of the antibody that determine antibody specificity, serve as antigenic determinants (i.e., epitopes) with respect to the anti-idiotypic antibody. Within these sites, there exist idiotope sites (see the center and right drawings of FIG. 7) which are individual binding sites for the anti-idiotypic antibody. These portions can distinguish one anti-idiotypic antibody from another antibody (e.g., different anti-idiotypic antibodies can be specific for different idiotopes). Thus, anti-c-Met antibodies, in spite of being capable of reacting with the same antigen, may have different idiotopes from each other, depending on their antigen-binding sites. Accordingly, an anti-idiotypic antibody targeted at such idiotope sites (i.e., specifically recognizing and/or binding to the idiotope sites), may acquire antibody specificity.

The anti-idiotype antibody is an antibody capable of recognizing the idiotopes of a c-Met antibody, which refers to an antibody specifically targeted at the idiotopes of the anti-c-Met antibody, or specifically binding to the idiotopes of the anti-c-Met antibody. The idiotopes of the anti-c-Met antibody may be complementarity determining regions (CDR) of the anti-c-Met antibody, variable regions of the anti-c-Met antibody, or partial portions of the variable regions of the anti-c-Met antibody. The CDR may be one or more selected from the group consisting of CDR-H1, CDR-H2, CDR-H3, CDR-L1, CDR-L2, and CDR-L3. The variable regions of the anti-c-Met antibody may be heavy chain variable regions including one or more selected from the group consisting of CDR-H1, CDR-H2, and CDR-H3, light chain variable regions including one or more selected from the group consisting of CDR-L1, CDR-L2, and CDR-L3, or a combination of the heavy chain variable regions and the light chain variable regions. The partial fragments of the heavy chain variable regions and the light chain variable regions of the anti-c-Met antibody may be fragments including 2 or more, 5 or more, or 10 or more contiguous amino acids, for example, from about 2 to about 100, from about 5 to about 100, from about 10 to about 100, from about 2 to about 50, from about 5 to about 50, or from about 10 to about 50 contiguous amino acids within the heavy chain variable regions or the light chain variable regions of the anti-c-Met antibody. The partial fragments of the heavy chain variable regions and the light chain variable regions of the anti-c-Met antibody may be fragments including 2 or more, 5 or more, or 10 or more contiguous amino acids, for example, from about 2 to about 100, from about 5 to about 100, from about 10 to about 100, from about 2 to about 50, from about 5 to about 50, or from about 10 to about 50 contiguous amino acids within the variable regions containing one or more CDR or CDR fragments. The CDR fragments may be consecutive or non-consecutive 2 or more, or 5 or more amino acids within the CDR. Therefore, the idiotopes of the anti-c-Met antibody may be from about 2 to about 100, from about 5 to about 100, from about 10 to about 100, from about 2 to about 50, from about 5 to about 50, or from about 10 to about 50 contiguous amino acids containing one or more CDR or one or more CDR fragments within the heavy chain variable regions or the light chain variable regions of the anti-c-Met antibody. In another embodiment, the idiotopes may be a single amino acid which is located at the variable regions of the anti-c-Met antibody, for example, CDR sites.

As used herein, the phrase "contiguous amino acids" may refer to contiguous amino acid residues on the primary, secondary, or tertiary structure of a protein, wherein the contiguous amino acid residues on the secondary or tertiary structure of a protein may be consecutive or non-consecutive on the primary structure (amino acid sequence) of a protein.

In one embodiment, the anti c-Met antibody may be any antibody or antigen-binding fragment that acts on c-Met to induce c-Met intracellular internalization and degradation. The anti c-Met antibody be any antibody capable of recognizing a specific region of c-Met, e.g., a specific region in the SEMA domain, as an epitope.

"c-Met" or "c-Met protein" refers to a receptor tyrosine kinase (RTK) which binds hepatocyte growth factor (HGF). c-Met may be derived from any species, particularly a mammal, for instance, primates such as human c-Met (e.g., NP_000236), monkey c-Met (e.g., Macaca mulatta, NP_001162100), or rodents such as mouse c-Met (e.g., NP_032617.2), rat c-Met (e.g., NP_113705.1), and the like. The c-Met protein may include a polypeptide encoded by the nucleotide sequence identified as GenBank Accession Number NM_000245, a polypeptide having the amino acid sequence identified as GenBank Accession Number NP_000236 or extracellular domains thereof. The receptor tyrosine kinase c-Met participates in various mechanisms, such as cancer incidence, metastasis, migration of cancer cell, invasion of cancer cell, angiogenesis, and the like.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin identity/homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79), is a loop region between the second and the third propellers within the epitopes of the SEMA domain. This region acts as an epitope for the anti c-Met antibody provided in the present invention.

The term "epitope," as used herein, refers to an antigenic determinant, a part of an antigen recognized by an antibody. In one embodiment, the epitope may be a region comprising 5 or more contiguous amino acid residues within the SEMA domain (SEQ ID NO: 79) of c-Met protein, for instance, 5 to 19 consecutive amino acid residues within the amino acid sequence of SEQ ID NO: 71. For example, the epitope may be a polypeptide including 5 to 19 contiguous amino acids selected from among partial combinations of the amino acid sequence of SEQ ID NO: 71, wherein the polypeptide includes the amino sequence of SEQ ID NO: 73 (EEPSQ) serving as an essential element for the epitope. For example, the epitope may be a polypeptide comprising, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

Thus, the anti c-Met antibody may specifically bind to an epitope which has from about 5 to about 19 contiguous amino acids selected from among partial combinations of the amino acid sequence of SEQ ID NO: 71, including SEQ ID NO: 73 as an essential element. For example, the anti c-Met antibody may specifically bind to an epitope including the amino acid sequence of SEQ ID NO: 71, SEQ ID NO: 72, or SEQ ID NO: 73.

In one embodiment, the anti c-Met antibody or an antigen-binding fragment thereof may include:

at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence including 8-19 consecutive amino acids within SEQ ID NO: 2 including amino acid residues from the $3^{rd}$ to $10^{th}$ positions of SEQ ID NO: 2; and (c) a CDR-H3 including the amino acid sequence of SEQ ID NO: 6, SEQ ID NO: 85, or an amino acid sequence including 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 86, or an amino acid sequence including 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

$Xaa_1$-$Xaa_2$-Tyr-Tyr-Met-Ser (SEQ ID NO: 4),   Formula I wherein $Xaa_1$ is absent or Pro or Ser, and $Xaa_2$ is Glu or Asp, Arg-Asn-$Xaa_3$-$Xaa_4$-Asn-Gly-$Xaa_5$-Thr (SEQ ID NO: 5),   Formula II wherein $Xaa_3$ is Asn or Lys, $Xaa_4$ is Ala or Val, and $Xaa_5$ is Asn or Thr, Asp-Asn-Trp-Leu-$Xaa_6$-Tyr (SEQ ID NO: 6),   Formula III wherein $Xaa_6$ is Ser or Thr, Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala (SEQ ID NO: 7)   Formula IV wherein $Xaa_7$ is His, Arg, Gln, or Lys, $Xaa_8$ is Ser or Trp, $Xaa_9$ is His or Gln, and $Xaa_{10}$ is Lys or Asn, Trp-$Xaa_{11}$-Ser-$Xaa_{12}$-Arg-Val-$Xaa_{13}$ (SEQ ID NO: 8)   Formula V wherein $Xaa_{11}$ is Ala or Gly, $Xaa_{12}$ is Thr or Lys, and $Xaa_{13}$ is Ser or Pro, and $Xaa_{14}$-Gln-Ser-Tyr-Ser-$Xaa_{15}$-Pro-$Xaa_{16}$-Thr (SEQ ID NO: 9)   Formula VI wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may have an amino acid sequence selected from the group consisting of SEQ ID NOS: 1, 22, 23, and 24. The CDR-H2 may have an amino acid sequence selected from the group consisting of SEQ ID NOS: 2, 25, and 26. The CDR-H3 may have an amino acid sequence selected from the group consisting of SEQ ID NOS: 3, 27, 28, and 85.

The CDR-L1 may have an amino acid sequence selected from the group consisting of SEQ ID NOS: 10, 29, 30, 31, 32, 33, and 106. The CDR-L2 may have an amino acid sequence selected from the group consisting of SEQ ID NOS: 11, 34, 35, and 36. The CDR-L3 may have an amino acid sequence selected from the group consisting of SEQ ID NOS: 12, 13, 14, 15, 16, 37, 86, and 89.

In another embodiment, the anti-c-Met antibody or antigen-binding fragment may include a heavy variable region comprising a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85; and a light variable region comprising a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89.

In one specific embodiment of the anti c-Met antibody or antigen-binding fragment, the variable domain of the heavy chain has the amino acid sequence of SEQ ID NO: 17, 74, 87, 90, 91, 92, 93, or 94 and the variable domain of the light chain has the amino acid sequence of SEQ ID NO: 18, 19, 20, 21, 75, 88, 95, 96, 97, 98, 99, or 107.

Animal-derived anti c-Met antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen-binding in variable regions of chimeric antibodies into a human antibody framework.

The most important aspect of CDR grafting to produce humanized anti c-Met antibodies is choosing the optimized human antibodies for accepting CDRs of animal-derived antibodies. Antibody databases, analysis of antibody crystal structures, and technology for molecule modeling are used. However, even when the CDRs of animal-derived antibodies are grafted to the most optimized human antibody framework, amino acids positioned in a framework of the animal-derived CDRs affecting antigen-binding are present. Therefore, in many cases, antigen-binding affinity is not maintained, and thus application of additional antibody engineering technology for recovering the antigen-binding affinity is necessary.

The anti c-Met antibodies may be a mouse-derived antibody, a mouse-human chimeric antibody, a humanized antibody, or a human antibody. The antibodies or antigen-binding fragments thereof may be isolated from (that is, not originally present in) a living body or non-naturally occurring. The antibodies or antigen-binding fragments may be recombinant or synthetic.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma ($\gamma$), mu ($\mu$), alpha ($\alpha$), delta ($\delta$), or epsilon ($\epsilon$) type, which may be further categorized as gamma 1 ($\gamma$1), gamma 2($\gamma$2), gamma 3($\gamma$3), gamma 4($\gamma$4), alpha 1($\alpha$1), or alpha 2($\alpha$2). The light chain constant region is of either a kappa ($\kappa$) or lambda ($\lambda$) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In a particular embodiment, the antigen-binding fragment may be scFv, (scFv)$_2$, scFvFc, Fab, Fab', or F(ab')$_2$, but is not limited thereto.

Among the antigen-binding fragments, Fab includes light chain and heavy chain variable regions, a light chain constant region, and a first heavy chain constant region $C_{H1}$, and has one antigen-binding site.

The Fab' fragment differs from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be the same as described in the above, for example, those having the amino acid length of 1 to 100, 2 to 50, particularly 5 to 25, and any kinds of amino acids may be included without any restrictions.

The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen-binding efficiency of the humanized antibody. The modification of the hinge region through amino acid deletion, addition, or substitution is well-known to those skilled in the art.

In one embodiment, the anti-c-Met antibody or antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100(U7-HC6), 101(U6-HC7), 102(U3-HC9), 103(U6-HC8), or 104(U8-HC5), or a hinge region including the amino acid sequence of SEQ ID NO: 105 (non-modified human hinge). In particular, the hinge region has the amino acid sequence of SEQ ID NO: 100 or 101.

In one embodiment, the anti c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include all the antibodies defined in Korean Patent Publication No. 2011-0047698.

In the anti-c-Met antibody, the remaining portion of the light chain and the heavy chain, excluding the CDRs, the light chain variable region, and the heavy chain variable region as defined above, that is the light chain constant region and the heavy chain constant region, may be those from any subtype of immunoglobulin (e.g., IgG1, IgG2, and the like).

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 108.

The polypeptide of SEQ ID NO: 70 is a light chain including human kappa (K) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

In another embodiment, the anti c-Met antibody may include a light chain complementarity determining region including the amino acid sequence of SEQ ID NO: 106, a light chain variable region including the amino acid sequence of SEQ ID NO: 107, or a light chain including the amino acid sequence of SEQ ID NO: 108.

In one particular embodiment, the anti-idiotype antibody that specifically binds to an idiotope site of an anti-c-Met antibody may include at least one heavy chain complementarity determining region (CDR) selected from the group consisting of CDR-H1 containing the amino acid sequence of SEQ ID NO: 109 or SEQ ID NO: 110, CDR-H2 containing the amino acid sequence of SEQ ID NO: 111 or SEQ ID NO: 138, and CDR-H3 containing an amino acid sequence selected from the group consisting of SEQ ID NO: 139 to SEQ ID NO: 154, or a heavy chain variable region including the at least one heavy chain complementarity determining region;

at least one light chain complementarity determining region selected from the group consisting of CDR-L1 containing the amino acid sequence of SEQ ID NO: 112 or an the amino acid sequence selected from the group consisting of SEQ ID NO: 166 to SEQ ID NO: 171, CDR-L2 containing the amino acid sequence of SEQ ID NO: 113 or SEQ ID NO: 187, and CDR-L3 containing the amino acid sequence of SEQ ID NO: 114 or an amino acid sequence selected from the group consisting of SEQ ID NO: 198 to SEQ ID NO: 201, or a light chain variable region including the at least one light chain complementarity determining region;

a combination of the at least one heavy chain complementarity determining region and the at least one light chain complementarity determining region; or a combination of the heavy chain variable region and the light chain variable region.

SEQ ID NO: 109 is a sequence of the general formula: X1-Y-X2-M-S (SEQ ID NO: 109),
wherein X1 is aspartic acid (D), asparagine (N), or glycine (G), and
X2 is tyrosine (Y), alanine (A), aspartic acid (D), or serine (S);

SEQ ID NO: 110 is a sequence of the general formula: S-Y-X3-X4-X5 (SEQ ID NO: 110),
wherein X3 is alanine (A) or glycine (G),
X4 is methionine (M) or isoleucine (I), and
X5 is serine (S) or histidine (H);

SEQ ID NO: 111 is a sequence of the general formula: X6-1-X7-X8-X9-X10-X11-X12-X13-Y-Y-A-D-S-V-X14-G (SEQ ID NO: 111),
wherein X6 is glycine (G), serine (S), leucine (L), alanine (A), or valine (V),
X7 is tyrosine (Y), or serine (S),
X8 is serine (S), tyrosine (Y), histidine (H), proline (P), or glycine (G),
X9 is serine (S), glycine (G), asparagine (N), or aspartic acid (D),
X10 is serine (S), glycine (G), or aspartic acid (D),
X11 is serine (S), or glycine (G),
X12 is asparagine (N), or serine (S),
X13 is isoleucine (I), threonine (T), or lysine (K), and
X14 is lysine (K) or glutamic acid (E);

SEQ ID NO: 112 is a sequence of the general formula: X15-G-S-S-N-1-G-X16-N-X17-V-X18 (SEQ ID NO: 112),
wherein X15 is serine (S) or threonine (T),
X16 is asparagine (N), or serine (S),
X17 is serine (S), tyrosine (Y), or aspartic acid (D), and
X18 is tyrosine (Y), threonine (T), asparagine (N), or serine (S);

SEQ ID NO: 113 is a sequence of the general formula: X19-X20-X21-X22-R-P-S (SEQ ID NO: 113),
wherein X19 is serine (S), alanine (A), asparagine (N), or glutamic acid (E),
X20 is aspartic acid (D), asparagine (N), threonine (T), or valine (V),
X21 is serine (S), or asparagine (N), and
X22 is glutamine (Q), asparagine (N), histidine (H), or glycine (G); and SEQ ID NO: 114 is a sequence of the general formula: X23-X24-W-D-X25-S-L-X26-X27 (SEQ ID NO: 114),
wherein X23 is glycine (G) or alanine (A),
X24 is threonine (T), alanine (A), or serine (S),
X25 is tyrosine (Y), aspartic acid (D), serine (S), or alanine (A),
X26 is asparagine (N), or serine (S), and
X27 is glycine (G), or alanine (A).

In one particular embodiment, the anti-idiotype antibody that specifically binds to an idiotope site of an anti-c-Met antibody may include at least one heavy chain complementarity determining region (CDR) selected from the group consisting of CDR-H1 containing an amino acid sequence selected from the group consisting of SEQ ID NO: 115 to SEQ ID NO: 124, CDR-H2 containing an amino acid sequence selected from the group consisting of SEQ ID NO: 125 to SEQ ID NO: 138, and CDR-H3 containing an amino acid sequence selected from the group consisting of SEQ ID NO: 139 to SEQ ID NO: 154, or a heavy chain variable region including the at least one heavy chain complementarity determining region;

at least one light chain complementarity determining region selected from the group consisting of CDR-L1 containing an the amino acid sequence selected from the group consisting of SEQ ID NO: 155 to SEQ ID NO: 171, CDR-L2 containing an amino acid sequence selected from the group consisting of SEQ ID NO: 172 to SEQ ID NO: 187, and CDR-L3 containing an amino acid sequence selected from the group consisting of SEQ ID NO: 188 to SEQ ID NO: 201, or a light chain variable region including the at least one light chain complementarity determining region;

a combination of the at least one heavy chain complementarity determining region and the at least one light chain complementarity determining region; or a combination of the heavy chain variable regions and the light chain variable regions.

Specific examples of amino acid sequences of the heavy chain complementarity determining regions (CDRs) and the light chain complementarity determining regions of the anti-idiotypic antibody are set forth in the following Table 1 and Table 2. Any combination of the CDRs may be used.

TABLE 1

| Heavy Chain Complementarity Determining Regions (CDR) | | |
|---|---|---|
| CDR-H1 | CDR-H2 | CDR-H3 |
| DYYMS (SEQ ID NO: 115) | GIYSSSSNIYYADSVKG (SEQ ID NO: 125) | KALGNQENEPTSYSNGMDV (SEQ ID NO: 139) |
| NYAMS (SEQ ID NO: 116) | SISSSGGNTYYADSVKG (SEQ ID NO: 126) | KYHSVFDY (SEQ ID NO: 140) |
| DYDMS (SEQ ID NO: 117) | LISYGGSNTYYADSVKG (SEQ ID NO: 127) | KFRSEFNENEPSSYYGMDV (SEQ ID NO:141) |
| GYDMS (SEQ ID NO: 118) | GISHGDGNIYYADSVKG (SEQ ID NO: 128) | KVGLLFVQEEPSYYNAMDV (SEQ ID NO: 142) |
| DYDMS (SEQ ID NO: 117) | SISYGGGSIYYADSVKG (SEQ ID NO: 129) | RDAAYFDY (SEQ ID NO: 143) |
| GYDMS (SEQ ID NO: 118) | GISYNGGSKYYADSVKG (SEQ ID NO: 130) | KYLLPVLEEPGYSADGMDV (SEQ ID NO: 144) |
| DYYMS (SEQ ID NO: 115) | AISHSSGNTYYADSVKG (SEQ ID NO: 131) | KHLGAQSDEPDSSSNGMDV (SEQ ID NO: 145) |

TABLE 1 -continued

Heavy Chain Complementarity Determining Regions (CDR)

| CDR-H1 | CDR-H2 | CDR-H3 |
|---|---|---|
| NYAMS (SEQ ID NO: 116) | AIYPGGGNTYYADSVKG (SEQ ID NO: 132) | KSLSTHSVDEPSSDNAMDV (SEQ ID NO: 146) |
| DYAMS (SEQ ID NO: 119) | AISSGDGNTYYADSVKG (SEQ ID NO: 133) | RYLGTTSDEPASYSNGMDV (SEQ ID NO: 147) |
| DYAMS (SEQ ID NO: 119) | SIYPDDGNTYYADSVKG (SEQ ID NO: 134) | KYRLVDRWEEPSSDYGMDV (SEQ ID NO: 148) |
| NYSMS (SEQ ID NO: 120) | SISSSGGNTYYADSVKG (SEQ ID NO: 126) | RVHLYFDY (SEQ ID NO: 149) |
| SYAMH (SEQ ID NO: 121) | VISYDGSNKYYADSVKG (SEQ ID NO: 135) | REDNTRYFEEPNYYGMDV (SEQ ID NO: 150) |
| SYAIS (SEQ ID NO: 122) | GIIPIFGTANYAQKFQG (SEQ ID NO: 138) | RDRNSYYEEPMYYFDY (SEQ ID NO: 151) |
| SYAIS (SEQ ID NO: 122) | GIIPIFGTANYAQKFQG (SEQ ID NO: 138) | RDRNSYYEEPMYYFDY (SEQ ID NO: 151) |
| SYGMH (SEQ ID NO: 123) | VISYDGSNKYYADSVKG (SEQ ID NO: 135) | RDLVADDYGDYGTVDY (SEQ ID NO: 152) |
| SYAMS (SEQ ID NO: 124) | AISGSGGSTYYADSVEG (SEQ ID NO: 136) | KERLEEPGFFDY (SEQ ID NO: 153) |
| SYAMS (SEQ ID NO: 124) | AISGSGGSTYYADSVKG (SEQ ID NO: 137) | ARGGGYSYGYEEPYYYYGMDV (SEQ ID NO: 154) |

TABLE 2

Light Chain Complementarity Determining Regions (CDR)

| CDR-L1 | CDR-L2 | CDR-L3 |
|---|---|---|
| SGSSSNIGNNSVY (SEQ ID NO: 155) | SDSQRPS (SEQ ID NO: 172) | GTWDYSLNG (SEQ ID NO: 188) |
| SGSSSNIGNNYVY (SEQ ID NO: 156) | ANNQRPS (SEQ ID NO: 173) | GAWDDSLSG (SEQ ID NO: 189) |
| SGSSSNIGNNDVT (SEQ ID NO: 157) | SDSNRPS (SEQ ID NO: 174) | GTWDSSLSA (SEQ ID NO: 190) |
| TGSSSNIGSNNVT (SEQ ID NO: 158) | SNSHRPS (SEQ ID NO: 175) | GTWDDSLNG (SEQ ID NO: 191) |
| SGSSSNIGNNSVN (SEQ ID NO: 159) | ANNNRPS (SEQ ID NO: 176) | GAWDASLNG (SEQ ID NO: 192) |
| TGSSSNIGSNYVS (SEQ ID NO: 160) | SDSNRPS (SEQ ID NO: 177) | ATWDASLSA (SEQ ID NO: 193) |
| TGSSSNIGNNDVY (SEQ ID NO: 161) | SDSNRPS (SEQ ID NO: 177) | GTWDDSLNG (SEQ ID NO: 191) |
| TGSSSNIGSNSVS (SEQ ID NO: 162) | DDSNRPS (SEQ ID NO: 178) | ASWDYSLNA (SEQ ID NO: 194) |
| SGSSSNIGSNDVY (SEQ ID NO: 163) | SDNNRPS (SEQ ID NO: 179) | GAWDDSLSG (SEQ ID NO: 189) |
| TGSSSNIGSNNVN (SEQ ID NO: 164) | ADSQRPS (SEQ ID NO: 180) | GSWDSSLSG (SEQ ID NO: 195) |
| SGSSSNIGSNSVN (SEQ ID NO: 165) | SDSHRPS (SEQ ID NO: 181) | GSWDDSLSG (SEQ ID NO: 196) |
| TGSSSNIGAAYEVH (SEQ ID NO: 166) | DTSNRPS (SEQ ID NO: 182) | AAWDDSLNG (SEQ ID NO: 197) |

TABLE 2 -continued

Light Chain Complementarity Determining Regions (CDR)

| CDR-L1 | CDR-L2 | CDR-L3 |
|---|---|---|
| SGDKLGDRYVF (SEQ ID NO: 167) | DDSDRPS (SEQ ID NO: 183) | QVWDSVNDH (SEQ ID NO: 198) |
| SGSGSNIGSNAVN (SEQ ID NO: 168) | SNNQRPS (SEQ ID NO: 184) | AAWDDSLNG (SEQ ID NO: 197) |
| GGNNIATKGVH (SEQ ID NO: 169) | DDSGRPS (SEQ ID NO: 185) | QLWDGRSDQ (SEQ ID NO: 199) |
| TGTSSDVGGYNYVS (SEQ ID NO: 170) | EVSNRPS (SEQ ID NO: 186) | SSYTTDNA (SEQ ID NO: 200) |
| KSSQSLLNSGNQKNDLA (SEQ ID NO: 171) | GASTRES (SEQ ID NO: 187) | QNDHSYP (SEQ ID NO: 201) |

In one specific embodiment, the anti-idiotype antibody may include a heavy chain variable region containing an amino acid sequence selected from the group consisting of SEQ ID NO: 202 to SEQ ID NO: 218; a light chain variable region containing an amino acid sequence selected from the group consisting of SEQ ID NO: 236 to SEQ ID NO: 252; or a combination of the heavy chain variable region and the light chain variable region.

In a particular embodiment, the anti-idiotype antibody or antigen-binding fragment thereof that specifically binds to an idiotope site of an anti-c-Met antibody may be a mouse-derived antibody, a mouse-human chimeric antibody, a humanized antibody, or a human antibody. The antibody or antigen-binding fragment thereof may be isolated from (that is, not originally present in) a living body or non-naturally occurring. The antibody or antigen-binding fragment thereof may be monoclonal or synthetic.

In a particular embodiment, the anti-idiotype antibody that specifically binds to an idiotope site of an anti-c-Met antibody may be in the form of an antigen-binding fragment selected from the group consisting of scFv, (scFv)$_2$, scFvFc, Fab, Fab', and F(ab')$_2$, as well as in the form of a complete antibody (e.g., a full IgG type, etc.). A definition for the antigen-binding fragment is as described above in relation to the anti-c-Met antibody.

The anti-idiotype antibody that specifically binds to an idiotope site of an anti-c-Met antibody may include a heavy chain constant region and/or a light chain constant region. The heavy chain constant region and/or the light chain constant region may be derived from immunoglobulins of humans or animals except humans (e.g., mice), for example, hIgG1, hIgG2, hIgG3, hIgG4, mIgG1, mIgG2a, mIgG2b, mIgG3, mIgM, etc.

The anti-idiotype antibody that specifically binds to an idiotope site of an anti-c-Met antibody may include a hinge, which may be derived from immunoglobulins of humans or animals except humans (e.g., mice), for example, IgG1, IgG2, etc., which may be identical to or different from that from which the heavy chain constant region is derived.

The anti-idiotype antibody that specifically binds to an idiotope site of an anti-c-Met antibody may be monoclonal antibodies. The monoclonal antibodies may be prepared by a well-known method in the art. For instance, they may be prepared using a phage display technique.

In addition, individual monoclonal antibodies may be screened on the basis of a binding potential to the anti-c-Met antibody using a typical ELISA (Enzyme-Linked Immu-noSorbent Assay) format. An inhibitory activity may be examined through functionality analysis such as Competitive ELISA for examining molecular interaction to an assembled body or functionality analysis such as a cell-based assay. Then, with regard to monoclonal antibodies selected on the basis of their strong inhibitory activities, their individual affinity (Kd value) or binding affinity to the anti-c-Met antibody is examined.

In one embodiment, the affinities (Kd values) of the anti-idiotype antibodies against the anti-c-Met antibody to the anti-c-Met antibody or may be about 50 nM or less, for example, from about 0.001 to about 50 nM, or from about 0.01 to about 40 nM.

Since the anti-idiotype antibody that specifically binds to an idiotope site of an anti-c-Met antibody or an antibody fragment of the anti-c-Met antibody an antigen-binding fragment thereof specifically binds to the anti-c-Met antibody, the anti-c-Met antibody may be detected using the anti-idiotype antibody or an antigen-binding fragment thereof. The detection of the anti-c-Met antibody using the anti-idiotype antibodies that specifically bind to an idiotope site of an anti-c-Met antibody or the antigen-binding fragments thereof may be applied to monitor a half-life of the antibody, an effective concentration thereof, the remaining concentration, success or failure in targeting a target organ, and the like.

Accordingly, one embodiment provides a composition for detecting an anti-c-Met antibody including the anti-idiotype antibody that specifically binds to an idiotope site of an anti-c-Met antibody or the antigen-binding fragment thereof.

Another embodiment provides a method for detecting an anti-c-Met antibody including the steps of:

Treating (or contacting) a biological sample with the anti-idiotype antibody that specifically binds to an idiotope site of an anti-c-Met antibody or the antigen-binding fragment thereof; and determining the presence or absence of an antigen-antibody reaction.

Another embodiment provides a use of the anti-idiotype antibody that specifically binds to an idiotope site of an anti-c-Met antibody and the antigen-binding fragment thereof for detecting the anti-c-Met antibody.

The use of the anti-idiotype antibody that specifically binds to an idiotope site of an anti-c-Met antibody and the antigen-binding fragment thereof for detecting the anti-c-Met antibody may be applied to monitor the concentration of the anti-c-Met antibody in body after the administration thereof into the body, success or failure in targeting at a target organ, degree of targeting, etc.

In one particular embodiment, the method for detecting an anti-c-Met antibody may be performed by immunoassay using anti-idiotype antibodies as described above as a capture agent and a detector. The anti-idiotype antibodies used as the capture agent and detector may be identical or different. The anti-idiotype antibodies used as the capture agent and detector may be probed with a different or identical probe. The probe may be selected from any detectable label or tag, e.g., fluorescence substances and luminescence substances, which are ordinarily used in immunoassay.

The biological sample may be selected from the group consisting of cells, tissues, body fluids, and the like obtained (isolated) from a subject. For example, the sample may be a serum, for example, a serum isolated from a subject. The subject may include mammals, including primates such as humans and monkeys and rodents such as mice and rats and for example, the subject may be a patient to whom an anti-c-Met antibody is administered.

The step of determining the presence/absence of an antigen-antibody reaction may be performed through various methods known in the art. For instance, it may be measured through an ordinary enzyme reaction, fluorescence, luminescence and/or radiation detection and in particular, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA) and western blotting, but is not limited thereto.

The presence/absence of the anti-c-Met antibody in the biological sample and/or the concentration of the anti-c-Met antibody may be determined by the method for detecting the anti-c-Met antibody as described above. When the subject from whom the biological sample is obtained is a patient to whom the anti-c-Met antibody has been administered, the remaining amount of the administered anti-c-Met antibody and/or distribution location thereof can be checked.

Meanwhile, if the occurring frequency of an anti-drug antibody against the anti-c-Met antibody should be measured, an anti-idiotype antibody may be used as a positive control and applied as a standard sample for quantification. After the anti-c-Met antibody is administered via an intravenous injection to a subject to be tested, a serum may be obtained therefrom after a certain period of time, followed by analysis by an enzyme-linked immunosorbent assay. A change in absorption according to the concentrations of the anti-idiotype antibody within the serum is measured, and a formula between the concentration and absorption is thus derived. Next, a drug to be analyzed is (intravenously) administered to a subject, then a serum is obtained from the subject at a desired time, and is then diluted at a certain ratio and then, the absorption thereof is measured on the same plate by the same methods as above. The absorption results may be applied to the formula regarding absorption change according to the concentrations of the anti-idiotype antibody that specifically binds to an idiotope site of an anti-c-Met antibody to quantify the concentration of the antibody in the serum. The concentration may be referred to as a concentration of an anti-drug antibody (ADA) against a test drug. Thus, the amount of a desired anti-drug antibody at a desired time may be measured by back calculation using the absorption change results according to the concentrations of the anti-idiotype antibody that specifically binds to an idiotope site of an anti-c-Met antibody.

Another embodiment of the present invention provides an analysis method of an anti-drug antibody using the anti-idiotype antibody that specifically binds to an idiotope site of an anti-c-Met antibody, for example, quantification analysis method. More particularly, the analysis method of an anti-drug antibody may include measuring the absorption of a serum isolated from a patient to whom a test drug has been intravenously administered; and comparing the obtained absorption results with the absorption change of an anti-idiotype antibody in a serum isolated from a patient to whom an anti-c-Met antibody has been administered. The step of measuring absorption of the serum isolated from a patient to whom a test drug has been intravenously administered may be carried out by the same conditions and methods as the absorption measurement of the anti-idiotype antibody in the serum isolated from the patient to whom the anti-c-Met antibody has been administered. The patient may include mammals, including primates such as humans and monkeys and rodents such as mice and rats and for example, the subject may be a patient to whom an anti-c-Met antibody is administered. For example, this method may be applied to an animal (e.g., monkey, etc.) toxicity study as well as to quantification of the anti-drug antibody in human serum.

As the anti-idiotype antibody that specifically binds to an idiotope site of an anti-c-Met antibody competes with a c-Met protein which is an antigen of the anti-c-Met antibody, in binding to the anti-c-Met antibody, it can be said to be structurally similar to the c-Met protein. Using this aspect, the anti-idiotype antibody that specifically binds to an idiotope site of an anti-c-Met antibody or the antigen-binding fragment thereof may be applied as a vaccine for c-Met related diseases.

Another embodiment of the invention provides a vaccine composition for a c-Met related disease including the anti-idiotype antibody that specifically binds to an idiotope site of an anti-c-Met antibody or the antigen-binding fragment thereof as an active ingredient. Another embodiment provides a method of immunizing a subject against a c-Met related disease including administering the anti-idiotype antibody or antigen-binding fragment to the subject.

The vaccine composition or the anti-idiotype antibody or antigen-binding fragment may be administered to mammals, including primates such as humans and monkeys and rodents such as mice and rats, for instance, patients who are likely to develop c-Met related diseases or suffer from c-Met related diseases.

The vaccine composition or the anti-idiotype antibody or antigen-binding fragment may further include a pharmaceutically acceptable carrier, and the carrier may be those commonly used for the formulation of drugs and may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative which are commonly used for the preparation of pharmaceutical compositions.

The vaccine composition or the anti-idiotype antibody or antigen-binding fragment may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

The content of the anti-idiotype antibody that specifically binds to an idiotope site of an anti-c-Met antibody or the antigen-binding fragment thereof in the pharmaceutical composition may be prescribed in a variety of ways, depending on factors such as formulation methods, administration methods, age of patients, body weight, gender, pathologic conditions, diets, administration time, administration route, excretion speed, and reaction sensitivity. For instance, a single dosage of the anti-idiotype antibody against the anti-c-Met antibody or the antigen-binding fragment thereof may be in the range of about 0.001 to about 100 mg/kg, particularly about 0.01 to 1 about 00 mg/kg, more particularly about 0.1 to about 50 mg/kg, but is not limited thereto. The single dosage may be formulated into a single formulation in a unit dosage form or formulated in suitably divided dosage forms, or it may be manufactured to be contained in a multiple dosage container.

The vaccine composition may be a solution in oil or an aqueous medium, a suspension, syrup, or an emulsifying solution, or formulated into the form of an extract, powder, granules, a tablet, or a capsule, and it may further include a dispersing or a stabilizing agent.

In particular, since the vaccine composition including the anti-idiotype antibody against the anti-c-Met antibody or the antigen-binding fragment thereof includes an antibody or an antigen-binding fragment thereof, it may be formulated as an immunoliposome. The liposome containing an antibody may be prepared using a well-known method in the pertinent art. The immunoliposome is a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide exchange reaction.

The c-Met related diseases refer to any diseases induced by c-Met expression or overexpression, for example, a cancer. The cancer may be caused by c-Met expression or overexpression. The cancer may be a solid cancer or hematological cancer and it may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, and the like. The cancer may include a metastatic cancer as well as a primary cancer. Besides cancer, the c-Met related diseases may include gestational diabetes.

In another embodiment, there is provided a polypeptide molecule including the heavy chain complementarity determining region of the anti-idiotype antibody that specifically binds to an idiotope site of an anti-c-Met antibody, the light chain complementarity determining region of the anti-idiotype antibody that specifically binds to an idiotope site of an anti-c-Met antibody, or a combination thereof; or the heavy chain variable region of the anti-idiotype antibody that specifically binds to an idiotope site of an anti-c-Met antibody, the light chain variable region of the anti-idiotype antibody that specifically binds to an idiotope site of an anti-c-Met antibody, or a combination thereof.

The polypeptide molecule may serve as a precursor of an antibody, which can be not only used to manufacture the antibody but also included as a component of a protein scaffold (e.g., peptibody) having a structural similar to an antibody, a bispecific antibody (constituting the c-Met binding site of the double antigen-binding sites of a double antibody), and a multi-specific antibody (constituting the c-Met binding site of the multiple antigen-binding sites of a multi-specific antibody).

The polypeptide molecule may include one or more polypeptides selected from the group consisting of a polypeptide including the amino acid sequence of SEQ ID NO: 109 (for example, an amino acid sequence selected from the group consisting of SEQ ID NO: 115 to SEQ ID NO: 120) or the amino acid sequence of SEQ ID NO: 110 (for example, an amino acid sequence selected from the group consisting of SEQ ID NO: 121 to SEQ ID NO: 124), a polypeptide including the amino acid sequence of SEQ ID NO: 111 (for example, an amino acid sequence selected from the group consisting of SEQ ID NO: 125 to SEQ ID NO: 137) or the amino acid sequence of SEQ ID NO: 138, and a polypeptide including an amino acid sequence selected from the group consisting of SEQ ID NO: 139 to SEQ ID NO: 154;

one or more polypeptides selected from the group consisting of a polypeptide including the amino acid sequence of SEQ ID NO: 112 (for example, an amino acid sequence selected from the group consisting of SEQ ID NO: 155 to SEQ ID NO: 165) or an amino acid sequence selected from the group consisting of SEQ ID NO: 166 to SEQ ID NO: 171, a polypeptide including the amino acid sequence of SEQ ID NO: 113 (for example, an amino acid sequence selected from the group consisting of SEQ ID NO: 172 to SEQ ID NO: 186) or the amino acid sequence of SEQ ID NO: 187, and a polypeptide including the amino acid sequence of SEQ ID NO: 114 (for example, an amino acid sequence selected from the group consisting of SEQ ID NO: 188 to SEQ ID NO: 197) or an amino acid sequence selected from the group consisting of SEQ ID NO: 198 to SEQ ID NO: 201; or a combination thereof.

In a specific embodiment, the polypeptide molecule may include an amino acid sequence selected from the group consisting of SEQ ID NO: 202 to SEQ ID NO: 218; an amino acid sequence selected from the group consisting of SEQ ID NO: 236 to SEQ ID NO: 252; or a combination thereof.

In another embodiment, there is provided a polynucleotide molecule encoding the polypeptide molecule or a recombinant vector including the polynucleotide. In particular, the polynucleotide molecule may include a nucleotide sequence selected from the group consisting of SEQ ID NO: 219 to SEQ ID NO: 235, a nucleotide sequence selected from the group consisting of SEQ ID NO: 253 to SEQ ID NO: 269, or a combination thereof.

The term "vector" used herein refers to a means for expressing a target gene in a host cell. For example, a vector may include a plasmid vector, a cosmid vector, and a virus vector such as a bacteriophage vector, an adenovirus vector, a retrovirus vector and an adeno-associated virus vector. Suitable recombinant vectors may be constructed by manipulating plasmids often used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, SV40).

In the recombinant vector, the polynucleotides encoding the protein complex may be operatively linked to a promoter. The term "operatively linked" used herein refers to a functional linkage between a nucleotide expression regulating sequence (for example, a promoter sequence) and other nucleotide sequences. Thus, the regulating sequence may regulate the transcription and/or translation of the other nucleotide sequences by being operatively linked.

The recombinant vector may be constructed typically for either cloning or expression. The expression vector may be any ordinary vectors known in the pertinent art for expressing an exogenous protein in plants, animals, or microorganisms. The recombinant vector may be constructed using various methods known in the art.

The recombinant vector may be constructed using a prokaryotic cell or a eukaryotic cell as a host. For example, when a prokaryotic cell is used as a host cell, the expression vector used generally includes a strong promoter capable of initiating transcription (for example, pL$^\lambda$ promoter, CMV promoter, trp promoter, lac promoter, tac promoter, T7 promoter, etc.), a ribosome binding site for initiating translation, and a transcription/translation termination sequence. When a eukaryotic cell is used as a host cell, the vector used generally includes the origin of replication acting in the eukaryotic cell, for example, a f1 replication origin, a SV40 replication origin, a pMB1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV). A transcription termination sequence in an expression vector for a eukaryotic host cell may be, in general, a polyadenylation sequence.

Another embodiment provides a recombinant cell including the recombinant vector.

The recombinant cell may be those obtained by transfecting the recombinant vector into a suitable host cell. Any host cells known in the pertinent art to enable stable and continuous cloning or expression of the recombinant vector may be used as the host cell. Suitable prokaryotic host cells may include *E. coli* JM109, *E. coli* BL21, *E. coli* RR1, *E. coli* LE392, *E. coli* B, *E. coli* X 1776, *E. coli* W3110, *Bacillus* species strains such as *Bacillus subtillis* or *Bacillus thuringiensis*, intestinal bacteria and strains such as *Salmonella typhymurum, Serratia marcescens*, and various *Pseudomonas* species. Suitable eukaryotic host cells to be transformed may include yeasts, such as *Saccharomyce cerevisiae*, insect cells, plant cells, and animal cells, for example, Sp2/0, Chinese hamster ovary (CHO) K1, CHO DG44, PER.C6, W138, BHK, COS-7, 293, HepG2, Huh7, 3T3, RIN, and MDCK cell lines, but are not limited thereto.

The polynucleotide or the recombinant vector including the same may be transferred (transfected) into a host cell by using known transfer methods. Suitable transfer methods for prokaryotic host cells may include a method using $CaCl_2$ and electroporation. Suitable transfer methods for eukaryotic host cells may include microinjection, calcium phosphate precipitation, electroporation, liposome-mediated transfection, and gene bombardment, but are not limited thereto.

A transformed host cell may be selected using a phenotype expressed by a selected marker by any methods known in the art. For example, if the selected marker is a gene that is resistant to a specific antibiotic, a transformant may be easily selected by being cultured in a medium including the antibiotic.

The present invention can not only improve the accuracy of anti-c-Met antibody analysis by providing an anti-idiotype antibody that specifically binds to an idiotope site of an anti-c-Met antibody, compared to the pre-existing PK methods, but may also be applied to clinical sample analysis of the anti-c-Met antibody and applied to measurement analysis of an anti-drug antibody (ADA) to be able to learn the presence/absence of ADA production and quantification thereof. Also, it is expected that the anti-idiotype antibody against the anti-c-Met antibody may be utilized as a vaccine for c-Met related diseases.

Hereafter, the present invention will be described in detail by examples.

The following examples are intended merely to illustrate the invention and are not construed to restrict the invention.

EXAMPLES

Reference Example 1: Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1\times10^8$ cells) were mixed with myeloma cells (Sp2/0) ($1\times10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 9, 2009 with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody induces immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™ 3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 1, below.

TABLE 1

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 2 and were converted into IgG forms. Four antibodies which were respectively produced from clones L3-1, L3-2, L3-3, and L3-5 were used in the subsequent experiments.

TABLE 2

| Clone | Library constructed | CDR Sequence |
| --- | --- | --- |
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™ 3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and referred as "anti-c-Met antibody".

Example 1: Preparation of Anti-Idiotype Antibody Against Anti-c-Met Antibody

Using a phage display scFv library (construction of a large synthetic human scFv library with six diversified CDRs and high functional diversity. 2009, Mol. cells., 27, pp. 225-235; A human scFv antibody generation pipeline for proteome research. 2010, J. Biotechnol., 152, pp. 159-170), binders recognizing and binding to the anti-c-Met antibody prepared in the above reference example as an antigen were screened to eliminate candidates binding to the Fc site of the antibody.

In particular, the anti-c-Met antibody prepared in the above reference example was immobilized in amounts of about 10 µg (microgram), 2 µg, 0.4 µg, and 0.1 µg, respectively on Dynabeads (Dynal, #143.01) to enrich antibodies that reacted to the anti-c-Met antibody through $1^{st}$, $2^{nd}$, $3^{rd}$ and $4^{th}$ pannings. The surface of Dynabeads was blocked using about 1% (w/v) BSA dissolved in a PBS, and about $1 \times 10^{11}$ to $1 \times 10^{12}$ of phage particles derived from the same phage display scFv library as described in the above were added to about 0.5 ml of 1% (w/v) BSA and let stand at a room temperature for one hour for blocking. Thereafter, the phages blocked with BSA were added to the Dynabeads on which the anti-c-Met antibodies blocked with BSA were immobilized to bind the anti-c-Met antibodies and the phages by rotation at a room temperature for 2 hours. Especially, during the $2^{nd}$, $3^{rd}$ and $4^{th}$ pannings, in order to eliminate in advance phage particles binding to the Fc portions, prior to binding the phages to the Dynabeads on which the anti-c-Met antibodies were immobilized, the Dynabeads were mixed with the phages blocked with hIgG1 and BSA in an amount corresponding to 1000 times the immobilized anti-c-Met antibodies to react at a room temperature for one hour and then, the phages were bound to the Dynabeads on which the anti-c-Met antibodies were immobilized.

After the binding treatment of the phages, the surfaces of the phages were washed 1 to 5 times with 0.1% (v/v) Tween 20 dissolved in a PBS and then, the bound phages were eluted using 100 mM glycine-HCl, pH 2.2 solution. The eluted phages were used to infect *E. coli* XL1-Blue MRF' cells (Agilent, USA) and after amplified, they were obtained to prepare for the next screening step. Such procedures were repeated four times by immobilizing the anti-c-Met antibodies on Dynabeads in amounts of 10 μg (microgram), 2 μg, 0.4 μg, and 0.1 μg, respectively, followed by ELISA (Enzyme-Linked ImmunoSorbent Assay) affinity assay to identify anti-c-Met antibody binding scFv clones which recognize the anti-c-Met antibody.

In order to identify the anti-c-Met antibody binding scFv clones, the anti-c-Met antibody was seeded at 1 μg/ml onto each well of a 96-well plate to perform coating at 4° C. for 16 to 18 hours and then blocked with about 1% (w/v) BSA dissolved in a PBS at a room temperature for one hour. Thereafter, the anti-c-Met antibody binding scFv clones which were cultured in advance were seeded at 50 ul onto each well to react at 37° C. for 2 hours and then washed three times with 0.1% (v/v) Tween 20 dissolved in a PBS. Then, a 1:3000 dilution of anti-M13-HRP was seeded at 100 ul onto each well to react at 37° C. for one hour and then washed three times with 0.1% (v/v) Tween 20 dissolved in a PBS and finally, absorption was measured at 450 nm after color development using TMB (3,3,5,5-tetramethylbenzidine).

17 kinds of binding clones were selected by the ELISA method as above, and in order to convert them into full IgG1 forms, oligomers encoding the heavy chain variable regions and the light chain variable regions of each clone were synthesized through IDT. Thereafter, genes of the 17 heavy chain variable regions and light chain variable regions were amplified through a PCR, and the heavy chain variable regions were inserted into pOptivec into which human IgG1 hinge and human IgG1 constant regions were inserted and the light chain variable regions were inserted into pcDNA 3.3 into which human light chain constant regions were inserted and then, their sequencing was performed by Bionics Inc. Finally, to obtain vectors for expressing antibodies.

Each sequence of the 17 kinds of the selected antibody heavy chain CDR, light chain CDR, heavy chain variable regions, light chain variable regions, heavy chain constant regions, and light chain constant regions was set forth in Tables 5 to 8 below.

The above constructed vectors were each amplified using Qiagen Maxiprep kit (Cat no. 12662), and temporary expression thereof proceeded using Freestyle™ MAX 293 Expression System (invitrogen). The cells used were 293 F cells, which were cultured in a suspension culture manner using FreeStyle™ 293 Expression Medium as a medium. One day before the temporary expression, the cells were prepared at a concentration of $5 \times 10^6$ cells/ml and after 24 hours, their temporary expression started when the number of the cells reached $1 \times 10^6$ cells/ml. Transfection was performed by a liposomal reagent method using Freestyle™ MAX reagent (invitrogen). DNA was prepared in a 15-ml tube in a ratio of heavy chain DNA:light chain DNA=1:1 and mixed with 2 ml of OptiPro™ SFM (invtrogen) (A), and 100 μl of Freestyle™ MAX reagent and 2 ml of OptiPro™ SFM were mixed in another 15-ml tube (B), and after (A) and (B) were mixed and incubated for 15 min., the mixture solution was then slowly mixed into the cells which were prepared one day before. After the transfection was complete, the cells were cultured in a 37° C., 80% humidity, 8% $CO_2$, 130 rpm incubator for 5 days.

The cultured cells were centrifuged to obtain each 100 ml of supernatants, which were then purified using AKTA Prime (GE healthcare). The culture was flowed at a flow rate of 5 ml/min. onto the AKTA Prime installed with Protein A column (GE healthcare, 17-0405-03) to perform elution using an IgG elution buffer (Thermo Scientific, 21004). The buffer was replaced by a PBS buffer to finally obtain 17 kinds of antibodies.

Sequences of the purified 17 kinds of antibody heavy chain CDR, light chain CDR, heavy chain variable regions, light chain variable regions, heavy chain constant regions, and light chain constant regions were set forth in Tables 5 to 10 below.

TABLE 5

| Heavy Chain CDR | | | |
|---|---|---|---|
| Antibody | CDR-H1 | CDR-H2 | CDR-H3 |
| EW01 | DYYMS (SEQ ID NO: 115) | GIYSSSSNIYYADSVKG (SEQ ID NO: 125) | KALGNQENEPTSYSNGM DV (SEQ ID NO: 139) |
| EW02 | NYAMS (SEQ ID NO: 116) | SISSSGGNTYYADSVKG (SEQ ID NO: 126) | KYHSVFDY (SEQ ID NO: 140) |
| EW03 | DYDMS (SEQ ID NO: 117) | LISYGGSNTYYADSVKG (SEQ ID NO: 127) | KFRSEFNENEPSSYYGM DV (SEQ ID NO: 141) |
| EW06 | GYDMS (SEQ ID NO: 118) | GISHGDGNIYYADSVKG (SEQ ID NO: 128) | KVGLLFVQEEPSYYNAMD V (SEQ ID NO: 142) |
| EW09 | DYDMS (SEQ ID NO: 117) | SISYGGGSIYYADSVKG (SEQ ID NO: 129) | RDAAYFDY (SEQ ID NO: 143) |
| EW10 | GYDMS (SEQ ID NO: 118) | GISYNGGSKYYADSVKG (SEQ ID NO: 130) | KYLLPVLEEPGYSADGMD V (SEQ ID NO: 144) |
| EW16 | DYYMS (SEQ ID NO: 115) | AISHSSGNTYYADSVKG (SEQ ID NO: 131) | KHLGAQSDEPDSSSNGM DV (SEQ ID NO: 145) |
| EW26 | NYAMS (SEQ ID NO: 116) | AIYPGGGNTYYADSVKG (SEQ ID NO: 132) | KSLSTHSVDEPSSDNAMD V (SEQ ID NO: 146) |
| EW28 | DYAMS (SEQ ID NO: 119) | AISSGDGNTYYADSVKG (SEQ ID NO: 133) | RYLGTTSDEPASYSNGMD V (SEQ ID NO: 147) |

TABLE 5-continued

| Heavy Chain CDR | | | |
|---|---|---|---|
| Antibody | CDR-H1 | CDR-H2 | CDR-H3 |
| EW34 | DYAMS (SEQ ID NO: 119) | SIYPDDGNTYYADSVKG (SEQ ID NO: 134) | KYRLVDRWEEPSSDYGMDV (SEQ ID NO: 148) |
| EW37 | NYSMS (SEQ ID NO: 120) | SISSSGGNTYYADSVKG (SEQ ID NO: 126) | RVHLYFDY (SEQ ID NO: 149) |
| HAL 7-1 | SYAMH (SEQ ID NO: 121) | VISYDGSNKYYADSVKG (SEQ ID NO: 135) | REDNTRYFEEPNYYGMDV (SEQ ID NO: 150) |
| HAL 7-2 | SYAIS (SEQ ID NO: 122) | GIIPIFGTANYAQKFQG (SEQ ID NO: 138) | RDRNSYYEEPMYYFDY (SEQ ID NO: 151) |
| HAL 7-5 | SYAIS (SEQ ID NO: 122) | GIIPIFGTANYAQKFQG (SEQ ID NO: 138) | RDRNSYYEEPMYYFDY (SEQ ID NO: 151) |
| HAL 7-7 | SYGMH (SEQ ID NO: 123) | VISYDGSNKYYADSVKG (SEQ ID NO: 135) | RDLVADDYGDYGTVDY (SEQ ID NO: 152) |
| HAL 7-12 | SYAMS (SEQ ID NO: 124) | AISGSGGSTYYADSVEG (SEQ ID NO: 136) | KERLEEPGFFDY (SEQ ID NO: 153) |
| HAL 8-7 | SYAMS (SEQ ID NO: 124) | AISGSGGSTYYADSVKG (SEQ ID NO: 137) | ARGGGYSYGYEEPYYYYGMDV (SEQ ID NO: 154) |

TABLE 6

| Light Chain CDR | | | |
|---|---|---|---|
| Antibody | CDR-L1 | CDR-L2 | CDR-L3 |
| EW01 | SGSSSNIGNNSVY (SEQ ID NO: 155) | SDSQRPS (SEQ ID NO: 172) | GTWDYSLNG (SEQ ID NO: 188) |
| EW02 | SGSSSNIGNNYVY (SEQ ID NO: 156) | ANNQRPS (SEQ ID NO: 173) | GAWDDSLSG (SEQ ID NO: 189) |
| EW03 | SGSSSNIGNNDVT (SEQ ID NO: 157) | SDSNRPS (SEQ ID NO: 174) | GTWDSSLSA (SEQ ID NO: 190) |
| EW06 | TGSSSNIGSNNVT (SEQ ID NO: 158) | SNSHRPS (SEQ ID NO: 175) | GTWDDSLNG (SEQ ID NO: 191) |
| EW09 | SGSSSNIGNNSVN (SEQ ID NO: 159) | ANNNRPS (SEQ ID NO: 176) | GAWDASLNG (SEQ ID NO: 192) |
| EW10 | TGSSSNIGSNYVS (SEQ ID NO: 160) | SDSNRPS (SEQ ID NO: 177) | ATWDASLSA (SEQ ID NO: 193) |
| EW16 | TGSSSNIGNNDVY (SEQ ID NO: 161) | SDSNRPS (SEQ ID NO: 178) | GTWDDSLNG (SEQ ID NO: 191) |
| EW26 | TGSSSNIGSNSVS (SEQ ID NO: 162) | DDSNRPS (SEQ ID NO: 178) | ASWDYSLNA (SEQ ID NO: 194) |
| EW28 | SGSSSNIGSNDVY (SEQ ID NO: 163) | SDNNRPS (SEQ ID NO: 179) | GAWDDSLSG (SEQ ID NO: 189) |
| EW34 | TGSSSNIGSNNVN (SEQ ID NO: 164) | ADSQRPS (SEQ ID NO: 180) | GSWDSSLSG (SEQ ID NO: 195) |
| EW37 | SGSSSNIGSNSVN (SEQ ID NO: 165) | SDSHRPS (SEQ ID NO: 181) | GSWDDSLSG (SEQ ID NO: 196) |
| HAL 7-1 | TGSSSNIGAAYEVH (SEQ ID NO: 166) | DTSNRPS (SEQ ID NO: 182) | AAWDDSLNG (SEQ ID NO: 197) |
| HAL 7-2 | SGDKLGDRYVF (SEQ ID NO: 167) | DDSDRPS (SEQ ID NO: 183) | QVWDSVNDH (SEQ ID NO: 198) |
| HAL 7-5 | SGSGSNIGSNAVN (SEQ ID NO: 168) | SNNQRPS (SEQ ID NO: 184) | AAWDDSLNG (SEQ ID NO: 197) |

TABLE 6 -continued

Light Chain CDR

| Antibody | CDR-L1 | CDR-L2 | CDR-L3 |
|---|---|---|---|
| HAL 7-7 | GGNNIATKGVH (SEQ ID NO: 169) | DDSGRPS (SEQ ID NO: 185) | QLWDGRSDQ (SEQ ID NO: 199) |
| HAL 7-12 | TGTSSDVGGYNYVS (SEQ ID NO: 170) | EVSNRPS (SEQ ID NO: 186) | SSYTTDNA (SEQ ID NO: 200) |
| HAL 8-7 | KSSQSLLNSGNQKNDLA (SEQ ID NO: 171) | GASTRES (SEQ ID NO: 187) | QNDHSYP (SEQ ID NO: 201) |

TABLE 7

Heavy Chain Variable Region

| Antibody | Amino acid sequence | Coding DNA sequence |
|---|---|---|
| EW01 | EVQLLESGGGLVQPGGSLR LSCAVSGFTFSDYYMSWV RQAPGKGLEWVSGIYSSSS NIYYADSVKGRFTISRDNSE NTLYLQMNSLRAEDTAVYY CAKALGNQENEPTSYSNG MDVWGQGTLVTVSS (SEQ ID NO: 202) | GAGGTGCAGCTGTTGGAGTCTGGGGGAGGCTT GGTACAGCCTGGGGGGTCCCTGAGACTCTCCT GTGCAGTCTCTGGATTCACCTTTAGCGATTATA TATGAGCTGGGTCCGCCAGGCTCCAGGGAAGG GGCTGGAGTGGGTCTCAGGGATCTATTCTAGTA GTAGTAATATATATTACGCTGATTCTGTAAAAGGT CGGTTCACCATCTCCAGAGACAATTCCGAGAAC ACGCTGTATCTGCAAATGAACAGCCTGAGAGCC GAGGACACGGCCGTGTATTACTGTGCGAAAGCT CTTGGTAATCAGGAGAATGAGCCGACTTCTTATT CTAATGGTATGGACGTCGGGGCCAGGGTACAC TGGTCACCGTGAGCTCA (SEQ ID NO: 219) |
| EW02 | EVQLLESGGGLVQPGGSLR LSCAASGFTFSNYAMSWVR QAPGKGLEWVSSISSSGGN TYYADSVKGRFTISRDNSK NTLYLQMNSLGAEDTAVYY CAKYHSVFDYWGQGTLVTV SS (SEQ ID NO: 203) | GAGGTGCAGCTGTTGGAGTCTGGGGGAGGCTT GGTACAGCCTGGGGGGTCCCTGAGACTCTCCT GTGCAGCCTCTGGATTCACCTTTAGCAATTATGC TATGAGCTGGGTCCGCCAGGCTCCAGGGAAGG GGCTGGAGTGGGTCTCATCGATCTCTTCTAGTG GTGGTAATACATATTACGCTGATTCTGTAAAAGG TCGGTTCACCATCTCCAGAGACAATTCCAAGAA CACGCTGTATCTGCAAATGAACAGCCTGGGAGC CGAGGACACGGCCGTGTATTACTGTGCGAAATA TCATTCGGTTTTCGACTACTGGGGCCAGGGTAC ACTGGTCACCGTGAGCTCA (SEQ ID NO: 220) |
| EW03 | EVQLLESGGGLVQPGGSLR LSCAASGFTFSDYDMSWV RQAPGKGLEWVSLISYGGS NTYYADSVKGRFTISRDNS KNTLYLQMNSLRAEDTAVY YCAKFRSEFNENEPSSYYG MDVWGQGTLVTVSS (SEQ ID NO: 204) | GAGGTGCAGCTGTTGGAGTCCGGGGGAGGCTT GGTACAGCCTGGGGGGTCCCTGAGACTCTCCT GTGCAGCCTCTGGATTCACCTTTAGCGATTATGA TATGAGCTGGGTCCGCCAGGCTCCAGGGAAGG GGCTGGAGTGGGTCTCATTGATCTCTTATGGTG GTAGTAATACATATTACGCTGATTCTGTAAAAGGT CGGTTCACCATCTCCAGAGACAATTCCAAGAAC ACGCTGTATCTGCAAATGAACAGCCTGAGAGCC GAGGACACGGCCGTGTATTACTGTGCGAAATTT CGTAGTGAGTTTAATGAGAATGAGCCGTCTTCTT ATTATGGTATGGACGTCGGGGCCAGGGTACAC TGGTCACCGTGAGCTCA (SEQ ID NO: 221) |
| EW06 | EVQLLESGGGLVQPGGSLR LSCAASGFTFSGYDMSWV RQAPGKGLEWVSGISHGD GNIYYADSVKGRFTISRDNS KNTLYLQMNSLRAEDTAVY YCAKVGLLFVQEEPSYYNA MDVWGQGTLVTVSS (SEQ ID NO: 205) | GAGGTGCAGCTGTTGGAGTCGGGGGGAGGCT TGGTACAGCCTGGGGGGTCCCTGAGACTCTCC TGTGCAGCCTCTGGATTCACCTTTAGCGGTTAT GATATGAGCTGGGTCCGCCAGGCTCCAGGGAA GGGGCTGGAGTGGGTCTCAGGGATCTCTCATG GTGATGGTAATATATATTACGCTGATTCTGTAAAA GGTCGGTTCACCATCTCCAGAGACAATTCCAAG AACACGCTGTATCTGCAAATGAACAGCCTGAGA GCCGAGGACACGGCCGTGTATTACTGTGCGAA AGTTGGTCTTCTTTTTGTGCAGGAGGAGCCGTC TTATTATAATGCTATGGACGTCGGGGCCAGGGT ACACTGGTCACCGTGAGCTCA (SEQ ID NO: 222) |
| EW09 | EVQLLESGGGLVQPGGSLR LSCAASGFTFSDYDMSWV RQAPGKGLEWVSSISYGG GSIYYADSVKGRFTISRDNS KNTLYLQMNSLRAEDTAMY YCARDAAYFDYWGQGTLVT VSS (SEQ ID NO: 206) | GAGGTGCAGCTGTTGGAGTCTGGGGGAGGCTT GGTACAGCCTGGGGGGTCCCTGAGACTCTCCT GTGCAGCCTCTGGATTCACCTTTAGCGATTATGA TATGAGCTGGGTCCGCCAGGCTCCAGGGAAGG GGCTGGAGTGGGTCTCATCGATCTCTTATGGTG GTAGTATATATATTACGCTGATTCTGTAAAAGG TCGGTTCACCATCTCCAGAGACAATTCCAAGAA |

TABLE 7 -continued

| Heavy Chain Variable Region | | |
|---|---|---|
| Antibody | Amino acid sequence | Coding DNA sequence |
| | | CACGCTGTATCTGCAAATGAACAGCCTGAGAGC<br>CGAGGACACGGCCATGTATTACTGTGCGAGAGA<br>TGCTGCTTATTTCGACTACTGGGGCCAGGGTAC<br>ACTGGTCACCGTGAGCTCA (SEQ ID NO: 223) |
| EW10 | EVQLLESGGGLVQPGGSLR<br>LSCAASGFTFSGYDMSWV<br>RQAPGKGLEWVSGISYNG<br>GSKYYADSVKGRFTISRDN<br>SKNTLYLQMNSLRAEDTAV<br>YYCAKYLLPVLEEPGYSAD<br>GMDVWGQGTLVTVSS<br>(SEQ ID NO: 207) | GAGGTGCAGCTGTTGGAGTCTGGGGGAGGCTT<br>GGTACAGCCTGGGGGGTCCCTGAGACTCTCCT<br>GTGCAGCCTCTGGATTCACCTTTAGCGGTTATG<br>ATATGAGCTGGGTCCGCCAGGCTCCAGGGAAG<br>GGGCTGGAGTGGGTCTCAGGGATCTCTTATAAT<br>GGTGGTAGTAAATATTACGCTGATTCTGTAAAAG<br>GTCGGTTCACCATCTCCAGAGACAATTCCAAGA<br>ACACGCTGTATCTGCAAATGAACAGCCTGAGAG<br>CCGAGGACACGGCCGTGTATTACTGTGCGAAAT<br>ATCTTCTTCCGGTTCTGGAGGAGCCGGGTATT<br>CTGCTGATGGTATGGACGTCTGGGGCCAGGGT<br>ACACTGGTCACCGTGAGCTCA (SEQ ID NO: 224) |
| EW16 | EVQLLESGGGLVQPGGSLR<br>LSCAASGFTFSDYYMSWV<br>RLAPGKGLEWVSAISHSSG<br>NTYYADSVKGRFTISRDNS<br>KNTLYLQMNSLRAEDTAVY<br>YCAKHLGAQSDEPDSSSN<br>GMDVWGQGTLVTVSS<br>(SEQ ID NO: 208) | GAGGTGCAGCTGTTGGAGTCTGGGGGAGGCTT<br>GGTACAGCCTGGGGGGTCCCTGAGACTCTCCT<br>GTGCAGCCTCTGGATTCACCTTTAGCGATTATTA<br>TATGAGCTGGGTCCGCCTGGCTCCAGGGAAGG<br>GGCTGGAGTGGGTCTCAGCGATCTCTCATAGTA<br>GTGGTAATACATATTACGCTGATTCTGTAAAAGG<br>TCGGTTCACCATCTCCAGAGACAATTCCAAGAA<br>CACGCTGTATCTGCAAATGAACAGCCTGAGAGC<br>CGAGGACACGGCCGTGTATTACTGTGCGAAACA<br>TCTTGGTGCGCAGTCGGATGAGCCGGATTCTTC<br>TTCTAATGGTATGGACGTCTGGGGCCAGGGTAC<br>ACTGGTCACCGTGAGCTCA (SEQ ID NO: 225) |
| EW26 | EVQLLESGGGLVQPGGSLR<br>LSCAASGFTFSNYAMSWV<br>RQAPGKGLEWVSAIYPGG<br>GNTYYADSVKGRFTISRDN<br>SKNTLYLQMNSLRAEDTAV<br>YYCAKSLSTHSVDEPSSDN<br>AMDVWGQGTLVTVSS<br>(SEQ ID NO: 209) | GAGGTGCAGCTGTTGGAGTCTGGGGGAGGCTT<br>GGTACAGCCTGGGGGGTCCCTGAGACTCTCCT<br>GTGCAGCCTCTGGATTCACCTTTAGCAATTATGC<br>TATGAGCTGGGTCCGCCAGGCTCCAGGGAAGG<br>GGCTGGAGTGGGTCTCAGCGATCTATCCTGGT<br>GGTGGTAATACATATTACGCTGATTCTGTAAAAG<br>GTCGGTTCACCATCTCCAGAGACAATTCCAAGA<br>ACACGCTGTATCTGCAAATGAACAGCCTGAGAG<br>CCGAGGACACGGCCGTGTATTACTGTGCGAAAT<br>CTCTTAGTACTCATAGTGTGGATGAGCCGTCTTC<br>TGATAATGCTATGGACGTCTGGGGCCAGGGTAC<br>ACTGGTCACCGTGAGCTCA (SEQ ID NO: 226) |
| EW28 | EVQLLESGGGLVQTGGSLR<br>LSCAVSGFTFSDYAMSWVR<br>QAPGKGLEWVSAISSGDG<br>NTYYADSVKGRFTISRDNS<br>KNTLYLQMNSLRAEDTAVY<br>YCARYLGTTSDEPASYSNG<br>MDVWGQGTLVTVSS (SEQ<br>ID NO: 210) | GAGGTGCAGCTGTTGGAGTCTGGGGGAGGCTT<br>GGTACAGACTGGGGGGTCCCTGAGACTCTCCT<br>GTGCAGTCTCTGGATTCACCTTTAGCGATTATGC<br>TATGAGCTGGGTCCGCCAGGCTCCAGGGAAGG<br>GGCTGGAGTGGGTCTCAGCGATCTCTTCTGGT<br>GATGGTAATACATATTACGCTGATTCTGTAAAAG<br>GTCGGTTCACCATCTCCAGAGACAATTCCAAGA<br>ACACGCTGTATCTGCAAATGAACAGCCTGAGAG<br>CCGAGGACACGGCCGTGTATTACTGTGCGAGAT<br>ATCTTGGTACTACGAGTGATGAGCCGGCTTCTTA<br>TTTCTAATGGTATGGACGTCTGGGGCCAGGGTAC<br>ACTGGTCACCGTGAGCTCA (SEQ ID NO: 227) |
| EW34 | EVQLLESGGGLVQTGGSLR<br>LSCAASGFTFSDYAMSWVR<br>QAPGKGLEWVSSIYPDDGN<br>TYYADSVKGRFTISRDNSK<br>NTLYLQMNSLRAEDTAVYY<br>CAKYRLVDRWEEPSSDYG<br>MDVWGQGTLVTVSS (SEQ<br>ID NO: 211) | GAGGTGCAGCTGTTGGAGTCTGGGGGAGGCTT<br>GGTACAGACTGGGGGGTCCCTGAGACTCTCCT<br>GTGCAGCCTCTGGATTCACCTTTAGCGATTATG<br>CTATGAGCTGGGTCCGCCAGGCTCCAGGGAAG<br>GGGCTGGAGTGGGTCTCATCGATCTATCCTGAT<br>GATGGTAATACATATTACGCTGATTCTGTAAAAG<br>GTCGGTTCACCATCTCCAGAGACAATTCCAAGA<br>ACACGCTGTATCTGCAAATGAACAGCCTGAGAG<br>CCGAGGACACGGCCGTGTATTACTGTGCGAAAT<br>ATCGTCTTGTGGATAGGTGGGAGGAGCCGTCTT<br>CTGATTATGGTATGGACGTCTGGGGCCAGGGTA<br>CACTGGTCACCGTGAGCTCA (SEQ ID NO: 228) |
| EW37 | EVQLLESGGGLVQPGGSLR<br>LSCAASGFTFSNYSMSWV<br>RQAPGKGLEWVSSISSSGG<br>NTYYADSVKGRFTISRDNS | GAGGTGCAGCTGTTGGAGTCCGGGGAGGCTT<br>GGTACAGCCTGGGGGGTCCCTGAGACTCTCCT<br>GTGCAGCCTCTGGATTCACCTTTAGCAATTATTC<br>TATGAGCTGGGTCCGCCAGGCTCCAGGGAAGG |

TABLE 7 -continued

Heavy Chain Variable Region

| Antibody | Amino acid sequence | Coding DNA sequence |
|---|---|---|
| | KNTLYLQMNSLRAEDTAVY YCARVHLYFDYWGQGTLVT VSS (SEQ ID NO: 212) | GGCTGGAGTGGGTCTCATCGATCTCTTCTAGTG GTGGTAATACATATTACGCTGATTCTGTAAAAGG TCGGTTCACCATCTCCAGAGACAATTCCAAGAA CACGCTGTATCTGCAAATGAACAGCCTGAGAGC CGAGGACACGGCCGTGTATTACTGTGCGAGAG TGCATTTGTATTTCGACTACTGGGGCCAGGGTA CACTGGTCACCGTGAGCTCA (SEQ ID NO: 229) |
| HAL7-1 | QVQLQQSGGGVVQPGRSL RLSCAASGFTFSSYAMHWV RQAPGKGLEWVAVISYDGS NKYYADSVKGRFTISRDNS KNTLYLQMNSLRAEDTAVY YCAREDNTRYFEEPNYYG MDVWGQGTTVTVSS (SEQ ID NO: 213) | CAGGTACAGCTGCAGCAGTCAGGGGGAGGCGT GGTCCAGCCTGGGAGGTCCCTGAGACTCTCCT GTGCAGCCTCTGGATTCACCTTCAGTAGCTATG CTATGCACTGGGTCCGCCAGGCTCCAGGCAAG GGGCTGGAGTGGGTGGCAGTTATATCATATGAT GGAAGCAATAAATACTACGCAGACTCCGTGAAG GGCCGATTCACCATCTCCAGAGACAATTCCAAG AACACGCTGTATCTGCAAATGAACAGCCTGAGA GCTGAGGACACGGCTGTGTATTACTGTGCGAGA GAGGATAATACGCGATATTTTGAAGAACCGAACT ACTACGGTATGGACGTCTGGGGCCAAGGGACC ACGGTCACCGTCTCCTCA (SEQ ID NO: 230) |
| HAL 7-2 | QVQLVQSGAEVKKPGSSVK VSCKASGGTFSSYAISWVR QAPGQGLEWMGGIIPIFGTA NYAQKFQGRVTITADESTST AYMELSSLRSEDTAVYYCA RDRNSYYEEPMYYFDYWG QGTLVTVSS (SEQ ID NO: 214) | CAGGTCCAGCTGGTGCAGTCTGGGGCTGAGGT GAAGAAGCCTGGGTCCTCGGTGAAGGTCTCCT GCAAGGCTTCTGGAGGCACCTTCAGCAGCTAT GCTATCAGCTGGGTGCGACAGGCCCCTGGACA AGGGCTTGAGTGGATGGGAGGGATCATCCCTAT CTTTGGTACAGCAAACTACGCACAGAAGTTCCA GGGCAGAGTCACGATTACCGCGGACGAATCCA CGAGCACAGCCTACATGGAGCTGAGCAGCCTG AGATCTGAGGACACGGCCGTGTATTACTGTGCG AGAGATCGTAATAGCTACTACGAGGAGCCAATG TACTACTTTGACTACTGGGGCCAGGGAACCCTG GTCACCGTCTCCTCA (SEQ ID NO: 231) |
| HAL 7-5 | QVQLVQSGAEVKKPGASVK VSCKASGGTFSSYAISWVR QAPGQGLEWMGGIIPIFGTA NYAQKFQGRVTITADESTST AYMELSSLRSEDTAVYYCA RDRNSYYEEPMYYFDYWG QGTLVTVSS (SEQ ID NO: 215) | CAGGTTCAGCTGGTGCAGTCTGGAGCTGAGGT GAAGAAGCCTGGGGCCTCAGTGAAGGTCTCCT GCAAGGCTTCTGGAGGCACCTTCAGCAGCTAT GCTATCAGCTGGGTGCGACAGGCCCCTGGACA AGGGCTTGAGTGGATGGGAGGGATCATCCCTAT CTTTGGTACAGCAAACTACGCACAGAAGTTCCA GGGCAGAGTCACGATTACCGCGGACGAATCCA CGAGCACAGCCTACATGGAGCTGAGCAGCCTG AGATCTGAGGACACGGCCGTGTATTACTGTGCG AGAGATCGTAATAGCTACTACGAGGAGCCAATG TACTACTTTGACTACTGGGGCCAGGGAACCCTG GTCACCGTCTCCTCA (SEQ ID NO: 232) |
| HAL 7-7 | QVQLVESGGGVVQPGRSL RLSCAASGFTFSSYGMHW VRQAPGKGLEWVAVISYDG SNKYYADSVKGRFTISRDN SKNTLYLQMNSLRAEDTAV YYCARDLVADDYGDYGTVD YWGQGTLVTVSS (SEQ ID NO: 216) | CAGGTGCAGCTGGTGGAGTCTGGGGGAGGCG TGGTCCAGCCTGGGAGGTCCCTGAGACTCTCC TGTGCAGCCTCTGGATTCACCTTCAGTAGCTAT GGCATGCACTGGGTCCGCCAGGCTCCAGGCAA GGGGCTGGAGTGGGTGGCAGTTATATCATATGA TGGAAGTAATAAATACTATGCAGACTCCGTGAAG GGCCGATTCACCATCTCCAGAGACAATTCCAAG AACACGCTGTATCTGCAAATGAACAGCCTGAGA GCTGAGGACACGGCTGTGTATTACTGTGCGAGA GATCTCGTCGCCGATGACTACGGTGACTACGG GACCGTTGACTACTGGGGCCAGGGAACCCTGG TCACCGTCTCCTCA (SEQ ID NO: 233) |
| HAL 7-12 | QLQLQESGGGLVQPGGSL RLSCAASGFTFSSYAMSWV RQAPGKGLEWVSAISGSG GSTYYADSVEGRFTISRDN SKNTLYLQMNSLRAEDTAV YYCAKERLEEPGFFDYWG QGTLVTVSS (SEQ ID NO: 217) | CAGCTGCAGCTTCAGGAGTCGGGGGGAGGCTT GGTACAGCCTGGGGGGTCCCTGAGACTCTCCT GTGCAGCCTCTGGATTCACCTTTAGCAGCTATG CCATGAGCTGGGTCCGCCAGGCTCCAGGGAAG GGGCTGGAGTGGGTCTCAGCTATTAGTGGTAGT GGTGGTAGCACATACTACGCAGACTCCGTGGA GGGCCGGTTCACCATCTCCAGAGACAATTCCAA GAACACGCTGTATCTGCAAATGAACAGCCTGAG AGCCGAGGACACGGCCGTATATTACTGTGCGAA AGAGAGGCTTGAGGAGCCCGGTTTCTTTGATTA CTGGGGCCAGGGAACCCTGGTCACCGTCTCCT CA (SEQ ID NO: 234) |
| HAL 8-7 | EVQLVETGGGLVQPGGSLR LSCAASGFTFSSYAMSWVR QAPGKGLEWVSAISGSGG | GAGGTGCAGCTGGTGGAGACTGGGGGAGGCT TGGTACAGCCTGGGGGGTCCCTGAGACTCTCC TGTGCAGCCTCTGGATTCACCTTTAGCAGCTAT |

TABLE 7 -continued

| Heavy Chain Variable Region | | |
|---|---|---|
| Antibody | Amino acid sequence | Coding DNA sequence |
| | STYYADSVKGRFTISRDNSK NTLYLQMNSLRAEDTAVYY CARGGGYSYGYEEPYYYY GMDVWGQGTTVTVSS (SEQ ID NO: 218) | GCCATGAGCTGGGTCCGCCAGGCTCCAGGGAA GGGGCTGGAGTGGGTCTCAGCTATTAGTGGTA GTGGTGGTAGCACATACTACGCAGACTCCGTGA AGGGCCGGTTCACCATCTCCAGAGACAATTCCA AGAACACGCTGTATCTGCAAATGAACAGCCTGA GAGCCGAGGACACGGCTGTGTATTACTGTGCG AGAGGGGGTGGATACAGCTATGGTTACGAGGA ACCCTACTACTACTACGGTATGGACGTCTGGGG CCAAGGGACCACGGTCACCGTCTCCTCA (SEQ ID NO: 235) |

TABLE 8

| Light Chain Variable Region | | |
|---|---|---|
| Antibody | Amino acid sequence | Coding DNA sequence |
| EW01 | QSVLTQPPSASGTPGQ RVTISCSGSSSNIGNNSV YWYQQLPGTAPKLLIYS DSQRPSGVPDRFSGSK SGTSASLAISGLRSEDEA DYYCGTWDYSLNGYVF GGGTKLTVLG (SEQ ID NO: 236) | CAGTCTGTGCTGACTCAGCCACCCTCAGCGTCTG GGACCCCCGGGCAGAGGGTCACCATCTCTTGTAG TGGCTCTTCATCTAATATTGGCAATAATTCTGTCTA CTGGTACCAGCAGCTCCCAGGAACGGCCCCCAAA CTCCTCATCTATTCTGATAGTCAGCGGCCAAGCGG GGTCCCTGACCGATTCTCTGGCTCCAAGTCTGGC ACCTCAGCCTCCCTGGCCATCAGTGGGCTCCGGT CCGAGGATGAGGCTGATTATTACTGTGGTACTTGG GATTATAGCCTGAATGGTTATGTCTTCGGCGGAGG CACCAAGCTTACGGTCCTAGGC (SEQ ID NO: 253) |
| EW02 | QSVLTQPPSASGTPGQR VTISCSGSSSNIGNNYVY WYQQLPGTAPKLLIYAN NQRPSGVPDRFSGSKS GTSASLAISGLRSEDEA DYYCGAWDDSLSGYVF GGGTKLTVLG (SEQ ID NO: 237) | CAGTCTGTGCTGACTCAGCCACCCTCAGCGTCTG GGACCCCCGGGCAGAGGGTCACCATCTCTTGTAG TGGCTCTTCATCTAATATTGGCAATAATTATGTCTAC TGGTACCAGCAGCTCCCAGGAACGGCCCCCAAAC TCCTCATCTATGCTAATAATCAGCGGCCAAGCGGG GTCCCTGACCGATTCTCTGGCTCCAAGTCTGGCAC CTCAGCCTCCCTGGCCATCAGTGGGCTCCGGTCC GAGGATGAGGCTGATTATTACTGTGGTGCTTGGGA TGATAGCCTGAGTGGTTATGTCTTCGGCGGAGGCA CCAAGCTGACGGTCCTAGGC (SEQ ID NO: 254) |
| EW03 | QSVLTQPPSASGTPGQR VTISCSGSSSNIGNNDVT WYQQLPGTAPKLLIYSD SNRPSGVPDRFSGSKS GTSASLAISGLRSEDEA DYYCGTWDSSLSAYVF GGGTKLTVLG (SEQ ID NO: 238) | CAGTCTGTGCTGACTCAGCCACCCTCAGCGTCTG GGACCCCCGGGCAGAGGGTCACCATCTCTTGTAG TGGCTCTTCATCTAATATTGGCAATAATGATGTCACC TGGTACCAGCAGCTCCCAGGAACGGCCCCCAAAC TCCTCATCTATTCTGATAGTAATCGGCCAAGCGGGG TCCCTGACCGATTCTCTGGCTCCAAGTCTGGCACC TCAGCCTCCCTGGCCATCAGTGGGCTCCGGTCCG AGGATGAGGCTGATTATTACTGTGGTACTTGGGATT CTAGCCTGAGTGCTTATGTCTTCGGCGGAGGCACC AAGCTGACGGTCCTAGGC (SEQ ID NO: 255) |
| EW06 | QSVLTQPPSASGTPGQR VTISCTGSSSNIGSNNVT WYQQLPGTAPKLLIYSN SHRPSGVPDRFSGSKS GTSASLAISGLRSEDGA DYYCGTWDDSLNGYVF GGGTKLTVLG (SEQ ID NO: 239) | CAGTCTGTGCTGACTCAGCCACCCTCAGCGTCTG GGACCCCCGGGCAGAGGGTCACCATCTCTTGTAC TGGCTCTTCATCTAATATTGGCAGTAATAATGTCACC TGGTACCAGCAGCTCCCAGGAACGGCCCCCAAAC TCCTCATCTATTCTAATAGTCATCGGCCAAGCGGGG TCCCTGACCGATTCTCTGGCTCCAAGTCTGGCACC TCAGCCTCCCTGGCCATCAGTGGGCTCCGGTCCG AGGATGGGGCTGATTATTACTGTGGTACTTGGGAT GATAGCCTGAATGGTTATGTCTTCGGCGGAGGCAC CAAGCTGACGGTCCTAGGC (SEQ ID NO: 256) |
| EW09 | QSVLTQPPSASGTPGQR VTISCSGSSSNIGNNSVN WYQQLPGTAPKLLIYAN NNRPSGVPDRFSGSKS GTSASLAISGLRSEDEA DYYCGAWDASLNGYVF GGGTKLTVLG (SEQ ID NO: 240) | CAGTCTGTGCTGACTCAGCCACCCTCAGCGTCTG GGACCCCCGGGCAGAGGGTCACCATCTCTTGTAG TGGCTCTTCATCTAATATTGGCAATAATTCTGTCAAC TGGTACCAGCAGCTCCCAGGAACGGCCCCCAAAC TCCTCATCTATGCTAATAATCAGCGGCCAAGCGGGG TCCCTGACCGATTCTCTGGCTCCAAGTCTGGCACC TCAGCCTCCCTGGCCATCAGTGGGCTCCGGTCCG AGGATGAGGCTGATTATTACTGTGGTGCTTGGGAT GCTAGCCTGAATGGTTATGTCTTCGGCGGAGGCAC CAAGCTGACGGTCCTAGGC (SEQ ID NO: 257) |

TABLE 8 -continued

Light Chain Variable Region

| Antibody | Amino acid sequence | Coding DNA sequence |
|---|---|---|
| EW10 | QSVLTQPPSASGTPGQ RVTISCTGSSSNIGSNYV SWYRQLPGTAPKLLIYS DSNRPSGVPDRFSGSK SGTSASLAISGLRSEDEA DYYCATWDASLSAYVFG GGTKLTVLG (SEQ ID NO: 241) | CAGTCTGTGCTGACTCAGCCACCCTCAGCGTCTG GGACCCCCGGGCAGAGGGTCACCATCTCTTGTAC TGGCTCTTCATCTAATATTGGCAGTAATTATGTCTCC TGGTACCGGCAGCTCCCAGGAACGGCCCCCAAAC TCCTCATCTATTCTGATAGTAATCGGCCAAGCGGGG TCCCTGACCGATTCTCTGGCTCCAAGTCTGGCACC TCAGCCTCCCTGGCCATCAGTGGGCTCCGGTCCG AGGATGAGGCTGATTATTACTGTGCTACTTGGGATG CTAGCCTGAGTGCTTATGTCTTCGGCGGAGGCACC AAGCTGACGGTCCTAGGC (SEQ ID NO: 258) |
| EW16 | QSVLTQPPSASGTPGQR VTISCTGSSSNIGNNDVY WYQQLPGTAPKLLIYSD SNRPSGIPDRFSGSKSG TSASLAISGLRSEDEADY YCGTWDDSLNGYVFGG GTKLTVLG (SEQ ID NO: 242) | CAGTCTGTGCTGACTCAGCCACCCTCAGCGTCTG GGACCCCCGGGCAGAGGGTCACCATCTCTTGTAC TGGCTCTTCATCTAATATTGGCAATAATGATGTCTAC TGGTACCAGCAGCTCCCAGGAACGGCACCCAAAC TCCTCATCTATTCTGATAGTAATCGGCCAAGCGGGA TCCCTGACCGATTCTCTGGCTCCAAGTCTGGCACC TCAGCCTCCCTGGCCATCAGTGGGCTCCGGTCCG AGGATGAGGCTGATTATTACTGTGGTACTTGGGATG ATAGCCTGAATGGTTATGTCTTCGGCGGAGGCACC AAGCTGACGGTCCTAGGC (SEQ ID NO: 259) |
| EW26 | QSVLTQPPSASGTPGQR VTISCTGSSSNIGSNSVS WYQQLPGTAPKLLIYDD SNRPSGVPDRFSGSKS GTSASLAISGLRSEDEA DYYCASWDYSLNAYVF GGGTKLTVLG (SEQ ID NO: 243) | CAGTCTGTGCTGACTCAGCCACCCTCAGCGTCTG GGACCCCCGGGCAGAGGGTCACCATCTCTTGTAC TGGCTCTTCATCTAATATTGGCAGTAATTCTGTCTC CTGGTACCAGCAGCTCCCAGGAACGGCCCCCAAA CTCCTCATCTATGATGATAGTAATCGGCCAAGCGGG GTCCCTGACCGATTCTCTGGCTCCAAGTCTGGCAC CTCAGCCTCCCTGGCCATCAGTGGGCTCCGGTCC GAGGATGAGGCTGATTATTACTGTGCTTCTTGGGAT TATAGCCTGAATGCTTATGTCTTCGGCGGAGGCAC CAAGCTGACGGTCCTAGGC (SEQ ID NO: 260) |
| EW28 | QSVLTQPPSASGTPGQR VTISCSGSSSNIGSNDVY WYQQLPGTAPKLLIYSD NNRPSGVPDRFSGSKS GTSASLAISGLRSEDEA DYYCGAWDDSLSGYVF GGGTKLTVLG (SEQ ID NO: 244) | CAGTCTGTGCTGACTCAGCCACCCTCAGCGTCTG GGACCCCCGGGCAGAGGGTCACCATCTCTTGTAG TGGCTCTTCATCTAATATTGGCAGTAATGATGTCTAC TGGTACCAGCAGCTCCCAGGAACGGCCCCCAAAC TCCTCATCTATTCTGATAATAATCGGCCAAGCGGGG TCCCTGACCGATTCTCTGGCTCCAAGTCTGGCACC TCAGCCTCCCTGGCCATCAGTGGGCTCCGGTCCG AGGATGAGGCTGATTATTACTGTGGTGCTTGGGAT GATAGCCTGAGTGGTTATGTCTTCGGCGGAGGCAC CAAGCTGACGGTCCTAGGC (SEQ ID NO: 261) |
| EW34 | QSVLTQPPSASGTPGQR VTISCTGSSSNIGSNNVN WYQQLPGTAPKLLIYAD SQRPSGVPDRFSGPKS GTSASLAISGLRSEDEA DYYCGSWDSSLSGYVL GGGTKLTVLG (SEQ ID NO: 245) | CAGTCTGTGCTGACTCAGCCACCCTCAGCGTCTG GGACCCCCGGGCAGAGGGTCACCATCTCTTGTAC TGGCTCTTCATCTAATATTGGCAGTAATAATGTCAAC TGGTACCAGCAGCTCCCAGGAACGGCCCCCAAAC TCCTCATCTATGCTGATAGTCAGCGGCCAAGCGGG GTCCCTGACCGATTCTCTGGCCCCAAGTCTGGCA CCTCAGCCTCCCTGGCCATCAGTGGGCTCCGGTC CGAGGATGAGGCTGATTATTACTGTGGTTCTTGGG ATTCTAGCCTGAGTGGTTATGTCTTAGGCGGAGGC ACCAAGCTGACGGTCCTAGGC (SEQ ID NO: 262) |
| EW37 | QSVLTQPPSASGTPGQR VTISCSGSSSNIGSNSVN WYQQLPGTAPKLLIYSD SHRPSGVPDRFSGSKS GTSASLAISGLRSEDEA DYYCGSWDDSLSGYVF GGGTKLTVLG (SEQ ID NO: 246) | CAGTCTGTGCTGACTCAGCCACCCTCAGCGTCTG GGACCCCCGGGCAGAGGGTCACCATCTCTTGTAG TGGCTCTTCATCTAATATTGGCAGTAATTCTGTCAA CTGGTACCAGCAGCTCCCAGGAACGGCCCCCAAA CTCCTCATCTATTCTGATAGTCATCGGCCAAGCGG GGTCCCTGACCGATTCTCTGGCTCCAAGTCTGGCA CCTCAGCCTCCCTGGCCATCAGTGGGCTCCGGTC CGAGGATGAGGCTGATTATTACTGTGGTTCTTGGG ATGATAGCCTGAGTGGTTATGTCTTCGGCGGAGGC ACCAAGCTGACGGTCCTAGGC (SEQ ID NO: 263) |
| HAL7-1 | QAVLTQPPSVSGAPGQR VTISCTGSSSNIGAAYEV HWYQQLPGTAPKLLIYD TSNRPSGVPDRFSGSKS GTSASLAISGLQSEDEAL YYCAAWDDSLNGPVFR RRDKLTVLG (SEQ ID NO: 247) | CAGGCTGTGCTGACTCAGCCACCCTCAGTGTCTG GGGCCCCAGGGCAGAGGGTCACCATCCCTGCAC TGGGAGCAGCTCCAACATCGGGGCAGCTTATGAG GTGCATTGGTATCAGCAGCTTCCAGGAACAGCCCC CAAACTTCTCATTTATGATACTTCCAATCGGCCCTC AGGGGTCCCTGACCGATTCTCTGGCTCCAAGTCT GGCACCTCAGCCTCCCTGGCCATCAGTGGGCTCC AGTCTGAGGATGAGGCTCTTTATTACTGTGCAGCAT |

TABLE 8 -continued

Light Chain Variable Region

| Antibody | Amino acid sequence | Coding DNA sequence |
|---|---|---|
| | | GGGATGACAGCCTGAATGGTCCGGTCTTTCGGCG GAGGGACAAGCTGACCGTCCTAGGT (SEQ ID NO: 264) |
| HAL 7-2 | QAGLTQPPSVSVSPGQT ASITCSGDKLGDRYVFW YQQKPGQAPVLVVHDD SDRPSGIPERFSGSNSG DTATLTISRVEAGDEADY YCQVWDSVNDHPVFGG GTKLTVLG (SEQ ID NO: 248) | CAGGCAGGGCTGACTCAGCCACCCTCAGTGTCCG TGTCCCCAGGACAAACAGCCAGCATAACCTGCTCT GGAGATAAATTGGGGGATAGATATGTTTTCTGGTAT CAGCAGAAGCCAGGCCAGGCCCCTGTGCTGGTC GTCCATGATGATAGCGACCGGCCCTCAGGGATCCC TGAGCGATTCTCTGGCTCCAACTCTGGGGACACG GCCACCCTGACCATCAGCAGGGTCGAGGCCGGG GATGAGGCCGACTATTACTGTCAGGTGTGGGATAG TGTTAATGATCATCCGGTGTTCGGCGGAGGGACCA AGCTGACCGTCCTAGGT (SEQ ID NO: 265) |
| HAL 7-5 | QLVLTQSSSASGTPGQR VTISCSGSGSNIGSNAVN WYQQLPGAAPKLLIHSN NQRPSGVPDRFSGSKS GTSASLAISGPQSEDEA DYYCAAWDDSLNGVVF GGGTKLTVLG (SEQ ID NO: 249) | CAGCTTGTGCTGACTCAATCATCGTCAGCGTCTGG GACCCCCGGGCAGAGGGTCACCATCTCTTGTTCT GGAAGCGGCTCCAACATCGGAAGTAATGCTGTAAA CTGGTACCAGCAGCTCCCAGGAGCGGCCCCCAAA CTCCTCATCCATAGTAATAATCAGCGGCCCTCAGG GGTCCCTGACCGATTCTCTGGCTCCAAGTCTGGCA CGTCAGCCTCCCTGGCCATCAGTGGGCCCCAGTC AGAGGATGAGGCTGACTATTACTGTGCAGCTTGGG ATGACAGTTTGAATGGTGTGGTTTTCGGCGGAGGG ACCAAGCTGACCGTCCTCGGT (SEQ ID NO: 266) |
| HAL 7-7 | QSVLTQPPSVSMAPGQT ARITCGGNNIATKGVHW YQQKAGQAPVLVVYDD SGRPSGIPDRFSGSKSG NTATLTISRVEAGDEADY YCQLWDGRSDQVLFGG GTKLTVLG (SEQ ID NO: 250) | CAGTCTGTGCTGACTCAGCCACCCTCGGTGTCAAT GGCCCCAGGACAGACGGCCAGGATCACCTGTGG GGGAAACAACATTGCAACTAAAGGTGTGCACTGGT ACCAGCAGAAGGCAGGCCAGGCCCCTGTGCTGGT CGTCTATGATGATAGCGGCCGGCCCTCAGGGATCC CTGACCGATTCTCTGGCTCCAAGTCTGGGAACACG GCCACCCTGACCATCAGCAGGGTCGAAGCCGGGG ATGAGGCCGACTATTACTGTCAGCTGTGGGATGGT AGGAGTGATCAAGTGCTATTCGGCGGAGGGACCA AGCTGACCGTCCTAGGT (SEQ ID NO: 267) |
| HAL 7-12 | QSALTQPASVSGSPGQS ITISCTGTSSDVGGYNYV SWYQQHPGKAPKLMIYE VSNRPSGVSNRFSGSK SGNTASLTISGLQAEDEA HYYCSSYTTDNAWVFG GGTQLTVLG (SEQ ID NO: 251) | CAGTCTGCCCTGACTCAGCCTGCCTCCGTGTCTG GGTCTCCTGGACAGTCGATCACCATCTCCTGCACT GGAACCAGCAGTGACGTTGGTGGTTATAACTATGT CTCCTGGTACCAACAGCACCCAGGCAAAGCCCCC AAACTCATGATTTATGAGGTCAGTAATCGGCCCTCA GGGGTTTCTAATCGCTTCTCTGGCTCCAAGTCTGG CAACACGGCCTCCCTGACCATCTCTGGGCTCCAG GCTGAGGACGAGGCTCATTATTATTGCAGCTCATAT ACAACCGACAACGCTTGGGTGTTCGGCGGAGGGA CCCAGCTGACCGTCCTGGGT (SEQ ID NO: 268) |
| HAL 8-7 | AIQLTQSPLSLSVSAGEK VTMSCKSSQSLLNSGN QKNDLAWYQQKPGQRP KLLIYGASTRESGVPDRF TGSGSGTDFTLTISSVQA EDLAVYYCQNDHSYPLT FGAGTKLEIKR (SEQ ID NO: 252) | GCCATCCAGTTGACCCAGTCTCCACTCTCCCTAAG TGTGTCAGCAGGAGAGAAGGTCACTATGAGCTGC AAGTCCAGTCAGAGTCTGTTAAACAGTGGAAATCA AAAGAACGACTTGGCCTGGTACCAGCAGAAACCA GGGCAACGTCCTAAACTGTTGATCTACGGGGCATC CACTAGGGAATCTGGGGTCCCTGATCGCTTCACAG GCAGTGGATCTGGAACCGATTTCACTCTTACCATC AGCAGTGTGCAGGCTGAAGACCTGGCAGTTTATTA CTGTCAGAATGATCATAGTTATCCGTTAACGTTCGG TGCTGGCACCAAGCTGGAAATCAAACGT (SEQ ID NO: 269) |

TABLE 9

Heavy Chain Constant Region

| Antibody | Amino acid sequence | Coding DNA sequence |
|---|---|---|
| EW01, EW02, EW03, EW06, EW09, EW10, EW16, EW26, EW28, EW34, EW37, HAL 7-1, HAL 7-2, HAL | ASTKGPSVFPLAPSSKSTSGGTAA LGCLVKDYFPEPVTVSWNSGALT SGVHTFPAVLQSSGLYSLSSVVTV PSSSLGTQTYICNVNHKPSNTKVD KKVEPKSCDKTHTCPPCPAPELLG GPSVFLFPPKPKDTLMISRTPEVT CVVVDVSHEDPEVKFNWYVDGVE | gctagcaccaagggcccatcggtcttccccctggcaccctcctc caagagcacctctgggggcacagcggccctgggctgcctggt caaggactacttccccgaaccggtgacggtgtcgtggaactac ggcgccctgaccagcggcgtgcacaccttcccggctgtcctac agtcctcaggactctactccctcagcagcgtggtgaccgtgccc tccagcagcttgggcacccagacctacatctgcaacgtgaatc acaagcccagcaacaccaaggtggacaagaaagttgagcc |

TABLE 9 - continued

Heavy Chain Constant Region

| Antibody | Amino acid sequence | Coding DNA sequence |
|---|---|---|
| 7-5, HAL 7-7,<br>HAL 7-12,<br>HAL 8-7 | VHNAKTKPREEQYNSTYRVVSVL<br>TVLHQDWLNGKEYKCKVSNKALP<br>APIEKTISKAKGQPREPQVYTLPPS<br>REEMTKNQVSLTCLVKGFYPSDIA<br>VEWESNGQPENNYKTTPPVLDSD<br>GSFFLYSKLTVDKSRWQQGNVFS<br>CSVMHEALHNHYTQKSLSLSPGK<br>(SEQ ID NO: 270) | caaatcttgtgacaaaactcacacatgcccaccgtgcccagca<br>cctgaactcctggggggaccgtcagtcttcctcttcccccaaa<br>acccaaggacaccctcatgatctcccggacccctgaggtcac<br>atgcgtggtggtggacgtgagccacgaagaccctgaggtcaa<br>gttcaactggtacgtggacggcgtggaggtgcataatgccaag<br>acaaagccgcgggaggagcagtacaacagcacgtaccgtgt<br>ggtcagcgtcctcaccgtcctgcaccaggactggctgaatggc<br>aaggagtacaagtgcaaggtctccaacaaagccctcccagc<br>ccccatcgagaaaaccatctccaaagccaaagggcagcccc<br>gagaaccacaggtgtacaccctgcccccatcccgggaggag<br>atgaccaagaaccaggtcagcctgacctgcctggtcaaaggc<br>ttctatcccagcgacatcgccgtggagtgggagagcaatgggc<br>agccggagaacaactacaagaccacgcctcccgtgctggac<br>tccgacggctccttcttcctctacagcaagctcaccgtggacaa<br>gagcaggtggcagcaggggaacgtcttctcatgctccgtgatg<br>catgaggctctgcacaaccactacacgcagaagagcctctcc<br>ctgtctccgggtaaa (SEQ ID NO: 271) |

TABLE 10

Light Chain Constant Region

| Antibody | Amino acid sequence | Coding DNA sequence |
|---|---|---|
| EW01, EW02,<br>EW03, EW06,<br>EW09, EW10,<br>EW16, EW26,<br>EW28, EW34,<br>EW37, HAL 7-1,<br>HAL 7-2, HAL 7-5,<br>HAL 7-7, HAL 7-12, | QPKAAPSVTLFPPSSEELQANK<br>ATLVCLISDFYPGAVTVAWKAD<br>SSPVKAGVETTTPSKQSNNKY<br>AASSYLSLTPEQWKSHRSYSC<br>QVTHEGSTVEKTVAPTEC<br>(SEQ ID NO: 272) | CAGCCCAAGGCTGCCCCCTCGGTCACTC<br>TGTTCCCGCCCTCCTCTGAGGAGCTTCAA<br>GCCAACAAGGCCACACTGGTGTGTCTCAT<br>AAGTGACTTCTACCCGGGAGCCGTGACA<br>GTGGCCTGGAAGGCAGATAGCAGCCCCG<br>TCAAGGCGGGAGTGGAGACCACCACACC<br>CTCCAAACAAAGCAACAACAAGTACGCGG<br>CCAGCAGCTACCTGAGCCTGACGCCCGA<br>GCAGTGGAAGTCCCACAGAAGCTACAGC<br>TGCCAGGTCACGCATGAAGGGAGCACCG<br>TGGAGAAGACAGTGGCCCCTACAGAATG<br>T (SEQ ID NO: 273) |
| HAL 8-7 | TVAAPSVFIFPPSDEQLKSGTA<br>SVVCLLNNFYPREAKVQWKVD<br>NALQSGNSQESVTEQDSKDST<br>YSLSSTLTLSKADYEKHKVYAC<br>EVTHQGLSSPVTKSFNRGEC<br>(SEQ ID NO: 274) | ACGgtggctgcaccatctgtcttcatcttcccgccatctgatg<br>agcagttgaaatctggaactgcctctgttgtgtgcctgc<u>tgaat</u><br><u>aacttctatcccagagaggccaaagtacagtggaaggtgg</u><br>ataacgccctccaatcggagtaactcccaggagagtgtcaca<br>gagcaggacagcaaggacagcacctacagcctcagcag<br>cacccctgacgctgagcaaagcagactacgagaaacacaa<br>agtctacgcctgcgaagtcacccatcagggcctgagctcgc<br>ccgtcacaaagagcttcaacaggggagagtgt (SEQ ID NO: 275) |

Example 2: Binding Affinity of Anti-Idiotype Antibody Against Anti-c-Met Antibody The antibodies prepared in Example 1 above were produced in 293 F cells (invitrogen), purified and quantified to adjust their concentration, and then used for the following tests. The quantification of the purified antibodies was performed using a Nano-drop machine, and numerals reflecting A280/A260 absorption values were used. The quantification results were confirmed again through SDA-PAGE procedures. MaxiSorp™ flat-bottom plates (Nunc) were treated with the anti-c-Met antibody prepared in reference example 1 at a concentration of 1 μg/ml, and then reacted with a blocking solution (3% BSA, 0.05% Tween 20) at a room temperature for one hour. After blocking, the plates were washed with a PBST (0.05% Tween20 in PBS) and then treated with the anti-idiotype antibodies prepared in example 1 at 10-fold serial dilution concentrations (10 μg/ml, 1 μg/ml, 0.1 μg/ml, and 0.01 μg/ml) starting from 10 μg/ml, respectively to react at a room temperature for one hour. After the reaction was complete, the plates were washed again with a microplate washer (Biotek ELx405, PBST).

A biotinylated anti-c-Met antibody was prepared by binding the anti-c-Met antibody prepared in reference example 1 with biotin, the plates washed as described above were treated with the biotinylated anti-c-Met antibody at a concentration of 200 ng/ml to react at a room temperature for one hour. The plates were washed again with a PBST (0.05% Tween20 in PBS) to eliminate unbound biotinylated anti-c-Met antibodies, treated with HRP (horse radish peroxidase) conjugated avidin (BioLegend) which specifically binds to biotin to react at a room temperature for one hour, and then washed with a PBST (0.05% Tween20 in PBS). For color development, the plates were treated with TMB (3,3,5,5-tetramethylbenzidine) which is a HRP substrate, and absorption was measured at 450 nm.

In order to identify idiotope site-specific binding affinity, the same procedures as above were carried out using plates coated with human IgG (chromPure human IgG, Jackson ImmunoResearch) in an amount of 1 μg/ml instead of the anti-c-Met antibody.

Figure 2:
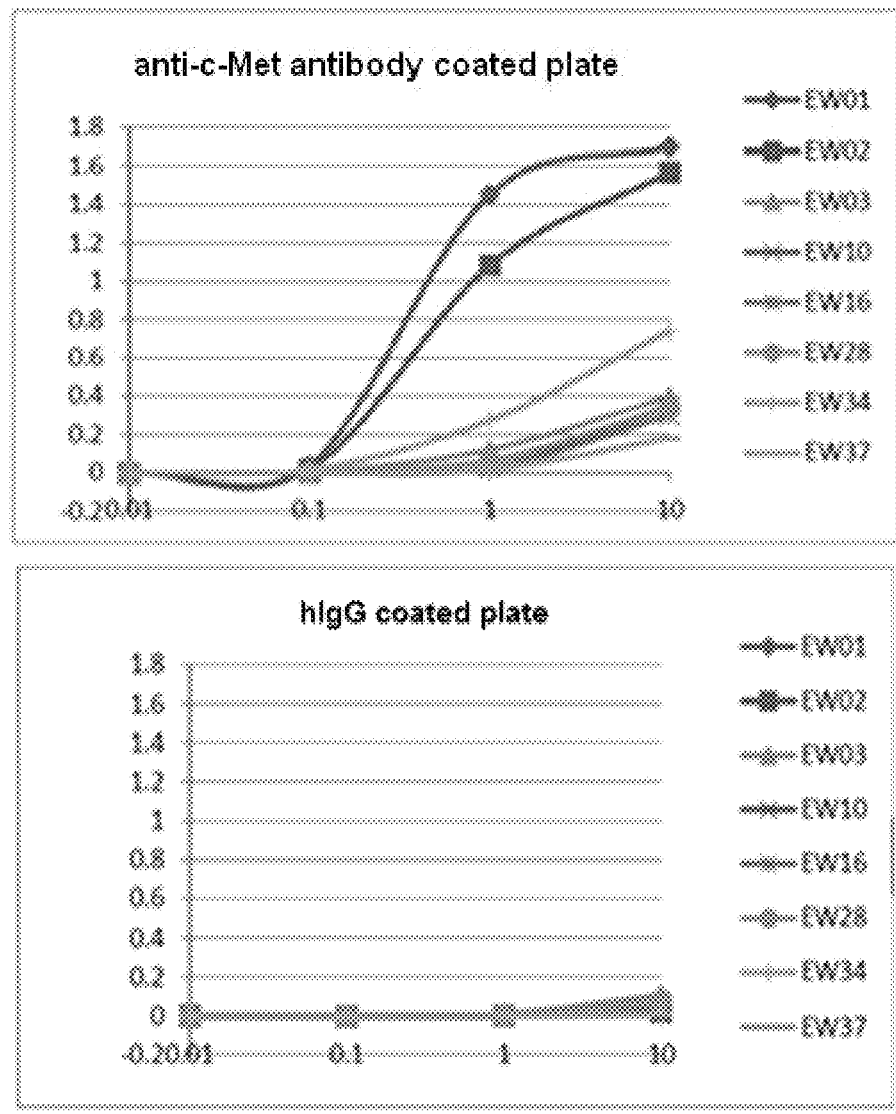
FIG. 2 is graph displaying the binding affinity of various anti-idiotype antibodies to an anti-c-Met antibody.

The results obtained are shown in FIG. 2. The Y-axis in FIG. 2 indicates a binding affinity between the anti-c-Met antibody and the anti-idiotype antibodies prepared in example 1 at 450 nm (upper), and a binding affinity between hIgG and the anti-idiotype antibodies prepared in example 1 (bottom). As seen in FIG. 2, the anti-idiotype antibodies prepared in example 1 showed higher binding affinity to the anti-c-Met antibody than hIgG. This demonstrates that the anti-idiotype antibodies prepared in example 1 bind specifically to the idiotope site of the anti-c-Met antibody.

In order to view the antigen-antibody binding affinity of an EW02 antibody, which has relatively high affinity to the anti-c-Met antibody on ELISA among the anti-idiotype antibodies, Kd value was investigated using Biacore equipment (GE healthcare) and shown in Table 11, as follows.

TABLE 11

| Antibody | $K_D$ (nM) | $K_a$ (1/Ms) | $K_d$ (1/s) |
|---|---|---|---|
| EW02 | 38.4 | $8.5 \times 10^4$ | $3.2 \times 10^{-3}$ |

The results indicate the affinity of the EW02 antibody against the anti-c-Met antibody was measured to be 38.4 nM.

Example 3: Effects on Binding Affinity of Anti-c-Met Antibody and c-Met by Anti-Idiotype Antibody The anti-c-Met antibody prepared in Reference Example 1 was bound to biotin to prepare a biotinylated anti-c-Met antibody. 200 ng/ml of the biotinylated anti-c-Met antibody was reacted with its antigen, c-Met protein (358-MT/CF, RND systems) at concentrations (2,000 ng/ml, 200 ng/ml, 20 ng/ml and 0 ng/ml) at a room temperature for one hour and then it was treated onto plates coated with the anti-idiotype antibodies prepared in the above example 1 in an amount of 1 µg/ml each to react at a room temperature for one hour. Thereafter, the plates were washed with PBST (0.05% Tween20 in PBS) to eliminate unspecific binders and then treated with Streptavidin-HRP (BioLegend) to further react at a room temperature for one hour. After the reaction was complete, the plates were further washed with a washing solution (PBST (0.05% Tween20 in PBS)), treated with a TMB substrate for color development and then, absorption was measured at 450 nm. For comparison, the same procedures as above were carried out using plates coated with 1 µg/ml of human IgG1 or 1 µg/ml of c-Met protein instead of the anti-idiotype antibodies prepared in example 1.

Figure 3:
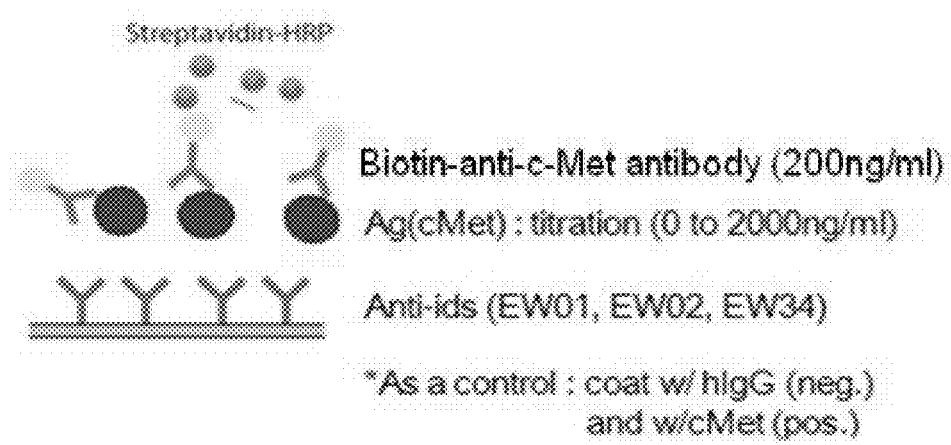
FIG. 3 is graph displaying the results of a competitive ELISA, which demonstrates that the binding sites of various anti-idiotype antibodies are idiotope sites of an anti-cMet antibody.
Figure 3:
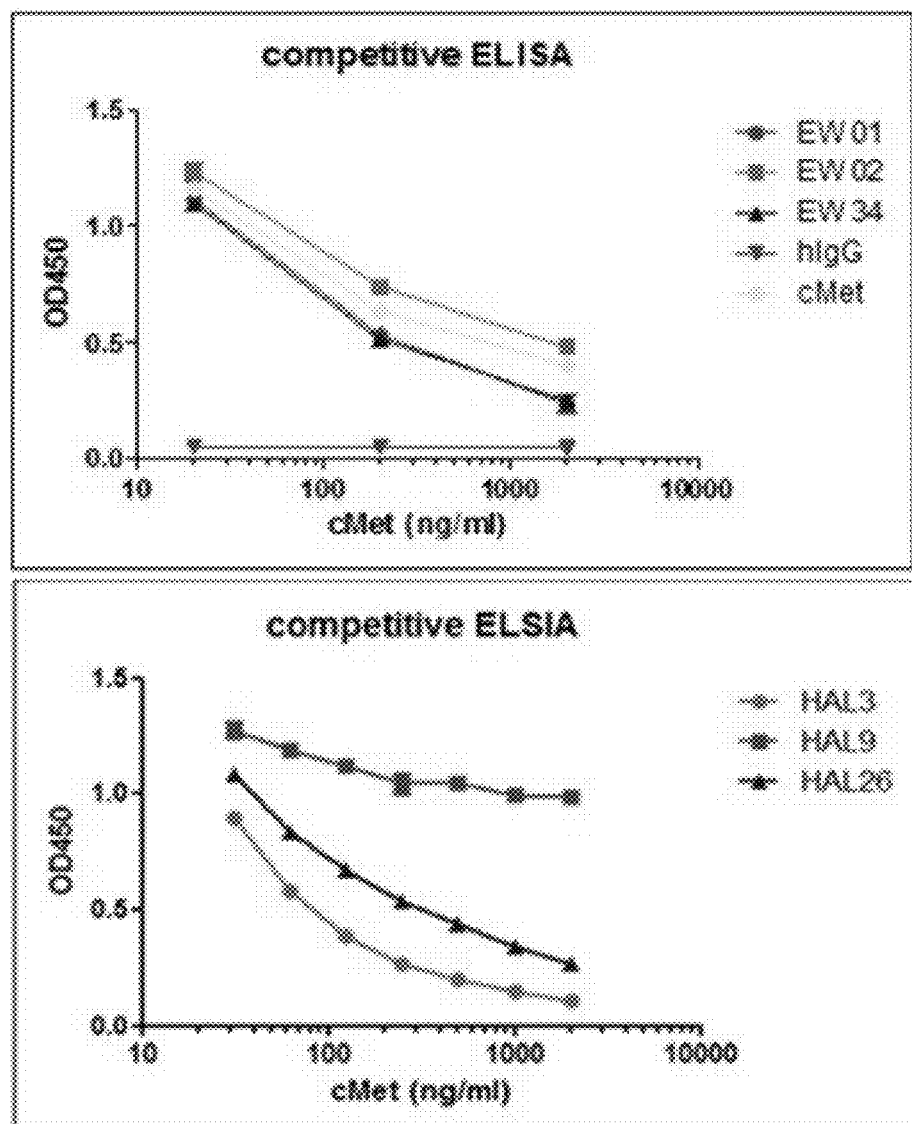

The results are shown in FIG. 3. FIG. 3 indicates that as the concentration of c-Met used in pre incubation increased, the binding between the anti-idiotype antibodies and the anti-c-Met antibody decreased in a c-Met concentration-dependent manner. Such a concentration-dependent reduction is similar to the scenario where c-Met was used instead of the anti-idiotype antibodies. Such concentration dependent reduction did not occur when human IgG was used. The results demonstrate that the anti-idiotype antibodies compete with c-Met to bind to the anti-c-Met antibody.

Example 4: Detection of Anti-c-Met Antibody Using Anti-Idiotype Antibody in Monkey Serum The EW01 antibody, which showed the most excellent binding affinity of the anti-idiotype antibodies against the anti-c-Met antibody prepared in the above example 1 (see FIG. 2), was selected for additional testing. The binding affinity of the EW01 antibody to the anti-c-Met antibody in a monkey serum was tested. This test illustrates the application of the anti-idiotype antibodies to the detection of an anti-c-Met antibody within a serum.

MaxiSorp™ flat-bottom plates (Nunc) were treated with the EW01 antibody at a concentration of 0.25 µg/ml for coating and then, they were reacted with a blocking solution (3% (w/v) BSA in PBST) at a room temperature for one hour. A 10% (v/v) serum solution (in PBS) was prepared using the serum of cynomolgus monkey and the anti-c-Met antibody prepared in reference example 1 was added thereto from 1 µg/ml to 3-fold serial dilution concentrations (from 1 µg/ml to 8-point serial dilution), respectively to prepare anti-c-Met antibody samples. The above prepared plates were treated with the thus prepared anti-c-Met antibody samples to further react at a room temperature for one hour. After the reaction was complete, the plates were washed again with a washing solution (PBST (0.05% Tween20 in PBS)), and 0.25 µg/ml of the EW01 antibody which was biotinylated for detection purpose was added thereto to react at a room temperature for one hour. After the reaction of the detection antibody was over, the same washing procedures as above were carried out, and a HRP-streptavidin solution (BioLegend) was added thereto to react at a room temperature for one hour. After all the reactions were over, the plates were finally washed and treated with a TMB substrate for color development, and absorption was measured at 450 nm and analyzed.

Figure 4:
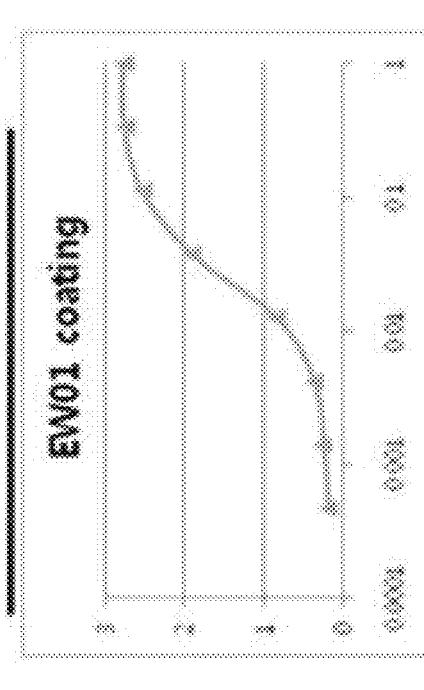
FIG. 4 is graph displaying the detection results of an anti-c-Met antibody using an anti-idiotype antibody in a monkey serum.
Figure 4:
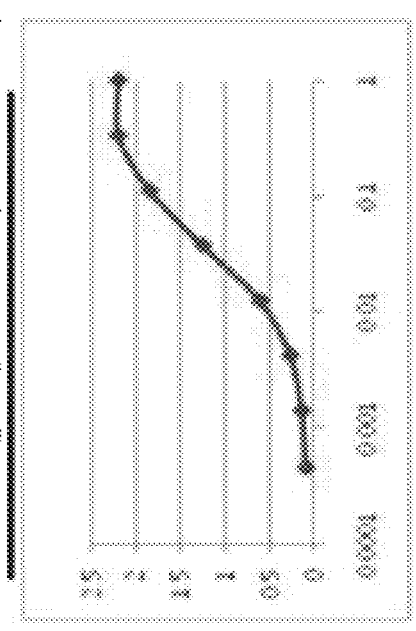

The results are shown in FIG. 4. The X-axis in FIG. 4 indicates the concentrations of the anti-c-Met antibody, and Y-axis indicates absorption values at 450 nm. The left graph shows results measured by reacting plates treated with antigen c-Met protein with an anti-c-Met antibody-containing monkey serum diluted to 0.1% (v/v) in order to measure the anti-c-Met antibody in a monkey serum according to the previous experiment method prior to using anti-idiotype antibodies. On the right, plates treated with the anti-idiotype antibodies were used in order to detect the anti-c-Met antibody in a monkey serum according to the test method improved after the anti-idiotype antibodies were developed. Even when the monkey serum was diluted to 10% (v/v) or so, results similar to those of the previous method were still obtained, which suggests that the detection limit is increased by 100 times.

Example 5: Effects on Intracellular Efficacy of Anti-c-Met Antibody by Anti-Idiotype Antibody Against c-Met Antibody An EBC1 cell line (ATCC) was prepared in an amount of $1 \times 10^4$ cell/well, which was then treated with 1 µg/ml of the anti-c-Met antibody prepared in reference example 1 and treated with the anti-idiotype antibody prepared in example 1 so that the ratios of the anti-c-Met antibody and the anti-idiotype antibody in weight became 1:2, 1:1, 2:1, and 4:1 (weight of anti-idiotype antibody:weight of anti-c-Met antibody) to culture at 37° C. for 72 hours. For comparison, the anti-c-Met antibody was treated alone or only 1 µg/ml of hIgG was treated without the anti-c-Met antibody.

After the culture, cell proliferation was analyzed using CellTiter-Glo (promega) according to the manufacturer's instructions. Particularly, the cultured cells were treated with a Cell Titer-Glo solution in an amount of 100 µl/well and reacted at a room temperature for 30 min in the state of light being shielded. The plates where color development by CellTiter-Glo was complete were analyzed for apoptosis by measuring luminescence.

Figure 5:
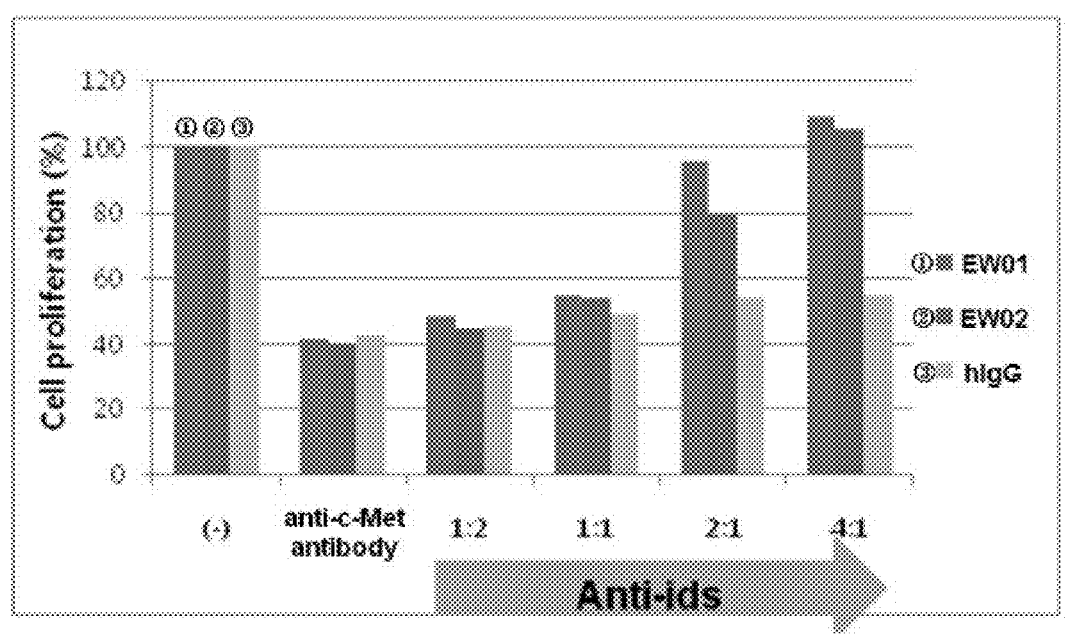
FIG. 5 is a graph displaying the neutralizing effects of an anti-idiotype antibody on anti-proliferative efficacy of an anti-cMet antibody.

The results are shown in FIG. 5. The X-axis in FIG. 5 indicates the weight ratios of the anti-idiotype antibody and the anti-c-Met antibody (weight of anti-idiotype antibody: weight of anti-c-Met antibody). When compared to the very left no-treatment group, cell proliferation when treated with the anti-c-Met antibody was reduced by 60% or so, and the cell proliferation inhibitory efficacy of the anti-c-Met antibody disappeared by further reaction with the anti-idiotype antibody. As the ratios of the anti-idiotype antibody increased from left to right, the efficacy of the anti-c-Met antibody disappeared in proportion to those ratios. When the hIgG antibody was used instead of the anti-idiotype antibody for comparison, there was no reduction in efficacy.

Example 6: Detection of Anti-c-Met Antibody Using Anti-Idiotype Antibody in Human Serum In order to see whether the method for detecting an anti-c-Met antibody in a monkey serum is applicable to a human serum, the human serum was diluted to 10% (v/v) and the anti-c-Met antibody prepared in reference example 1 was prepared from a concentration of 1 µg/ml to 3-fold serial dilutions. The above prepared human serums containing the c-Met antibody were reacted to plates treated with 0.25 µg/ml of each anti-idiotype antibody (capture) prepared in example 1 at a room temperature for one hour. The plates were washed with a washing solution (0.05% Tween20 in PBS) in order to eliminate unreacted antibodies and then treated with a biotinylated form of EW01 (detector) which showed the best binding affinity out of the anti-idiotype antibodies at a concentration of 0.25 µg/ml to react at a room temperature for one hour. The plates where the reaction was over were washed with a washing solution in the same manner and then reacted with Streptavidin-HRP (BioLegend) which shows biotin-specific binding at a room temperature for one hour in the state of light being shielded. Finally, the plates were washed with a washing solution (PBST (0.05% Tween20 in PBS)) to eliminate unreacted HRP and then, they were subject to color development using a TMB substrate to measure absorption at 450 nm. The same procedures as above were carried out using plates treated with 0.25 µg/ml of hIgG instead of the anti-idiotype antibody for comparison.

Figure 6:
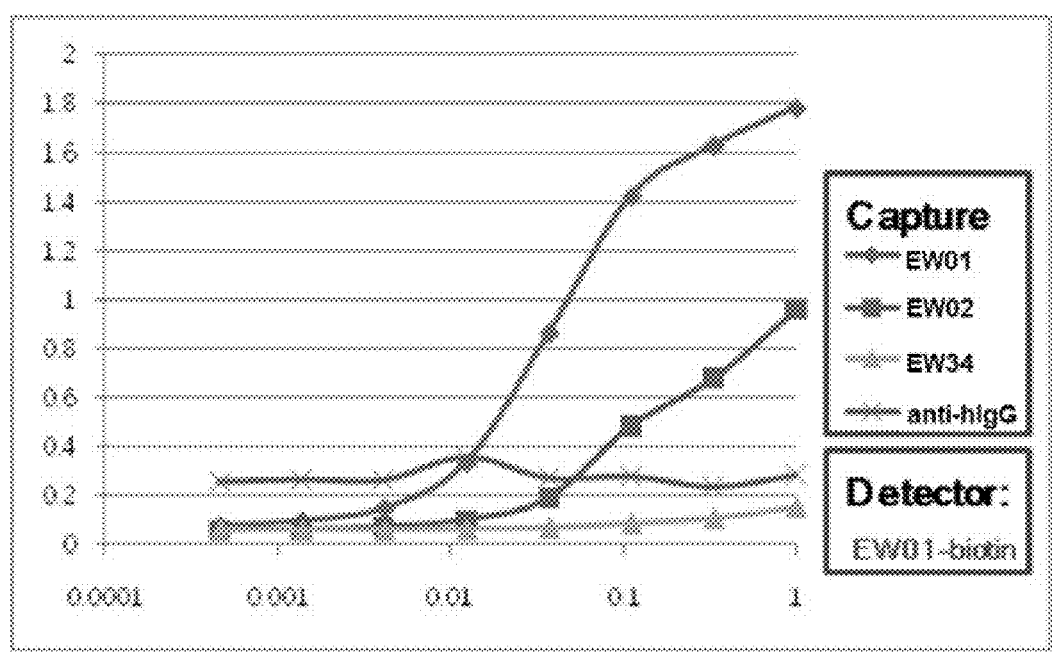
FIG. 6 is a graph displaying the detection results of an anti-c-Met antibody using an anti-idiotype antibody in a human serum.

The results are shown in FIG. 6. The X-axis in FIG. 6 indicates the concentrations of the anti-c-Met antibody and Y-axis indicates absorption values at 450 nm. From the results of FIG. 6, it was confirmed that the anti-idiotype antibodies of the present invention are applicable to not only a monkey serum but also a human serum.

Example 7: Quantification of Anti-Drug Antibody (ADA) in Anti-c-Met Antibody Treated Monkey Serum The presence or absence and the amount of ADA against anti-c-Met antibody in anti-c-Met antibody treated monkey serum (Equitech) were determined by using an anti-idiotype antibody. Assuming that anti-idiotype antibodies from example 1 are examples of ADAs against anti-c-Met antibody, 100 µg/mL of each anti-idiotype antibody was pooled in normal monkey serum (Equitech) replacing ADA against anti-c-Met antibody.

MaxiSorp™ flat-bottom plate (Nunc) was coated with 1 µ/ml of the anti-c-Met antibody prepared in Reference Example 1 and blocked with blocking solution (1% BSA in PBST) at room temperature for 1 hour. As a standard sample, anti-idiotype antibody EW01 prepared in Example 1 was provided by 3-fold serial dilution starting from 10 µg/ml. As a test sample, anti-idiotype antibodies treated monkey serum was prepared by treating 4 types of anti-idiotype antibodies of Example 1 at the total concentration of 400 µg/mL, wherein each of the anti-idiotype antibodies was treated at the concentration of 100 µg/mL. The monkey serum sample was diluted 1/10, 1/50, or 1/100 times by volume using PBST.

The standard sample (anti-idiotype antibody EW01) and the test sample (anti idiotype antibody treated monkey serum) were respectively added to the blocked plate and reacted for 1 hour. The non-reacted materials were removed with washing solution (PBST (0.05% Tween20 in PBS)). To make a detection, 0.5 µg/ml of biotinylated anti-c-Met antibody was added to the plate, reacted for 1 hours, and then washed with washing solution (PBST (0.05% Tween20 in PBS)) to remove the non-reacted materials.

The washed plate was reacted with Streptavidin-HRP (BioLegend), which specifically binds to biotin, at room temperature for 1 hour with blocking light. Finally, the plate was washed with washing solution (PBST (0.05% Tween20 in PBS)) to remove the non-reacted materials. TMB substrate was used for a coloring reaction and the absorbance was measured at 450 nm using SpectraMax.

Figure 8:
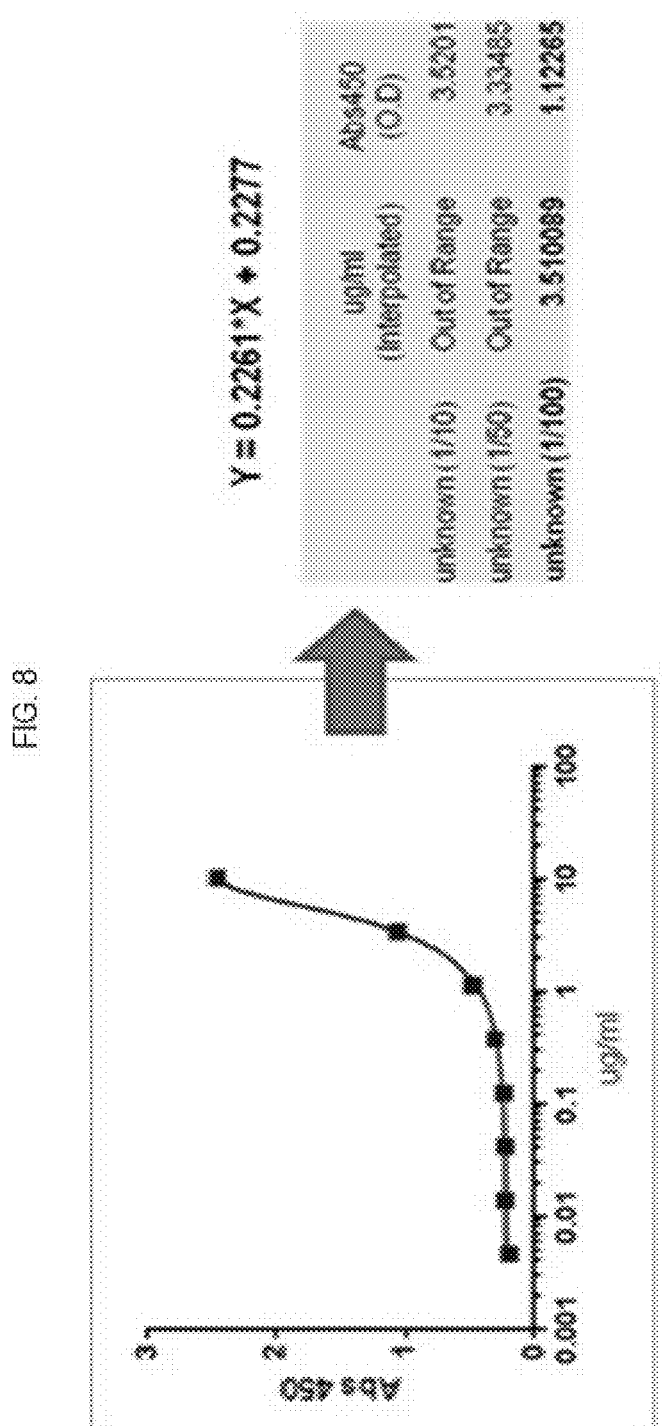
FIG. 8 is a graph displaying a standard curve of absorbance measured from a standard sample comprising anti-idiotype antibody EW01, according to various concentrations.

The absorbance measured from the standard sample according to the concentrations of the anti-idiotype antibody EW01 was shown in FIG. 8. The absorbance measured form the test sample (monkey serum of 1/100 dilution) was 1.12 (the absorbance of the test samples of 1/10 and 1/50 dilutions was out of the standard sample's range in this experimentation). The concentration of ADA in the test sample can be calculated from absorbance value 1.12 by applying the formula shown in FIG. 8 The formula was obtained from softmax program (5-PL) in SpectraMax machine. The calculated value was 3.5 µg/ml, indicating that considering the dilution fold, the concentration of the ADA present in the test sample is 350 µg/ml. This value was similar with initial amount of the anti-idiotype antibodies which were initially added into the test sample.

As described above, the amount as well as the presence/absence of ADA in a test sample can be determined by obtaining a standard curve of absorbance from a standard sample, establishing a formula, and then applying the absorbance value measured from the test sample to the formula.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-idiotype antibody or antigen-binding fragment thereof that specifically binds to an idiotype of an anti-c-Met antibody comprising:
   (a) a CDR-H1 comprising the amino acid sequence of SEP ID NO: 116, a CDR-H2 comprising the amino acid sequence of SEQ ID NO: 126, a CDR-H3 comprising the amino acid sequence of SEQ ID NO: 140, a CDR-L1 comprising the amino acid sequence of SEQ ID NO: 156, a CDR-L2 comprising the amino acid sequence of SEQ ID NO: 173, and a CDR-L3 comprising the amino acid sequence of SEQ ID NO: 189;
   (b) a CDR-H1 comprising the amino acid sequence of SEQ ID NO: 115, a CDR-H2 comprising the amino acid sequence of SEQ ID NO: 125, a CDR-H3 comprising the amino acid sequence of SEQ ID NO: 139, a CDR-L1 comprising the amino acid sequence of SEQ ID NO: 155, a CDR-L2 comprising the amino acid sequence of SEQ ID NO: 172, and a CDR-L3 comprising the amino acid sequence of SEQ ID NO: 188;
   (c) a CDR-H1 comprising the amino acid sequence of SEQ ID NO: 117, a CDR-H2 comprising the amino acid sequence of SEQ ID NO: 127, a CDR-H3 comprising the amino acid sequence of SEQ ID NO: 141, a CDR-L1 comprising the amino acid sequence of SEQ ID NO: 157, a CDR-L2 comprising the amino acid sequence of SEQ ID NO: 174, and a CDR-L3 comprising the amino acid sequence of SEQ ID NO: 190;
   (d) a CDR-H1 comprising the amino acid sequence of SEQ ID NO: 118, a CDR-H2 comprising the amino acid sequence of SEQ ID NO: 128, a CDR-H3 comprising the amino acid sequence of SEQ ID NO: 142, a CDR-L1 comprising the amino acid sequence of SEQ ID NO: 158, a CDR-L2 comprising the amino acid sequence of SEQ ID NO: 175, and a CDR-L3 comprising the amino acid sequence of SEQ ID NO: 191;
   (e) a CDR-H1 comprising the amino acid sequence of SEQ ID NO: 117, a CDR-H2 comprising the amino acid sequence of SEQ ID NO: 129, a CDR-H3 comprising the amino acid sequence of SEQ ID NO: 143, a CDR-L1 comprising the amino acid sequence of SEQ ID NO: 159, a CDR-L2 comprising the amino acid sequence of SEQ ID NO: 176, and a CDR-L3 comprising the amino acid sequence of SEQ ID NO: 192;
   (f) a CDR-H1 comprising the amino acid sequence of SEQ ID NO: 118, a CDR-H2 comprising the amino acid sequence of SEQ ID NO: 130, a CDR-H3 comprising the amino acid sequence of SEQ ID NO: 144, a CDR-L1 comprising the amino acid sequence of SEQ ID NO: 160, a CDR-L2 comprising the amino acid sequence of SEQ ID NO: 177, and a CDR-L3 comprising the amino acid sequence of SEQ ID NO: 193;
   (g) a CDR-H1 comprising the amino acid sequence of SEQ ID NO: 115, a CDR-H2 comprising the amino acid sequence of SEQ ID NO: 131, a CDR-H3 comprising the amino acid sequence of SEQ ID NO: 145, a CDR-L1 comprising the amino acid sequence of SEQ ID NO: 161, a CDR-L2 comprising the amino acid sequence of SEQ ID NO: 178, and a CDR-L3 comprising the amino acid sequence of SEQ ID NO: 191;
   (h) a CDR-H1 comprising the amino acid sequence of SEQ ID NO: 116, a CDR-H2 comprising the amino acid sequence of SEQ ID NO: 132, a CDR-H3 comprising the amino acid sequence of SEQ ID NO: 146, a CDR-L1 comprising the amino acid sequence of SEQ ID NO: 162, a CDR-L2 comprising the amino acid sequence of SEQ ID NO: 178, and a CDR-L3 comprising the amino acid sequence of SEQ ID NO: 194;

(i) a CDR-H1 comprising the amino acid sequence of SEQ ID NO: 119, a CDR-H2 comprising the amino acid sequence of SEQ ID NO: 133, a CDR-H3 comprising the amino acid sequence of SEQ ID NO: 147, a CDR-L1 comprising the amino acid sequence of SEQ ID NO: 163, a CDR-L2 comprising the amino acid sequence of SEQ ID NO: 179, and a CDR-L3 comprising the amino acid sequence of SEQ ID NO: 189;

(j) a CDR-H1 comprising the amino acid sequence of SEQ ID NO: 119, a CDR-H2 comprising the amino acid sequence of SEQ ID NO: 134, a CDR-H3 comprising the amino acid sequence of SEQ ID NO: 148, a CDR-L1 comprising the amino acid sequence of SEQ ID NO: 164, a CDR-L2 comprising the amino acid sequence of SEQ ID NO: 180, and a CDR-L3 comprising the amino acid sequence of SEQ ID NO: 195; or (k) a CDR-H1 comprising the amino acid sequence of SEQ ID NO: 120, a CDR-H2 comprising the amino acid sequence of SEQ ID NO: 126, a CDR-H3 comprising the amino acid sequence of SEQ ID NO: 149, a CDR-L1 comprising the amino acid sequence of SEQ ID NO: 165, a CDR-L2 comprising the amino acid sequence of SEQ ID NO: 181, and a CDR-L3 comprising the amino acid sequence of SEQ ID NO: 196.

2. The anti-idiotype antibody or antigen-binding fragment thereof according to claim 1, wherein the anti-idiotype antibody comprises:

a heavy chain variable region of SEQ ID NO: 202 and a light chain variable region of SEQ ID NO: 236;
a heavy chain variable region of SEQ ID NO: 203 and a light chain variable region of SEQ ID NO: 237;
a heavy chain variable region of SEQ ID NO: 204 and a light chain variable region of SEQ ID NO: 238;
a heavy chain variable region of SEQ ID NO: 205 and a light chain variable region of SEQ ID NO: 239;
a heavy chain variable region of SEQ ID NO: 206 and a light chain variable region of SEQ ID NO: 240;
a heavy chain variable region of SEQ ID NO: 207 and a light chain variable region of SEQ ID NO: 241;
a heavy chain variable region of SEQ ID NO: 208 and a light chain variable region of SEQ ID NO: 242;
a heavy chain variable region of SEQ ID NO: 209 and a light chain variable region of SEQ ID NO: 243;
a heavy chain variable region of SEQ ID NO: 210 and a light chain variable region of SEQ ID NO: 244;
a heavy chain variable region of SEQ ID NO: 211 and a light chain variable region of SEQ ID NO: 245; or
a heavy chain variable region of SEQ ID NO: 212 and a light chain variable region of SEQ ID NO: 246.

3. The anti-idiotype antibody or antigen-binding fragment thereof according to claim 1, wherein the anti-idiotype antibody is a mouse antibody, a mouse-human chimeric antibody, a humanized antibody, or a human antibody.

4. The anti-idiotype antibody or antibody fragment thereof according to claim 1, wherein the anti-idiotype antibody or antibody fragment thereof is an antigen-binding fragment selected from the group consisting of scFv, $(scFv)_2$, Fab, Fab', and $F(ab')_2$.

5. A composition comprising an anti-idiotype antibody or antigen-binding fragment thereof according to claim 1 and a carrier.

6. A method for detecting an anti-c-Met antibody comprising:
contacting a biological sample with an anti-idiotype antibody or antigen-binding fragment thereof according to claim 1; and
determining the presence or absence of an antigen-antibody reaction.

7. The method according to claim 6, wherein the biological sample comprises serum isolated from a subject.

8. A method for analyzing an anti-drug antibody, the method comprising measuring the absorption of a serum isolated from a patient to whom a test drug has been intravenously administered; and
comparing the obtained absorption results with the absorption change of the anti-idiotype antibody or antigen-binding fragment thereof according to claim 1 in a serum isolated from a patient to whom an anti-c-Met antibody has been administered.

9. The anti-idiotype antibody or antigen-binding fragment thereof of claim 1, wherein the anti-idiotype antibody or antigen-binding fragment thereof has an affinity ($K_d$) to an anti-c-Met antibody or antibody fragment of about 50 nM or less.

* * * * *

```
                         SEQUENCE LISTING

<160> NUMBER OF SEQ ID NOS: 276

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
 1               5                  10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4
```

```
Xaa Xaa Tyr Tyr Met Ser
  1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: X is Asn or Thr

<400> SEQUENCE: 5

Arg Asn Xaa Xaa Asn Gly Xaa Thr
  1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
  1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn
<220> FEATURE:
<221> NAME/KEY: MOD_RES
<222> LOCATION: (9)
<223> OTHER INFORMATION: Xaa is Ser or Trp

<400> SEQUENCE: 7

Lys Ser Ser Xaa Ser Leu Leu Ala Xaa Gly Asn Xaa Xaa Asn Tyr Leu
  1               5                  10                  15

Ala

<210> SEQ ID NO 8
```

```
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
  1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: X is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
  1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
  1               5                  10                  15
Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
  1               5

<210> SEQ ID NO 12
<211> LENGTH: 9
```

```
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
  1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
  1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
  1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
  1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
  1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody (huAbF46-H4)

<400> SEQUENCE: 17

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30
```

```
Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
                100                 105                 110

Val Thr Val Ser Ser
            115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody (huAbF46-H4)

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
                100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody (huAbF46-H4)

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
```

-continued

```
                 85                  90                  95

Ser Tyr Ser Arg Pro Leu Thr Phe Gly Gln Gly Thr Lys Val Glu Ile
            100                 105                 110

Lys Arg
```

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody (huAbF46-H4)

<400> SEQUENCE: 20

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95

Ser Tyr Ser His Pro Phe Ser Phe Gly Gln Gly Thr Lys Val Glu Ile
            100                 105                 110

Lys Arg
```

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody (huAbF46-H4)

<400> SEQUENCE: 21

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Phe Thr Phe Gly Gln Gly Thr Lys Val Glu Ile
            100                 105                 110

Lys Arg
```

<210> SEQ ID NO 22
<211> LENGTH: 6
<212> TYPE: PRT

```
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
 1               5

<210> SEQ ID NO 28
<211> LENGTH: 6
<212> TYPE: PRT
<213> ORGANISM: Artificial Sequence
```

```
<220> FEATURE:
<223> OTHER INFORMATION: Synthetic CDR-H3 derived from YC374 clone

<400> SEQUENCE: 28

Asp Asn Trp Leu Thr Tyr
 1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
 1               5                  10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
 1               5                  10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
 1               5                  10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
 1               5                  10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
```

-continued

```
                1               5                  10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
  1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
  1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
  1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
  1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
```

<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38

```
gaattcgccg ccaccatgga atggagctgg gttttctcg taacactttt aaatggtatc    60
cagtgtgagg tgaagctggt ggagtctgga ggaggcttgg tacagcctgg gggttctctg   120
agactctcct gtgcaacttc tgggttcacc ttcactgatt actacatgag ctgggtccgc   180
cagcctccag aaaggcact tgagtggttg ggttttatta gaaacaaagc taatggttac   240
acaacagagt acagtgcatc tgtgaagggt cggttcacca tctccagaga taattcccaa   300
agcatcctct atcttcaaat ggacaccctg agagctgagg acagtgccac ttattactgt   360
gcaagagata actggtttgc ttactggggc caagggactc tggtcactgt ctctgcagct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
tcttgtgaca aaactcacac atgcccaccg tgcccagcac ctgaactcct ggggggaccg   780
tcagtcttcc tcttccccc aaaacccaag gacaccctca tgatctcccg gacccctgag   840
gtcacatgcg tggtggtgga cgtgagccac gaagaccctg aggtcaagtt caactggtac   900
gtggacggcg tggaggtgca taatgccaag acaaagccgc gggaggagca gtacaacagc   960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcccg ggaggagatg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagagcctct ccctgtctcc gggtaaatga ctcgag                            1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)

```
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atgattcac aggcccaggt cctcatgttg      60
ctgctgctat cggtatctgg tacctgtgga cattttga tgacccagtc tccatcctcc     120
ctgactgtgt cagcaggaga aaggtcact atgagctgca agtccagtca gagtctttta    180
gctagtggca accaaaataa ctacttggcc tggcaccagc agaaaccagg acgatctcct   240
aaaatgctga taatttgggc atccactagg gtatctggag tccctgatcg cttcataggc   300
agtggatctg ggacggattt cactctgacc atcaacagtg tgcaggctga agatctggct   360
gtttattact gtcagcagtc ctacagcgct ccgctcacgt tcggtgctgg gaccaagctg   420
gagctgaaac gtacggtggc tgcaccatct gtcttcatct tcccgccatc tgatgagcag   480
ttgaaatctg gaactgcctc tgttgtgtgc ctgctgaata acttctatcc cagagaggcc   540
aaagtacagt ggaaggtgga taacgccctc caatcgggta actcccagga gagtgtcaca   600
gagcaggaca gcaaggacag cacctacagc ctcagcagca ccctgacgct gagcaaagca   660
gactacgaga aacacaaagt ctacgcctgc gaagtcaccc atcagggcct gagctcgccc   720
gtcacaaaga gcttcaacag gggagagtgt tgactcgag                          759

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
             85                  90                  95

Tyr Cys Ala Arg Asp Asn Trp Phe Ala Tyr Trp Gly Gln Gly Thr Leu
```

```
            100                 105                 110
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
```

```
                20                  25                  30
Tyr Met Ser Trp Val Arg Gln Ala Pro Gly Lys Gly Leu Glu Trp Leu
                35                  40                  45
Gly Phe Ile Arg Asn Lys Ala Asn Gly Tyr Thr Thr Glu Tyr Ser Ala
            50                  55                  60
Ser Val Lys Gly Arg Phe Thr Ile Ser Arg Asp Asn Ser Lys Asn Ser
 65                  70                  75                  80
Leu Tyr Leu Gln Met Asn Ser Leu Arg Ala Glu Asp Thr Ala Val Tyr
                85                  90                  95
Tyr Cys Ala Arg Asp Asn Trp Phe Ala Tyr Trp Gly Gln Gly Thr Leu
                100                 105                 110
Val Thr Val Ser Ser Ala Ser Thr Lys Gly Pro Ser Val Phe Pro Leu
                115                 120                 125
Ala Pro Ser Ser Lys Ser Thr Ser Gly Gly Thr Ala Ala Leu Gly Cys
                130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
                195                 200                 205
Thr Lys Val Asp Lys Lys Val Glu Pro Lys Ser Cys Asp Lys Thr His
                210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
                275                 280                 285
Thr Lys Pro Arg Glu Glu Gln Tyr Asn Ser Thr Tyr Arg Val Val Ser
                290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
                370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
                435                 440                 445
```

```
<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Thr | Asp | Tyr |
| | | | 20 | | | | | 25 | | | | | 30 | | |
| Tyr | Met | Ser | Trp | Val | Arg | Gln | Ala | Pro | Gly | Lys | Gly | Leu | Glu | Trp | Leu |
| | | 35 | | | | | 40 | | | | | 45 | | | |
| Gly | Phe | Ile | Arg | Asn | Lys | Ala | Asn | Gly | Tyr | Thr | Thr | Glu | Tyr | Ser | Ala |
| | 50 | | | | | 55 | | | | | 60 | | | | |
| Ser | Val | Lys | Gly | Arg | Phe | Thr | Ile | Ser | Arg | Asp | Asn | Ser | Lys | Asn | Thr |
| 65 | | | | | 70 | | | | | 75 | | | | | 80 |
| Leu | Tyr | Leu | Gln | Met | Asn | Ser | Leu | Arg | Ala | Glu | Asp | Thr | Ala | Val | Tyr |
| | | | | 85 | | | | | 90 | | | | | 95 | |
| Tyr | Cys | Ala | Arg | Asp | Asn | Trp | Phe | Ala | Tyr | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Lys | Val | Glu | Pro | Lys | Ser | Cys | Asp | Lys | Thr | His |
| | 210 | | | | | 215 | | | | | 220 | | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Pro | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Glu | Glu | Met | Thr | Lys | Asn | Gln | Val | Ser | Leu | Thr | Cys | Leu |
| | | 355 | | | | | 360 | | | | | 365 | | | |

```
Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Ala Ser
                 20                  25                  30

Gly Asn Gln Asn Asn Tyr Leu Ala Trp His Gln Gln Lys Pro Gly Gln
             35                  40                  45

Pro Pro Lys Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
```

```
                1               5                      10                       15
            Glu Pro Ala Ser Ile Ser Cys Lys Ser Ser Gln Ser Leu Leu Ala Ser
                            20                  25                  30
            Gly Asn Gln Asn Asn Tyr Leu Ala Trp His Leu Gln Lys Pro Gly Gln
                        35                      40                  45
            Ser Pro Gln Met Leu Ile Ile Trp Ala Ser Thr Arg Val Ser Gly Val
                    50                      55                  60
            Pro Asp Arg Phe Ser Gly Ser Gly Ser Gly Thr Asp Phe Thr Leu Lys
            65                      70                  75                      80
            Ile Ser Arg Val Glu Ala Glu Asp Val Gly Val Tyr Tyr Cys Gln Gln
                            85                  90                  95
            Ser Tyr Ser Ala Pro Leu Thr Phe Gly Gln Gly Thr Lys Leu Glu Leu
                        100                     105                 110
            Lys Arg Thr Val Ala Ala Pro Ser Val Phe Ile Phe Pro Pro Ser Asp
                        115                     120                 125
            Glu Gln Leu Lys Ser Gly Thr Ala Ser Val Val Cys Leu Leu Asn Asn
                        130                     135                 140
            Phe Tyr Pro Arg Glu Ala Lys Val Gln Trp Lys Val Asp Asn Ala Leu
            145                     150                 155                     160
            Gln Ser Gly Asn Ser Gln Glu Ser Val Thr Glu Gln Asp Ser Lys Asp
                        165                     170                 175
            Ser Thr Tyr Ser Leu Ser Ser Thr Leu Thr Leu Ser Lys Ala Asp Tyr
                        180                     185                 190
            Glu Lys His Lys Val Tyr Ala Cys Glu Val Thr His Gln Gly Leu Ser
                        195                     200                 205
            Ser Pro Val Thr Lys Ser Phe Asn Arg Gly Glu Cys
                        210                     215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
            1               5                   10                      15
            Glu Arg Ala Thr Ile Asn Cys Lys Ser Ser Gln Ser Leu Leu Ala Ser
                            20                  25                  30
            Gly Asn Gln Asn Asn Tyr Leu Ala Trp Tyr Gln Gln Lys Pro Gly Gln
                        35                      40                  45
            Pro Pro Lys Leu Leu Ile Ile Trp Ala Ser Thr Arg Val Ser Gly Val
                    50                      55                  60
            Pro Asp Arg Phe Ser Gly Ser Gly Ser Gly Thr Asp Phe Thr Leu Thr
            65                      70                  75                      80
            Ile Ser Ser Leu Gln Ala Glu Asp Val Ala Val Tyr Tyr Cys Gln Gln
                            85                  90                  95
            Ser Tyr Ser Ala Pro Leu Thr Phe Gly Gly Gly Thr Lys Val Glu Ile
                        100                     105                 110
            Lys Arg Thr Val Ala Ala Pro Ser Val Phe Ile Phe Pro Pro Ser Asp
                        115                     120                 125
            Glu Gln Leu Lys Ser Gly Thr Ala Ser Val Val Cys Leu Leu Asn Asn
                        130                     135                 140
            Phe Tyr Pro Arg Glu Ala Lys Val Gln Trp Lys Val Asp Asn Ala Leu
```

```
                145                 150                 155                 160
Gln Ser Gly Asn Ser Gln Glu Ser Val Thr Glu Gln Asp Ser Lys Asp
                    165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                    165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu
        210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47
gaggtgcagc tggtggagtc tgggggaggc ttggtccagc ctggagggtc cctgagactc    60
tcctgtgcag cctctggatt caccttcact gactactaca tgagctgggt ccgccaggct   120
```

```
ccagggaagg ggctggagtg gttgggcttt attagaaaca aagctaacgg ttacaccaca      180
gaatacagtg cgtctgtgaa aggcagattc accatctcaa gagataattc aaagaactca      240
ctgtatctgc aaatgaacag cctgaaaacc gaggacacgg ccgtgtatta ctgtgctaga      300
gataactggt ttgcttactg gggtcaagga accctggtca ccgtctcctc ggctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga tgaccaag      1080 aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa atgactcgag                                      1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

```
gaggtgcagc tggtggagtc tgggggaggc ttggtccagc ctggagggtc cctgagactc       60
tcctgtgcag cctctggatt caccttcact gactactaca tgagctgggt ccgccaggct      120
ccagggaagg ggctggagtg gttgggcttt attagaaaca aagctaacgg ttacaccaca      180
gaatacagtg cgtctgtgaa aggcagattc accatctcaa gagataattc aaagaactca      240
ctgtatctgc aaatgaacag cctgcgtgct gaggacacgg ccgtgtatta ctgtgctaga      300
gataactggt ttgcttactg gggtcaagga accctggtca ccgtctcctc ggctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaac tcctgggggg accgtcagtc      720
ttcctcttcc ccccaaaacc caaggacacc ctcatgatct cccggacccc tgaggtcaca      780
```

| | |
|---|---|
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

| | |
|---|---|
| gaggttcagc tggtggagtc tggcggtggc ctggtgcagc caggggggctc actccgtttg | 60 |
| tcctgtgcag cttctggctt caccttcact gattactaca tgagctgggt gcgtcaggcc | 120 |
| ccgggtaagg gcctggaatg gttgggtttt attagaaaca agctaatgg ttacacaaca | 180 |
| gagtacagtg catctgtgaa gggtcgtttc actataagca gagataattc caaaaacaca | 240 |
| ctgtacctgc agatgaacag cctgcgtgct gaggacactg ccgtctatta ttgtgctaga | 300 |
| gataactggt ttgcttactg gggccaaggg actctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctggggg accgtcagtc | 720 |
| ttcctcttcc cccaaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 50
<211> LENGTH: 669

```
<212> TYPE: DNA
<213> ORGANISM: Artificial Sequence
<220> FEATURE:
<223> OTHER INFORMATION: Synthetic nucleotide sequence of H1-light

<400> SEQUENCE: 50
gacatcgtga tgacccagtc tccagactcc ctggctgtgt ctctgggcga gagggccacc      60
atcaactgca agtccagcca gagtctttta gctagcggca accaaaataa ctacttagct     120
tggcaccagc agaaaccagg acagcctcct aagatgctca ttatttgggc atctacccgg     180
gtatccgggg tccctgaccg attcagtggc agcgggtctg ggacagattt cactctcacc     240
atcagcagcc tgcaggctga agatgtggca gtttattact gtcagcaatc ctatagtgct     300
cctctcacgt tcggaggcgg taccaaggtg gagatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
tgactcgag                                                             669

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51
gatattgtga tgacccagac tccactctcc ctgcccgtca cccctggaga gccggcctcc      60
atctcctgca agtccagtca gagtctttta gctagtggca accaaaataa ctacttggcc     120
tggcacctgc agaagccagg ccagtctcca cagatgctga tcatttgggc atccactagg     180
gtatctggag tcccagacag gttcagtggc agtgggtcag gcactgattt cacactgaaa     240
atcagcaggg tggaggctga ggatgttgga gtttattact gccagcagtc ctacagcgct     300
ccgctcacgt tcggacaggg taccaagctg gagctcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
tgactcgag                                                             669

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52
gacatcgtga tgacccagtc tccagactcc ctggctgtgt ctctgggcga gagggccacc      60
atcaactgca agtccagcca gagtctttta gctagcggca accaaaataa ctacttagct     120
```

```
tggtaccagc agaaaccagg acagcctcct aagctgctca ttatttgggc atctacccgg      180
gtatccgggg tccctgaccg attcagtggc agcgggtctg ggacagattt cactctcacc      240
atcagcagcc tgcaggctga agatgtggca gtttattact gtcagcaatc ctatagtgct      300
cctctcacgt tcggaggcgg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaaagt ctacgcctgc      600
gaagtcaccc atcagggcct gagctcgccc gtcacaaaga gcttcaacag gggagagtgt      660
tgactcgag                                                             669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

```
gatatccaga tgacccagtc cccgagctcc ctgtccgcct ctgtgggcga tagggtcacc       60
atcacctgca gtccagtca gagtcttta gctagtggca accaaaataa ctacttggcc      120
tggcaccaac agaaaccagg aaaagctccg aaaatgctga ttatttgggc atccactagg      180
gtatctggag tcccttctcg cttctctgga tccgggtctg ggacggattt cactctgacc      240
atcagcagtc tgcagccgga agacttcgca acttattact gtcagcagtc ctacagcgct      300
ccgctcacgt tcggacaggg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaaagt ctacgcctgc      600
gaagtcaccc atcagggcct gagctcgccc gtcacaaaga gcttcaacag gggagagtgt      660
tgactcgag                                                             669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55

```
gctagcgttt tagcagaagt tcaattggtt gaatctggtg gtggtttggt tcaaccaggt      60
ggttctttga gattgtcttg tgctgcttct ggttttactt tcaccgatta ttacatgtcc     120
tgggttagac aagctccagg taaaggtttg aatggttgg gtttcattag aaacaaggct      180
aacggttaca ctaccgaata ttctgcttct gttaaggtta gattcaccat ttctagagac     240
aactctaaga acaccttgta cttgcaaatg aactccttga gagctgaaga tactgctgtt     300
tattactgcg ctagagataa ttggtttgct tattggggtc aaggtacttt ggttactgtt     360
tcttctggcc tcgggggcct cggaggagga ggtagtggcg gaggaggctc cggtggatcc     420
agcggtgtgg gttccgatat tcaaatgacc caatctccat cttctttgtc tgcttcagtt     480
ggtgatagag ttaccattac ttgtaagtcc tcccaatctt tgttggcttc tggtaatcag     540
aacaattact ggcttggca tcaacaaaaa ccaggtaaag ctccaaagat gttgattatt     600
tgggcttcta ccagagtttc tggtgttcca tctagatttt ctggttctgg ttccggtact     660
gattttactt tgaccatttc atccttgcaa ccagaagatt tcgctactta ctactgtcaa     720
caatcttact ctgctccatt gacttttggt caaggtacaa aggtcgaaat caagagagaa     780
ttcggtaagc ctatccctaa ccctctcctc ggtctcgatt ctacgggtgg tggtggatct     840
ggtggtggtg ttctggtgg tggtggttct caggaactga caactatatg cgagcaaatc     900
ccctcaccaa ctttagaatc gacgccgtac tctttgtcaa cgactactat tttggccaac     960
gggaaggcaa tgcaaggagt ttttgaatat acaaatcag taacgtttgt cagtaattgc    1020
ggttctcacc cctcaacaac tagcaaaggc agccccataa acacacagta tgttttttga    1080
gtttaaac                                                              1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)

<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata tttttctgtta ttgctagcgt tttagcagaa gttcaattgg     600
ttgaatctgg tggtggtttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactcctt gagagctgaa gatactgctg tttattactg cgctagagat aattggtttg     900
cttattgggg tcaaggtact ttggttactg tttcttctgg cctcggggc ctcggaggag      960
gaggtagtgg cggaggaggc tccggtggat ccagcggtgt gggttccgat attcaaatga    1020
cccaatctcc atcttctttg tctgcttcag ttggtgatag agttaccatt acttgtaagt    1080
cctcccaatc tttgttggct tctggtaatc agaacaatta cttggcttgg catcaacaaa    1140
aaccaggtaa agctccaaag atgttgatta tttgggcttc taccagagtt tctggtgttc    1200
catctagatt ttctggttct ggttccggta ctgattttac tttgaccatt tcatccttgc    1260
aaccagaaga tttcgctact tactactgtc aacaatctta ctctgctcca ttgacttttg    1320
gtcaaggtac aaaggtcgaa atcaagagag aattcggtaa gcctatccct aaccctctcc    1380
tcggtctcga ttctacgggt ggtggtggat ctggtggtgg tggttctggt ggtggtggtt    1440
ctcaggaact gacaactata tgcgagcaaa tcccctcacc aactttagaa tcgacgccgt    1500
actctttgtc aacgactact attttggcca acgggaaggc aatgcaagga gttttttgaat    1560
attacaaatc agtaacgttt gtcagtaatt gcggttctca cccctcaaca actagcaaag    1620
gcagccccat aaacacacag tatgtttttt gagtttaaac ccgctgatct gataacaaca    1680
gtgtagatgt aacaaaatcg actttgttcc cactgtactt ttagctcgta caaaatacaa    1740
tatactttc atttctccgt aaacaacatg ttttcccatg taatatcctt ttctattttt    1800
cgttccgtta ccaactttac acatacttta tatagctatt cacttctata cactaaaaaa    1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcattttga    2040
```

```
cgaaatttgc tattttgtta gagtctttta caccatttgt ctccacacct ccgcttacat    2100
caacaccaat aacgccattt aatctaagcg catcaccaac attttctggc gtcagtccac    2160
cagctaacat aaaatgtaag ctctcggggc tctcttgcct tccaacccag tcagaaatcg    2220
agttccaatc caaaagttca cctgtcccac ctgcttctga atcaaacaag ggaataaacg    2280
aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa acatcctcc ttaggttgat     2460 tacgaaacac gccaaccaag tatttcggag tgcctgaact atttttatat gcttttacaa    2520
gacttgaaat tttccttgca ataaccgggt caattgttct cttttctattg gcacacata    2580 taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctccttt cttttttcga ccgaatttct tgaagacgaa agggcctcgt    2820
gatacgccta tttttatagg ttaatgtcat gataataatg gtttcttagg acggatcgct   2880
tgcctgtaac ttacacgcgc ctcgtatctt ttaatgatgg aataatttgg gaatttactc   2940
tgtgtttatt tattttatg ttttgtattt ggatttaga aagtaaataa agaaggtaga     3000
agagttacgg aatgaagaaa aaaaaataaa caaaggttta aaaaatttca acaaaaagcg   3060
tactttacat atatatttat tagacaagaa aagcagatta aatagatata cattcgatta   3120
acgataagta aaatgtaaaa tcacaggatt ttcgtgtgtg gtcttctaca cagacaagat   3180
gaaacaattc ggcattaata cctgagagca ggaagagcaa gataaaaggt agtatttgtt   3240
ggcgatcccc ctagagtctt ttacatcttc ggaaaacaaa aactattttt tctttaattt   3300 cttttttac tttctatttt taatttatat atttatatta aaaatttaa attataatta    3360 tttttatagc acgtgatgaa aaggacccag gtggcacttt tcggggaaat gtgcgcggaa   3420
cccctatttg tttattttc taaatacatt caaatatgta tccgctcatg agacaataac    3480
cctgataaat gcttcaataa tattgaaaaa ggaagagtat gagtattcaa catttccgtg   3540
tcgcccttat tcccttttt gcggcatttt gccttcctgt ttttgctcac ccagaaacgc    3600
tggtgaaagt aaaagatgct gaagatcagt tgggtgcacg agtgggttac atcgaactgg   3660
atctcaacag cggtaagatc cttgagagtt tcgccccga agaacgtttt ccaatgatga    3720
gcacttttaa agttctgcta tgtggcgcgg tattatcccg tgttgacgcc gggcaagagc   3780
aactcggtcg ccgcatacac tattctcaga tgacttggt tgagtactca ccagtcacag    3840
aaaagcatct tacggatggc atgacagtaa gagaattatg cagtgctgcc ataaccatga   3900
gtgataacac tgcggccaac ttacttctga acgatcgg aggaccgaag gagctaaccg     3960
cttttttgca caacatgggg gatcatgtaa ctcgccttga tcgttgggaa ccggagctga   4020
atgaagccat accaaacgac gagcgtgaca ccacgatgcc tgtagcaatg gcaacaacgt   4080
tgcgcaaact attaactggc gaactactta ctctagcttc ccggcaacaa ttaatagact   4140
ggatggaggc ggataaagtt gcaggaccac ttctgcgctc ggcccttccg gctggctggt   4200
ttattgctga taaatctgga gccggtgagc gtgggtctcg cggtatcatt gcagcactgg   4260
ggccagatgg taagccctcc cgtatcgtag ttatctacac gacgggcagt caggcaacta   4320
tggatgaacg aaatagacag atcgctgaga taggtgcctc actgattaag cattggtaac   4380
```

```
tgtcagacca agtttactca tatatacttt agattgattt aaaacttcat ttttaattta      4440
aaaggatcta ggtgaagatc cttttttgata atctcatgac caaaatccct taacgtgagt     4500
tttcgttcca ctgagcgtca gaccccgtag aaaagatcaa aggatcttct tgagatcctt      4560
tttttctgcg cgtaatctgc tgcttgcaaa caaaaaaacc accgctacca gcggtggttt      4620
gtttgccgga tcaagagcta ccaactcttt ttccgaaggt aactggcttc agcagagcgc      4680
agataccaaa tactgtcctt ctagtgtagc cgtagttagg ccaccacttc aagaactctg      4740
tagcaccgcc tacatacctc gctctgctaa tcctgttacc agtggctgct gccagtggcg      4800
ataagtcgtg tcttaccggg ttggactcaa gacgatagtt accggataag gcgcagcggt      4860
cgggctgaac ggggggttcg tgcacacagc ccagcttgga gcgaacgacc tacaccgaac      4920
tgagatacct acagcgtgag cattgagaaa gcgccacgct tcccgaaggg agaaaggcgg      4980
acaggtatcc ggtaagcggc agggtcggaa caggagagcg cacgagggag cttccagggg      5040
ggaacgcctg gtatctttat agtcctgtcg ggtttcgcca cctctgactt gagcgtcgat      5100
ttttgtgatg ctcgtcaggg gggccgagcc tatggaaaaa cgccagcaac gcggcctttt      5160
tacggttcct ggccttttgc tggccttttg ctcacatgtt ctttcctgcg ttatcccctg      5220
attctgtgga taaccgtatt accgcctttg agtgagctga taccgctcgc cgcagccgaa      5280
cgaccgagcg cagcgagtca gtgagcgagg aagcggaaga gcgcccaata cgcaaaccgc      5340
ctctccccgc gcgttggccg attcattaat gcagctggca cgacaggttt cccgactgga      5400
aagcgggcag tgagcgcaac gcaattaatg tgagttacct cactcattag gcaccccagg      5460
ctttacactt tatgcttccg gctcctatgt tgtgtggaat tgtgagcgga taacaatttc      5520
acacaggaaa cagctatgac catgattacg ccaagctcgg aattaaccct cactaaaggg      5580
aacaaaagct ggctagt                                                    5597

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                  10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58
gaattcacta gtgattaatt cgccgccacc atgattcac aggcccaggt cctcatgttg       60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga tttatttgggc atccactagg gtatctggag tcccttctcg cttctctgga     300
tccgggtctg gaacggattt cactctgacc atcagcagtc tgcagccgga agacttcgca     360
acttattact gtcagcagtc ctacagccgc ccgtacacgt tcggacaggg taccaaggtg     420
```

```
gagatcaaac gtacg                                                         435

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59
gaattcacta gtgattaatt cgccgccacc atggattcac aggcccaggt cctcatgttg        60
ctgctgctat cggtatctgg tacctgtgga gatatccaga tgacccagtc cccgagctcc       120
ctgtccgcct ctgtgggcga tagggtcacc atcacctgca agtccagtca gagtctttta       180
gctagtggca accaaaataa ctacttggcc tggcaccaac agaaaccagg aaaagctccg       240
aaaatgctga ttatttgggc atccactagg gtatctggag tcccttctcg cttctctgga       300
tccgggtctg ggacggattt cactctgacc atcagcagtc tgcagccgga agacttcgca       360
acttattact gtgggcagtc ctacagccgt ccgctcacgt tcggacaggg taccaaggtg       420
gagatcaaac gtacg                                                        435

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60
gaattcacta gtgattaatt cgccgccacc atggattcac aggcccaggt cctcatgttg        60
ctgctgctat cggtatctgg tacctgtgga gatatccaga tgacccagtc cccgagctcc       120
ctgtccgcct ctgtgggcga tagggtcacc atcacctgca agtccagtca gagtctttta       180
gctagtggca accaaaataa ctacttggcc tggcaccaac agaaaccagg aaaagctccg       240
aaaatgctga ttatttgggc atccactagg gtatctggag tcccttctcg cttctctgga       300
tccgggtctg ggacggattt cactctgacc atcagcagtc tgcagccgga agacttcgca       360
acttattact gtgcacagtc ctacagccat ccgttctctt tcggacaggg taccaaggtg       420
gagatcaaac gtacg                                                        435

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61
gaattcacta gtgattaatt cgccgccacc atggattcac aggcccaggt cctcatgttg        60
ctgctgctat cggtatctgg tacctgtgga gatatccaga tgacccagtc cccgagctcc       120
ctgtccgcct ctgtgggcga tagggtcacc atcacctgca agtccagtca gagtctttta       180
gctagtggca accaaaataa ctacttggcc tggcaccaac agaaaccagg aaaagctccg       240
aaaatgctga ttatttgggc atccactagg gtatctggag tcccttctcg cttctctgga       300
tccgggtctg ggacggattt cactctgacc atcagcagtc tgcagccgga agacttcgca       360
```

```
acttattact gtcagcagtc ctacagccgc ccgtttacgt tcggacaggg taccaaggtg    420
gagatcaaac gtacg                                                    435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, U6-HC7 hinge and constant
      region of human IgG1

<400> SEQUENCE: 62

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335
```

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
            450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63
gaattcgccg ccaccatgga atggagctgg gttttctcg taacactttt aaatggtatc      60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta agcagaga taattccaaa     300 aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260

```
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atgactcgag                                     1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain
of huAbF46-H4-A1, human IgG2 hinge and constant
region of human IgG1

<400> SEQUENCE: 64

```
Met Glu Trp Ser Trp Val Phe Leu Val Thr Leu Leu Asn Gly Ile Gln
  1               5                  10                  15

Cys Glu Val Gln Leu Val Glu Ser Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
```

```
                325                 330                 335
Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
        370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
        450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG1

<400> SEQUENCE: 65
gaattcgccg ccaccatgga atggagctgg gttttctcg taacactttt aaatggtatc      60
cagtgtgagg ttcagctggt ggagtctggc ggtggcctgg tgcagccagg ggctcactc     120 cgtttgtcct gtgcagcttc tggcttcacc ttcactgatt actacatgag ctgggtgcgt    180
caggccccgg gtaagggcct ggaatggttg gttttattta aaacaaagc taatggttac     240 acaacagagt acagtgcatc tgtgaagggt cgtttcacta agcagaga taattccaaa      300 aacacactgt acctgcagat gaacagcctg cgtgctgagg acactgccgt ctattattgt    360
gctagagata actggtttgc ttactgggc aagggactc tggtcaccgt ctcctcggct      420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgccccc ctgcccagca cctgaactcc tgggggggacc gtcagtcttc    780 ctcttccccc caaaacccaa ggacaccctc atgatctccc ggaccctga ggtcacatgc    840 gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
```

```
ggctccttct tcctctacag caagctcacc gtggacaaga gcaggtggca gcagggggaac  1320 gtcttctcat gctccgtgat gcatgaggct ctgcacaacc actacacgca gaagagcctc  1380
tccctgtctc cgggtaaatg actcgag                                       1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain of huAbF46-H4-A1, human IgG2 hinge and constant region of human IgG2

<400> SEQUENCE: 66

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320
```

```
Val Val His Gln Asp Trp Leu Asn Gly Lys Glu Tyr Lys Cys Lys Val
            325                 330                 335

Ser Asn Lys Gly Leu Pro Ala Pro Ile Glu Lys Thr Ile Ser Lys Thr
        340                 345                 350

Lys Gly Gln Pro Arg Glu Pro Gln Val Tyr Thr Leu Pro Pro Ser Arg
    355                 360                 365

Glu Glu Met Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2

<400> SEQUENCE: 67

```
gaattcgccg ccaccatgga atggagctgg gttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg gttttattta gaaacaaagc taatggttac    240
acaacagagt acagtgcatc tgtgaagggt cgtttcacta taagcagaga taattccaaa   300
aacacactgt acctgcagat gaacagcctg cgtgctgagg acactgccgt ctattattgt   360
gctagagata actggtttgc ttactggggc caagggactc tggtcaccgt ctcctcggct   420
agcaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga cccctgaggt cacgtgcgtg   840
gtggtggacg tgagccacga agaccccgag gtccagttca actggtacgt ggacggcgtg   900
gaggtgcata atgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aaggcctccc agcccccatc gagaaaacca tctccaaaac caaagggcag  1080
ccccgagaac acaggtgta cacctgccc catcccggg aggagatgac caagaaccag   1140
gtcagcctga cctgcctggt caaaggcttc taccccagcg acatcgccgt ggagtgggag  1200
```

```
agcaatgggc agccggagaa caactacaag accacgcctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatgact cgag                                          1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain of huAbF46-H4-A1(H36Y) and human kappa constant region

<400> SEQUENCE: 68

```
Met Asp Ser Gln Ala Gln Val Leu Met Leu Leu Leu Leu Ser Val Ser
 1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Ser Gln Ser
         35                  40                  45

Leu Leu Ala Ser Gly Asn Gln Asn Asn Tyr Leu Ala Trp Tyr Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide consisting of light chain of huAbF46-H4-A1(H36Y) and human kappa constant region

<400> SEQUENCE: 69

```
aattcactag tgattaattc gccgccacca tggattcaca ggcccaggtc ctcatgttgc    60
tgctgctatc ggtatctggt acctgtggag atatccagat gacccagtcc ccgagctccc    120
```

```
tgtccgcctc tgtgggcgat agggtcacca tcacctgcaa gtccagtcag agtcttttag      180
ctagtggcaa ccaaaataac tacttggcct ggtaccaaca gaaaccagga aaagctccga      240
aaatgctgat tatttgggca tccactaggg tatctggagt cccttctcgc ttctctggat      300
ccgggtctgg gacggatttc actctgacca tcagcagtct gcagccggaa gacttcgcaa      360
cttattactg tcagcagtcc tacagccgcc cgtacacgtt cggacagggt accaaggtgg      420
agatcaaacg tacggtggct gcaccatctg tcttcatctt cccgccatct gatgagcagt      480
tgaaatctgg aactgcctct gttgtgtgcc tgctgaataa cttctatccc agagaggcca      540
aagtacagtg gaaggtggat aacgccctcc aatcgggtaa ctcccaggag agtgtcacag      600
agcaggacag caaggacagc acctacagcc tcagcagcac cctgacgctg agcaaagcag      660
actacgagaa acacaaagtc tacgcctgcg aagtcaccca tcagggcctg agctcgcccg      720
tcacaaagag cttcaacagg ggagagtgtt gactcgag                              758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1 and human kappa constant region

<400> SEQUENCE: 70

```
Met Asp Ser Gln Ala Gln Val Leu Met Leu Leu Leu Leu Ser Val Ser
 1               5                  10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn His Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

-continued

```
<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
 1               5                  10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
 1               5                  10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
 1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
      anti-c-Met antibody (AbF46 or huAbF46-H1)

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
```

```
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)

<400> SEQUENCE: 75

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaactc tggggttcacc ttcactgatt actacatgag ctgggtccgc     180
cagcctccag gaaaggcact tgagtggttg ggttttatta gaaacaaagc taatggttac     240
acaacagagt acagtgcatc tgtgaagggt cggttcacca tctccagaga taattcccaa     300
```

```
agcatcctct atcttcaaat ggacaccctg agagctgagg acagtgccac ttattactgt    360
gcaagagata actggtttgc ttactggggc caagggactc tggtcactgt ctctgcagct    420
agcaccaagg gcccatcggt cttccccctg gcacctcct ccaagagcac ctctgggggc     480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttccccc aaaacccaag gacaccctca tgatctcccg gacccctgag     840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77
gaattcacta gtgattaatt cgccgccacc atggattcac aggcccaggt cctcatgttg    60
```

```
ctgctgctat cggtatctgg tacctgtgga gacattttga tgacccagtc tccatcctcc      120
ctgactgtgt cagcaggaga gaaggtcact atgagctgca agtccagtca gagtctttta      180
gctagtggca accaaaataa ctacttggcc tggcaccagc agaaaccagg acgatctcct      240
aaaatgctga taatttgggc atccactagg gtatctggag tccctgatcg cttcataggc      300
agtggatctg ggacggattt cactctgacc atcaacagtg tgcaggctga agatctggct      360
gtttattact gtcagcagtc ctacagcgct ccgctcacgt tcggtgctgg gaccaagctg      420
gagctgaaac gtacggtggc tgcaccatct gtcttcatct tcccgccatc tgatgagcag      480
ttgaaatctg gaactgcctc tgttgtgtgc ctgctgaata acttctatcc cagagaggcc      540
aaagtacagt ggaaggtgga taacgccctc caatcgggta actcccagga gagtgtcaca      600
gagcaggaca gcaaggacag cacctacagc ctcagcagca ccctgacgct gagcaaagca      660
gactacgaga aacacaaagt ctacgcctgc gaagtcaccc atcagggcct gagctcgccc      720
gtcacaaaga gcttcaacag gggagagtgt tgactcgag                             759

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78
atgaaggccc ccgctgtgct tgcacctggc atcctcgtgc tcctgtttac cttggtgcag       60
aggagcaatg gggagtgtaa agaggcacta gcaaagtccg atgatgaatgt gaatatgaag     120 tatcagcttc ccaacttcac cgcggaaaca cccatccaga atgtcattct acatgagcat     180
cacattttcc ttggtgccac taactacatt tatgttttaa atgaggaaga ccttcagaag     240
gttgctgagt acaagactgg gcctgtgctg aacacccag attgttttccc atgtcaggac     300 tgcagcagca aagccaattt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca cagtcggagg ttcactgc      480 atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gttttttgacg gaccagtcct acattgatgt tttaacctgag  720 ttcagagatt cttaccccat taagtatgtc catgcctttg aaagcaacaa ttttatttac   780
ttcttgacgg tccaaagga aactctagat gctcagactt tcacacaag aataatcagg     840 ttctgttcca taaactctgg attgcattcc tacatggaaa tgcctctgga gtgtattctc    900
acagaaaaga gaaaaagagat ccacaaaag aaggaagtgt taatatact tcaggctgcg    960 tatgtcagca agcctggggc ccagcttgct agacaaatag agccagcct gaatgatgac   1020 attctttttcg gggtgttcgc acaaagcaag ccagattctg ccgaaccaat ggatcgatct  1080
gccatgtgtg cattccctat caaatatgtc aacgacttct caacaagat cgtcaacaaa  1140 aacaatgtga gatgtctcca gcatttttac ggacccaatc atgagcactg ctttaatagg  1200
acacttctga gaaattcatc aggctgtgaa gcgcgccgtg atgaatatcg aacagagttt    1260
accacagctt tgcagcgcgt tgacttattc atgggtcaat tcagcgaagt cctcttaaca   1320
```

```
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata taaatttga tttaaagaaa     1800
actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt aactggaaat    2040
tacctaaaca gtgggaattc tagacacatt tcaattggtg gaaaaacatg tactttaaaa    2100
agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg gagcacaata    2280
acaggtgttg gaaaaacct gaattcagtt agtgtcccga gaatggtcat aaatgtgcat     2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520
tttaagcctt ttgaaaagcc agtgatgatc tcaatgggca atgaaaatgt actggaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttgacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg aatctgcct gcgaagtgaa gggtctccgc tggtggtcct accatacatg     3480
aaacatggag atcttcgaaa tttcattcga atgagactc ataatccaac tgtaaaagat     3540
cttattggct ttggtcttca gtagccaaa ggcatgaaat atcttgcaag caaaagtttg     3600
gtccacagag acttggctgc aagaaactgt atgctggatg aaaaattcac agtcaaggtt    3660
gctgattttg gtcttgccag agacatgtat gataaagaat actatagtgt acacaacaaa    3720
```

```
acaggtgcaa agctgccagt gaagtggatg gctttggaaa gtctgcaaac tcaaaagttt   3780
accaccaagt cagatgtgtg gtcctttggc gtgctcctct gggagctgat gacaagagga   3840
gccccacctt atcctgacgt aaacaccttt gatataactg tttacttgtt gcaagggaga   3900
agactcctac aacccgaata ctgcccagac cccttatatg aagtaatgct aaaatgctgg   3960
caccctaaag ccgaaatgcg cccatccttt tctgaactgg tgtcccggat atcagcgatc   4020
ttctctactt tcattgggga gcactatgtc catgtgaacg ctactatgt gaacgtaaaa    4080 tgtgtcgctc cgtatccttc tctgttgtca tcagaagata cgctgatga tgaggtggac    4140 acacgaccag cctccttctg ggagacatca                                    4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
  1               5                  10                  15

Leu Asn Glu Glu Asp Leu Gln Lys Val Ala Glu Tyr Lys Thr Gly Pro
             20                  25                  30

Val Leu Glu His Pro Asp Cys Phe Pro Cys Gln Asp Cys Ser Ser Lys
         35                  40                  45

Ala Asn Leu Ser Gly Gly Val Trp Lys Asp Asn Ile Asn Met Ala Leu
     50                  55                  60

Val Val Asp Thr Tyr Tyr Asp Asp Gln Leu Ile Ser Cys Gly Ser Val
 65                  70                  75                  80

Asn Arg Gly Thr Cys Gln Arg His Val Phe Pro His Asn His Thr Ala
                 85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
```

```
                275                 280                 285
Val Phe Ala Gln Ser Lys Pro Asp Ser Ala Glu Pro Met Asp Arg Ser
290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
                340                 345                 350

Cys Glu Ala Arg Arg Asp Glu Tyr Arg Thr Glu Phe Thr Thr Ala Leu
                355                 360                 365

Gln Arg Val Asp Leu Phe Met Gly Gln Phe Ser Glu Val Leu Leu Thr
370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
                420                 425                 430

Glu Val Ile Val Glu His Thr Leu Asn Gln Asn Gly
                435                 440
```

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

```
Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
                20                  25                  30

Pro Pro Phe Val Gln Cys Gly Trp Cys His Asp Lys Cys Val Arg Ser
                35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65              70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
                100                 105                 110

Thr Leu Ser Glu Ser Thr Met Asn Thr Leu Lys Cys Thr Val Gly Pro
                115                 120                 125

Ala Met Asn Lys His Phe Asn Met Ser Ile Ile Ser Asn Gly His
                130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
                180                 185                 190

Gly Gly Lys Thr Cys Thr Leu Lys Ser Val Ser Asn Ser Ile Leu Glu
```

```
                195                 200                 205
Cys Tyr Thr Pro Ala Gln Thr Ile Ser Thr Glu Phe Ala Val Lys Leu
210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Cys Phe Ala
                260                 265                 270

Ser Gly Gly Ser Thr Ile Thr Gly Val Gly Lys Asn Leu Asn Ser Val
                275                 280                 285

Ser Val Pro Arg Met Val Ile Asn Val His Glu Ala Gly Arg Asn Phe
290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
                340                 345                 350

Tyr Val His Asn Pro Val Phe Lys Pro Phe Glu Lys Pro Val Met Ile
                355                 360                 365

Ser Met Gly Asn Glu Asn Val Leu Glu Ile Lys Gly Asn Asp Ile Asp
370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
                420                 425                 430

Ile Ser Ser Thr Val Leu Gly Lys Val Ile Val Gln Pro Asp Gln Asn
                435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

Val His Phe Asn Glu Val Ile Gly Arg Gly His Phe Gly Cys Val Tyr
  1               5                  10                  15

His Gly Thr Leu Leu Asp Asn Asp Gly Lys Lys Ile His Cys Ala Val
                 20                  25                  30

Lys Ser Leu Asn Arg Ile Thr Asp Ile Gly Glu Val Ser Gln Phe Leu
             35                  40                  45

Thr Glu Gly Ile Ile Met Lys Asp Phe Ser His Pro Asn Val Leu Ser
         50                  55                  60

Leu Leu Gly Ile Cys Leu Arg Ser Glu Gly Ser Pro Leu Val Val Leu
 65                  70                  75                  80

Pro Tyr Met Lys His Gly Asp Leu Arg Asn Phe Ile Arg Asn Glu Thr
                 85                  90                  95

His Asn Pro Thr Val Lys Asp Leu Ile Gly Phe Gly Leu Gln Val Ala
```

```
            100                 105                 110
Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
        180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
        210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
                260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain
      of c-Met

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc    120
ccatgtcagg actgcagcag caaagccaat ttatcaggag gtgtttggaa agataacatc    180
aacatggctc tagttgtcga cacctactat gatgatcaac tcattagctg tggcagcgtc    240
aacagaggga cctgccagcg acatgtcttt ccccacaatc atactgctga catacagtcg    300
gaggttcact gcatattctc cccacagata gaagagccca gcagtgtcc tgactgtgtg      360 gtgagcgccc tgggagccaa agtcctttca tctgtaaagg accggttcat caacttcttt    420
gtaggcaata ccataaattc ttcttatttc ccagatcatc cattgcattc gatatcagtg    480
agaaggctaa aggaaacgaa gatggttttt atgtttttga cggaccagtc ctacattgat    540
gttttacctg agtcagaga ttcttacccc attaagtatg tccatgcctt tgaaagcaac      600 aatttttattt acttcttgac ggtccaaagg gaaactctag atgctcagac ttttcacaca    660
agaataatca ggttctgttc cataaactct ggattgcatt cctacatgga aatgcctctg    720
gagtgtattc tcagagaaaa gagaaaaaag agatccacaa agaaggaagt gtttaatata    780
cttcaggctg cgtatgtcag caagcctggg gcccagcttg ctagacaaat aggagccagc    840
```

```
ctgaatgatg acattctttt cggggtgttc gcacaaagca agccagattc tgccgaacca    900
atggatcgat ctgccatgtg tgcattccct atcaaatatg tcaacgactt cttcaacaag    960
atcgtcaaca aaacaatgt gagatgtctc cagcatttt acggacccaa tcatgagcac     1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aaccccctcat   1260 gtgaattttc tcctggactc ccatccagtg tctccagaag tgattgtgga gcatacatta    1320
aaccaaaatg gc                                                        1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
      domain of c-Met

<400> SEQUENCE: 83

```
tacacactgg ttatcactgg gaagaagatc acgaagatcc cattgaatgg cttgggctgc    60
agacatttcc agtcctgcag tcaatgcctc tctgccccac cctttgttca gtgtggctgg    120
tgccacgaca aatgtgtgcg atcggaggaa tgcctgagcg ggacatggac tcaacagatc    180
tgtctgcctg caatctacaa ggttttccca aatagtgcac cccttgaagg agggacaagg    240
ctgaccatat gtggctggga ctttggattt cggaggaata taaatttga tttaaagaaa     300 actagagttc tccttggaaa tgagagctgc accttgactt taagtgagag cacgatgaat    360
acattgaaat gcacagttgg tcctgccatg aataagcatt tcaatatgtc cataattatt    420
tcaaatggcc acgggacaac acaatacagt acattctcct atgtggatcc tgtaataaca    480
agtatttcgc cgaaatacgg tcctatggct ggtggcactt tacttacttt aactggaaat    540
tacctaaaca gtgggaattc tagacacatt tcaattggtg aaaaacatg tactttaaaa    600 agtgtgtcaa acagtattct tgaatgttat accccagccc aaaccatttc aactgagttt    660
gctgttaaat tgaaaattga cttagccaac cgagagacaa gcatcttcag ttaccgtgaa    720
gatcccattg tctatgaaat tcatccaacc aaatctttta ttagtggtgg gagcacaata    780
acaggtgttg ggaaaaacct gaattcagtt agtgtcccga gaatggtcat aaatgtgcat    840
gaagcaggaa ggaactttac agtggcatgt caacatcgct ctaattcaga gataatctgt    900
tgtaccactc cttccctgca acagctgaat ctgcaactcc ccctgaaaac caaagccttt    960
ttcatgttag atgggatcct ttccaaatac tttgatctca tttatgtaca taatcctgtg    1020
tttaagccct ttgaaaagcc agtgatgatc tcaatgggca atgaaaatgt actgaaatt    1080 aagggaaatg atattgaccc tgaagcagtt aaaggtgaag tgttaaaagt tggaaataag    1140
agctgtgaga atatacactt acattctgaa gccgttttat gcacggtccc caatgacctg    1200
ctgaaattga acagcgagct aaatatagag tggaagcaag caatttcttc aaccgtcctt    1260
ggaaaagtaa tagttcaacc agatcagaat ttcacagga                            1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain
     of c-Met

<400> SEQUENCE: 84

```
gtgcatttca atgaagtcat aggaagaggg cattttggtt gtgtatatca tgggactttg      60
ttggacaatg atggcaagaa aattcactgt gctgtgaaat ccttgaacag aatcactgac     120
ataggagaag tttcccaatt tctgaccgag ggaatcatca tgaaagattt tagtcatccc     180
aatgtcctct cgctcctggg aatctgcctg cgaagtgaag ggtctccgct ggtggtccta     240
ccatacatga acatggaga tcttcgaaat tcattcgaa atgagactca taatccaact        300
gtaaaagatc ttattggctt tggtcttcaa gtagccaaag gcatgaaata tcttgcaagc     360
aaaaagtttg tccacagaga cttggctgca agaaactgta tgctggatga aaaattcaca     420
gtcaaggttg ctgattttgg tcttgccaga gacatgtatg ataaagaata ctatagtgta     480
cacaacaaaa caggtgcaaa gctgccagtg aagtggatgg ctttggaaag tctgcaaact     540
caaaagttta ccaccaagtc agatgtgtgg tcctttggcg tgctcctctg ggagctgatg     600
acaagaggag ccccacctta tcctgacgta aacacctttg atataactgt ttacttgttg     660
caagggagaa gactcctaca acccgaatac tgcccagacc ccttatatga agtaatgcta     720
aaatgctggc accctaaagc cgaaatgcgc ccatcctttt ctgaactggt gtcccggata     780
tcagcgatct tctctacttt cattggggag cactatgtcc atgtgaacgc tacttatgtg     840
aacgtaaaat gtgtcgctcc gtatccttct ctgttgtcat cagaagataa cgctgatgat     900
gaggtggaca cacgaccagc ctccttctgg gagacatca                            939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met
     antibody

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
     antibody

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
     monoclonal antibody AbF46

<400> SEQUENCE: 87

Glu Val Lys Leu Val Glu Ser Gly Gly Gly Leu Val Gln Pro Gly Gly
1               5                   10                  15

```
Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
            115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody

<400> SEQUENCE: 88

Asp Ile Leu Met Thr Gln Ser Pro Ser Ser Leu Thr Val Ser Ala Gly
  1               5                  10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
  1               5                  10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1
```

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

```
Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
                35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
                35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
                100                 105                 110
```

Val Thr Val Ser Ser
            115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody (huAbF46-H4)

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly
1               5                   10                  15

Asp Arg Val Thr Met Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val

```
                    50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region (U7-HC6)

<400> SEQUENCE: 100

Glu Pro Ser Cys Asp Lys His Cys Cys Pro Pro Cys Pro
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region (U6-HC7)

<400> SEQUENCE: 101

Glu Pro Lys Ser Cys Asp Cys His Cys Pro Pro Cys Pro
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
 1               5                  10

<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
 1               5                  10
```

```
<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
 1               5                  10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
 1               5                  10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
             20                  25                  30

Gly Asn Gln Asn Asn Tyr Leu Ala Trp Tyr Gln Gln Lys Pro Gly Lys
```

```
                      35                  40                  45
Ala Pro Lys Met Leu Ile Ile Trp Ala Ser Thr Arg Val Ser Gly Val
             50                  55                  60

Pro Ser Arg Phe Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                     85                  90                  95

Ser Tyr Ser Arg Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
                130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 109
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
      against anti-c-Met antibody
<220> FEATURE:
<221> NAME/KEY: MOD_RES
<222> LOCATION: (1)
<223> OTHER INFORMATION: Xaa is Asp(D), Ans(N), or Gly(G)
<220> FEATURE:
<221> NAME/KEY: MOD_RES
<222> LOCATION: (3)
<223> OTHER INFORMATION: Xaa is Tyr(Y), Ala(A), Asp (D), or Ser(S)

<400> SEQUENCE: 109

Xaa Tyr Xaa Met Ser
 1               5

<210> SEQ ID NO 110
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
      against anti-c-Met antibody
<220> FEATURE:
<221> NAME/KEY: MOD_RES
<222> LOCATION: (3)
<223> OTHER INFORMATION: Xaa is Ala(A) or Gly(G)
<220> FEATURE:
<221> NAME/KEY: MOD_RES
<222> LOCATION: (4)
<223> OTHER INFORMATION: Xaa is Met(M) or Ile(I)
<220> FEATURE:
<221> NAME/KEY: MOD_RES
<222> LOCATION: (5)
<223> OTHER INFORMATION: Xaa is Ser(S) or His(H)

<400> SEQUENCE: 110
```

```
Ser Tyr Xaa Xaa Xaa
 1               5
```

<210> SEQ ID NO 111
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody
<220> FEATURE:
<221> NAME/KEY: MOD_RES
<222> LOCATION: (1)
<223> OTHER INFORMATION: Xaa is Gly(G), Ser(S), Leu(L), Ala(A), or
      Val(V)
<220> FEATURE:
<221> NAME/KEY: MOD_RES
<222> LOCATION: (3)
<223> OTHER INFORMATION: Xaa is Tyr(Y) or Ser(S)
<220> FEATURE:
<221> NAME/KEY: MOD_RES
<222> LOCATION: (4)
<223> OTHER INFORMATION: Xaa is Ser(S), Tyr(Y), His(H), Pro(P), or
      Gly(G)
<220> FEATURE:
<221> NAME/KEY: MOD_RES
<222> LOCATION: (5)
<223> OTHER INFORMATION: Xaa is Ser(S), Gly(G), Gly(N), or Asp(D)
<220> FEATURE:
<221> NAME/KEY: MOD_RES
<222> LOCATION: (6)
<223> OTHER INFORMATION: Xaa is Ser(S), Gly(G), or Asp(D)
<220> FEATURE:
<221> NAME/KEY: MOD_RES
<222> LOCATION: (7)
<223> OTHER INFORMATION: Xaa is Ser(S) or Gly(G)
<220> FEATURE:
<221> NAME/KEY: MOD_RES
<222> LOCATION: (8)
<223> OTHER INFORMATION: Xaa is Ans(N) or Ser(S)
<220> FEATURE:
<221> NAME/KEY: MOD_RES
<222> LOCATION: (9)
<223> OTHER INFORMATION: Xaa is Ile(I), Thr(T), or Lys(K)
<220> FEATURE:
<221> NAME/KEY: MOD_RES
<222> LOCATION: (16)
<223> OTHER INFORMATION: Xaa is Lys(K) or Glu(E)

<400> SEQUENCE: 111

```
Xaa Ile Xaa Xaa Xaa Xaa Xaa Xaa Xaa Tyr Tyr Ala Asp Ser Val Xaa
 1               5                  10                  15
Gly
```

<210> SEQ ID NO 112
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody
<220> FEATURE:
<221> NAME/KEY: MOD_RES
<222> LOCATION: (1)
<223> OTHER INFORMATION: Xaa is Ser(S) or Thr(T)
<220> FEATURE:
<221> NAME/KEY: MOD_RES
<222> LOCATION: (9)
<223> OTHER INFORMATION: Xaa is Ans(N) or Ser(S)
<220> FEATURE:
<221> NAME/KEY: MOD_RES
<222> LOCATION: (11)
<223> OTHER INFORMATION: Xaa is Ser(S), Tyr(Y), or Asp(D)
<220> FEATURE:

```
<221> NAME/KEY: MOD_RES
<222> LOCATION: (13)
<223> OTHER INFORMATION: Xaa is Tyr(Y), Thr(T), Ans(N), or Ser(S)

<400> SEQUENCE: 112

Xaa Gly Ser Ser Ser Asn Ile Gly Xaa Asn Xaa Val Xaa
 1               5                  10

<210> SEQ ID NO 113
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody
<220> FEATURE:
<221> NAME/KEY: MOD_RES
<222> LOCATION: (1)
<223> OTHER INFORMATION: Xaa is Ser(S), Ala(A), Ans(N), or Glu(E)
<220> FEATURE:
<221> NAME/KEY: MOD_RES
<222> LOCATION: (2)
<223> OTHER INFORMATION: Xaa is Asp(D), Ans(N), Thr(T), or Val(V)
<220> FEATURE:
<221> NAME/KEY: MOD_RES
<222> LOCATION: (3)
<223> OTHER INFORMATION: Xaa is Ser(S) or Ans(N)
<220> FEATURE:
<221> NAME/KEY: MOD_RES
<222> LOCATION: (4)
<223> OTHER INFORMATION: Xaa is Gln(Q), Ans(N), His(H), or Gly(G)

<400> SEQUENCE: 113

Xaa Xaa Xaa Xaa Arg Pro Ser
 1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody
<220> FEATURE:
<221> NAME/KEY: MOD_RES
<222> LOCATION: (1)
<223> OTHER INFORMATION: Xaa is Gly(G) or Ala(A)
<220> FEATURE:
<221> NAME/KEY: MOD_RES
<222> LOCATION: (2)
<223> OTHER INFORMATION: Xaa is Thr(T), Ala(A), or Ser(S)
<220> FEATURE:
<221> NAME/KEY: MOD_RES
<222> LOCATION: (5)
<223> OTHER INFORMATION: Xaa is Tyr(Y), Asp(D), Ser(S), or Ala(A)
<220> FEATURE:
<221> NAME/KEY: MOD_RES
<222> LOCATION: (8)
<223> OTHER INFORMATION: Xaa is Asp(N) or Ser(S)
<220> FEATURE:
<221> NAME/KEY: MOD_RES
<222> LOCATION: (9)
<223> OTHER INFORMATION: Xaa is Gly(G) or Ala(A)

<400> SEQUENCE: 114

Xaa Xaa Trp Asp Xaa Ser Leu Xaa Xaa
 1               5

<210> SEQ ID NO 115
<211> LENGTH: 5
<212> TYPE: PRT
<213> ORGANISM: Artificial Sequence
<220> FEATURE:
```

<223> OTHER INFORMATION: Synthetic CDR-H1 of anti-idiotype antibody
against anti-c-Met antibody

<400> SEQUENCE: 115

Asp Tyr Tyr Met Ser
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
against anti-c-Met antibody

<400> SEQUENCE: 116

Asn Tyr Ala Met Ser
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
against anti-c-Met antibody

<400> SEQUENCE: 117

Asp Tyr Asp Met Ser
1               5

<210> SEQ ID NO 118
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
against anti-c-Met antibody

<400> SEQUENCE: 118

Gly Tyr Asp Met Ser
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
against anti-c-Met antibody

<400> SEQUENCE: 119

Asp Tyr Ala Met Ser
1               5

<210> SEQ ID NO 120
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
against anti-c-Met antibody

<400> SEQUENCE: 120

Asn Tyr Ser Met Ser
1               5

-continued

<210> SEQ ID NO 121
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
      against anti-c-Met antibody

<400> SEQUENCE: 121

Ser Tyr Ala Met His
 1               5

<210> SEQ ID NO 122
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
      against anti-c-Met antibody

<400> SEQUENCE: 122

Ser Tyr Ala Ile Ser
 1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
      against anti-c-Met antibody

<400> SEQUENCE: 123

Ser Tyr Gly Met His
 1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic CDR-H1 of anti-idiotype antibody
      against anti-c-Met antibody

<400> SEQUENCE: 124

Ser Tyr Ala Met Ser
 1               5

<210> SEQ ID NO 125
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 125

Gly Ile Tyr Ser Ser Ser Ser Asn Ile Tyr Tyr Ala Asp Ser Val Lys
 1               5                  10                  15

Gly

<210> SEQ ID NO 126
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 126

Ser Ile Ser Ser Ser Gly Gly Asn Thr Tyr Tyr Ala Asp Ser Val Lys
 1               5                   10                  15
Gly

<210> SEQ ID NO 127
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 127

Leu Ile Ser Tyr Gly Gly Ser Asn Thr Tyr Tyr Ala Asp Ser Val Lys
 1               5                   10                  15
Gly

<210> SEQ ID NO 128
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 128

Gly Ile Ser His Gly Asp Gly Asn Ile Tyr Tyr Ala Asp Ser Val Lys
 1               5                   10                  15
Gly

<210> SEQ ID NO 129
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 129

Ser Ile Ser Tyr Gly Gly Gly Ser Ile Tyr Tyr Ala Asp Ser Val Lys
 1               5                   10                  15
Gly

<210> SEQ ID NO 130
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 130

Gly Ile Ser Tyr Asn Gly Gly Ser Lys Tyr Tyr Ala Asp Ser Val Lys
 1               5                   10                  15
Gly

<210> SEQ ID NO 131
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody against anti-c-Met antibody

<400> SEQUENCE: 131

Ala Ile Ser His Ser Ser Gly Asn Thr Tyr Tyr Ala Asp Ser Val Lys
1               5                   10                  15
Gly

<210> SEQ ID NO 132
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 132

Ala Ile Tyr Pro Gly Gly Gly Asn Thr Tyr Tyr Ala Asp Ser Val Lys
1               5                   10                  15
Gly

<210> SEQ ID NO 133
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 133

Ala Ile Ser Ser Gly Asp Gly Asn Thr Tyr Tyr Ala Asp Ser Val Lys
1               5                   10                  15
Gly

<210> SEQ ID NO 134
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 134

Ser Ile Tyr Pro Asp Asp Gly Asn Thr Tyr Tyr Ala Asp Ser Val Lys
1               5                   10                  15
Gly

<210> SEQ ID NO 135
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 135

Val Ile Ser Tyr Asp Gly Ser Asn Lys Tyr Tyr Ala Asp Ser Val Lys
1               5                   10                  15
Gly

<210> SEQ ID NO 136
<211> LENGTH: 17
<212> TYPE: PRT
<213> ORGANISM: Artificial Sequence
<220> FEATURE:

```
<223> OTHER INFORMATION: Synthetic CDR-H2 of anti-idiotype antibody
      against anti-c-Met antibody

<400> SEQUENCE: 136

Ala Ile Ser Gly Ser Gly Gly Ser Thr Tyr Tyr Ala Asp Ser Val Glu
 1               5                  10                  15

Gly

<210> SEQ ID NO 137
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 137

Ala Ile Ser Gly Ser Gly Gly Ser Thr Tyr Tyr Ala Asp Ser Val Lys
 1               5                  10                  15

Gly

<210> SEQ ID NO 138
<211> LENGTH: 17
<212> TYPE: PRT
<213> ORGANISM: Artificial Sequence
<220> FEATURE:
<223> OTHER INFORMATION: Synthetic CDR-H2 of anti-idiotype antibody
      against anti-c-Met antibody

<400> SEQUENCE: 138

Gly Ile Ile Pro Ile Phe Gly Thr Ala Asn Tyr Ala Gln Lys Phe Gln
 1               5                  10                  15

Gly

<210> SEQ ID NO 139
<211> LENGTH: 19
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 139

Lys Ala Leu Gly Asn Gln Glu Asn Glu Pro Thr Ser Tyr Ser Asn Gly
 1               5                  10                  15

Met Asp Val

<210> SEQ ID NO 140
<211> LENGTH: 8
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 140

Lys Tyr His Ser Val Phe Asp Tyr
 1               5

<210> SEQ ID NO 141
<211> LENGTH: 19
<212> TYPE: PRT
<213> ORGANISM: Artificial Sequence
<220> FEATURE:
<223> OTHER INFORMATION: Synthetic CDR-H3 of anti-idiotype antibody
``` against anti-c-Met antibody

<400> SEQUENCE: 141

Lys Phe Arg Ser Glu Phe Asn Glu Asn Glu Pro Ser Ser Tyr Tyr Gly
1               5                   10                  15

Met Asp Val

<210> SEQ ID NO 142
<211> LENGTH: 19
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 142

Lys Val Gly Leu Leu Phe Val Gln Glu Glu Pro Ser Tyr Tyr Asn Ala
1               5                   10                  15

Met Asp Val

<210> SEQ ID NO 143
<211> LENGTH: 8
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 143

Arg Asp Ala Ala Tyr Phe Asp Tyr
1               5

<210> SEQ ID NO 144
<211> LENGTH: 19
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 144

Lys Tyr Leu Leu Pro Val Leu Glu Glu Pro Gly Tyr Ser Ala Asp Gly
1               5                   10                  15

Met Asp Val

<210> SEQ ID NO 145
<211> LENGTH: 19
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 145

Lys His Leu Gly Ala Gln Ser Asp Glu Pro Asp Ser Ser Ser Asn Gly
1               5                   10                  15

Met Asp Val

<210> SEQ ID NO 146
<211> LENGTH: 19
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 146

Lys Ser Leu Ser Thr His Ser Val Asp Glu Pro Ser Ser Asp Asn Ala
1               5                   10                  15

Met Asp Val

<210> SEQ ID NO 147
<211> LENGTH: 19
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 147

Arg Tyr Leu Gly Thr Thr Ser Asp Glu Pro Ala Ser Tyr Ser Asn Gly
1               5                   10                  15

Met Asp Val

<210> SEQ ID NO 148
<211> LENGTH: 19
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 148

Lys Tyr Arg Leu Val Asp Arg Trp Glu Glu Pro Ser Ser Asp Tyr Gly
1               5                   10                  15

Met Asp Val

<210> SEQ ID NO 149
<211> LENGTH: 8
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 149

Arg Val His Leu Tyr Phe Asp Tyr
1               5

<210> SEQ ID NO 150
<211> LENGTH: 18
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 150

Arg Glu Asp Asn Thr Arg Tyr Phe Glu Glu Pro Asn Tyr Tyr Gly Met
1               5                   10                  15

Asp Val

<210> SEQ ID NO 151
<211> LENGTH: 16
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

```
<400> SEQUENCE: 151

Arg Asp Arg Asn Ser Tyr Tyr Glu Glu Pro Met Tyr Tyr Phe Asp Tyr
 1               5                  10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 152

Arg Asp Leu Val Ala Asp Asp Tyr Gly Asp Tyr Gly Thr Val Asp Tyr
 1               5                  10                  15

<210> SEQ ID NO 153
<211> LENGTH: 12
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 153

Lys Glu Arg Leu Glu Glu Pro Gly Phe Phe Asp Tyr
 1               5                  10

<210> SEQ ID NO 154
<211> LENGTH: 21
<212> TYPE: PRT
<213> ORGANISM: Artificial Sequence
<220> FEATURE:
<223> OTHER INFORMATION: Synthetic CDR-H3 of anti-idiotype antibody
      against anti-c-Met antibody

<400> SEQUENCE: 154

Ala Arg Gly Gly Gly Tyr Ser Tyr Gly Tyr Glu Glu Pro Tyr Tyr Tyr
 1               5                  10                  15

Tyr Gly Met Asp Val
            20

<210> SEQ ID NO 155
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 155

Ser Gly Ser Ser Ser Asn Ile Gly Asn Asn Ser Val Tyr
 1               5                  10

<210> SEQ ID NO 156
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 156

Ser Gly Ser Ser Ser Asn Ile Gly Asn Asn Tyr Val Tyr
 1               5                  10
```

```
<210> SEQ ID NO 157
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 157

Ser Gly Ser Ser Ser Asn Ile Gly Asn Asn Asp Val Thr
 1               5                   10

<210> SEQ ID NO 158
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 158

Thr Gly Ser Ser Ser Asn Ile Gly Ser Asn Asn Val Thr
 1               5                   10

<210> SEQ ID NO 159
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 159

Ser Gly Ser Ser Ser Asn Ile Gly Asn Asn Ser Val Asn
 1               5                   10

<210> SEQ ID NO 160
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 160

Thr Gly Ser Ser Ser Asn Ile Gly Ser Asn Tyr Val Ser
 1               5                   10

<210> SEQ ID NO 161
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 161

Thr Gly Ser Ser Ser Asn Ile Gly Asn Asn Asp Val Tyr
 1               5                   10

<210> SEQ ID NO 162
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 162
```

Thr Gly Ser Ser Ser Asn Ile Gly Ser Asn Ser Val Ser
1               5                   10

<210> SEQ ID NO 163
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 163

Ser Gly Ser Ser Ser Asn Ile Gly Ser Asn Asp Val Tyr
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 164

Thr Gly Ser Ser Ser Asn Ile Gly Ser Asn Asn Val Asn
1               5                   10

<210> SEQ ID NO 165
<211> LENGTH: 13
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 165

Ser Gly Ser Ser Ser Asn Ile Gly Ser Asn Ser Val Asn
1               5                   10

<210> SEQ ID NO 166
<211> LENGTH: 14
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 166

Thr Gly Ser Ser Ser Asn Ile Gly Ala Ala Tyr Glu Val His
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 167

Ser Gly Asp Lys Leu Gly Asp Arg Tyr Val Phe
1               5                   10

<210> SEQ ID NO 168
<211> LENGTH: 13
<212> TYPE: PRT
<213> ORGANISM: Artificial Sequence

```
<220> FEATURE:
<223> OTHER INFORMATION: Synthetic CDR-L1 of anti-idiotype antibody
      against anti-c-Met antibody

<400> SEQUENCE: 168

Ser Gly Ser Gly Ser Asn Ile Gly Ser Asn Ala Val Asn
 1               5                  10

<210> SEQ ID NO 169
<211> LENGTH: 11
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 169

Gly Gly Asn Asn Ile Ala Thr Lys Gly Val His
 1               5                  10

<210> SEQ ID NO 170
<211> LENGTH: 14
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 170

Thr Gly Thr Ser Ser Asp Val Gly Gly Tyr Asn Tyr Val Ser
 1               5                  10

<210> SEQ ID NO 171
<211> LENGTH: 17
<212> TYPE: PRT
<213> ORGANISM: Artificial Sequence
<220> FEATURE:
<223> OTHER INFORMATION: Synthetic CDR-L1 of anti-idiotype antibody
      against anti-c-Met antibody

<400> SEQUENCE: 171

Lys Ser Ser Gln Ser Leu Leu Asn Ser Gly Asn Gln Lys Asn Asp Leu
 1               5                  10                  15

Ala

<210> SEQ ID NO 172
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 172

Ser Asp Ser Gln Arg Pro Ser
 1               5

<210> SEQ ID NO 173
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 173

Ala Asn Asn Gln Arg Pro Ser
```

```
                   1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 174

Ser Asp Ser Asn Arg Pro Ser
  1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 175

Ser Asn Ser His Arg Pro Ser
  1               5

<210> SEQ ID NO 176
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 176

Ala Asn Asn Asn Arg Pro Ser
  1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 177

Ser Asp Ser Asn Arg Pro Ser
  1               5

<210> SEQ ID NO 178
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 178

Asp Asp Ser Asn Arg Pro Ser
  1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
```

-continued against anti-c-Met antibody

<400> SEQUENCE: 179

Ser Asp Asn Asn Arg Pro Ser
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 180

Ala Asp Ser Gln Arg Pro Ser
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 181

Ser Asp Ser His Arg Pro Ser
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 182

Asp Thr Ser Asn Arg Pro Ser
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 183

Asp Asp Ser Asp Arg Pro Ser
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 184

Ser Asn Asn Gln Arg Pro Ser
1               5

<210> SEQ ID NO 185

```
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 185

Asp Asp Ser Gly Arg Pro Ser
  1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 186

Glu Val Ser Asn Arg Pro Ser
  1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic CDR-L2 of anti-idiotype antibody
      against anti-c-Met antibody

<400> SEQUENCE: 187

Gly Ala Ser Thr Arg Glu Ser
  1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 188

Gly Thr Trp Asp Tyr Ser Leu Asn Gly
  1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 189

Gly Ala Trp Asp Asp Ser Leu Ser Gly
  1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 190
```

```
Gly Thr Trp Asp Ser Ser Leu Ser Ala
 1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 191

Gly Thr Trp Asp Asp Ser Leu Asn Gly
 1               5

<210> SEQ ID NO 192
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 192

Gly Ala Trp Asp Ala Ser Leu Asn Gly
 1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 193

Ala Thr Trp Asp Ala Ser Leu Ser Ala
 1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 194

Ala Ser Trp Asp Tyr Ser Leu Asn Ala
 1               5

<210> SEQ ID NO 195
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 195

Gly Ser Trp Asp Ser Ser Leu Ser Gly
 1               5

<210> SEQ ID NO 196
<211> LENGTH: 9
<212> TYPE: PRT
<213> ORGANISM: Artificial Sequence
<220> FEATURE:
```

```
<223> OTHER INFORMATION: Synthetic CDR-L3 of anti-idiotype antibody
      against anti-c-Met antibody

<400> SEQUENCE: 196

Gly Ser Trp Asp Asp Ser Leu Ser Gly
  1               5

<210> SEQ ID NO 197
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 197

Ala Ala Trp Asp Asp Ser Leu Asn Gly
  1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 198

Gln Val Trp Asp Ser Val Asn Asp His
  1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 199

Gln Leu Trp Asp Gly Arg Ser Asp Gln
  1               5

<210> SEQ ID NO 200
<211> LENGTH: 8
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 200

Ser Ser Tyr Thr Thr Asp Asn Ala
  1               5

<210> SEQ ID NO 201
<211> LENGTH: 7
<212> TYPE: PRT
<213> ORGANISM: Artificial Sequence
<220> FEATURE:
<223> OTHER INFORMATION: Synthetic CDR-L3 of anti-idiotype antibody
      against anti-c-Met antibody

<400> SEQUENCE: 201

Gln Asn Asp His Ser Tyr Pro
  1               5
```

<210> SEQ ID NO 202
<211> LENGTH: 127
<212> TYPE: PRT
<213> ORGANISM: Artificial Sequence
<220> FEATURE:
<223> OTHER INFORMATION: Synthetic heavy chain variable region of anti-idiotype antibody (EW01) against anti-c-Met antibody

<400> SEQUENCE: 202

```
Glu Val Gln Leu Leu Glu Ser Gly Gly Gly Leu Val Gln Pro Gly Gly
 1               5                  10                  15

Ser Leu Arg Leu Ser Cys Ala Val Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Ser Ser Ser Asn Ile Tyr Tyr Ala Asp Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Leu Gly Asn Gln Glu Asn Glu Pro Thr Ser Tyr Ser Asn
            100                 105                 110

Gly Met Asp Val Trp Gly Gln Gly Thr Leu Val Thr Val Ser Ser
        115                 120                 125
```

<210> SEQ ID NO 203
<211> LENGTH: 116
<212> TYPE: PRT
<213> ORGANISM: Artificial Sequence
<220> FEATURE:
<223> OTHER INFORMATION: Synthetic heavy chain variable region of anti-idiotype antibody (EW02) against anti-c-Met antibody

<400> SEQUENCE: 203

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Ser Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Ala Glu Asp Thr Ala Val Tyr Tyr Cys
                85                  90                  95

Ala Lys Tyr His Ser Val Phe Asp Tyr Trp Gly Gln Gly Thr Leu Val
            100                 105                 110

Thr Val Ser Ser
        115
```

<210> SEQ ID NO 204
<211> LENGTH: 127
<212> TYPE: PRT
<213> ORGANISM: Artificial Sequence
<220> FEATURE:
<223> OTHER INFORMATION: Synthetic heavy chain variable region of anti-idiotype antibody (EW03) against anti-c-Met antibody

<400> SEQUENCE: 204

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Leu Ile Ser Tyr Gly Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Ser Glu Phe Asn Glu Asn Glu Pro Ser Ser Tyr Tyr
            100                 105                 110

Gly Met Asp Val Trp Gly Gln Gly Thr Leu Val Thr Val Ser Ser
        115                 120                 125

<210> SEQ ID NO 205
<211> LENGTH: 127
<212> TYPE: PRT
<213> ORGANISM: Artificial Sequence
<220> FEATURE:
<223> OTHER INFORMATION: Synthetic heavy chain variable region of
      anti-idiotype antibody (EW06) against anti-c-Met antibody

<400> SEQUENCE: 205

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Gly Ile Ser His Gly Asp Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Gly Leu Leu Phe Val Gln Glu Pro Ser Tyr Tyr Asn
            100                 105                 110

Ala Met Asp Val Trp Gly Gln Gly Thr Leu Val Thr Val Ser Ser
        115                 120                 125

<210> SEQ ID NO 206
<211> LENGTH: 116
<212> TYPE: PRT
<213> ORGANISM: Artificial Sequence
<220> FEATURE:
<223> OTHER INFORMATION: Synthetic heavy chain variable region of
      anti-idiotype antibody (EW09) against anti-c-Met antibody

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ser Ile Ser Tyr Gly Gly Ser Ile Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg Asp Ala Ala Tyr Phe Asp Tyr Trp Gly Gln Gly Thr Leu Val
            100                 105                 110

Thr Val Ser Ser
        115

<210> SEQ ID NO 207
<211> LENGTH: 127
<212> TYPE: PRT
<213> ORGANISM: Artificial Sequence
<220> FEATURE:
<223> OTHER INFORMATION: Synthetic heavy chain variable region of
      anti-idiotype antibody (EW10) against anti-c-Met antibody

<400> SEQUENCE: 207

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
                20                  25                  30

Asp Met Ser Trp Val Arg Gln Ala Pro Gly Lys Gly Leu Glu Trp Val
            35                  40                  45

Ser Gly Ile Ser Tyr Asn Gly Gly Ser Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Leu Leu Pro Val Leu Glu Glu Pro Gly Tyr Ser Ala Asp
            100                 105                 110

Gly Met Asp Val Trp Gly Gln Gly Thr Leu Val Thr Val Ser Ser
        115                 120                 125

<210> SEQ ID NO 208
<211> LENGTH: 127
<212> TYPE: PRT
<213> ORGANISM: Artificial Sequence
<220> FEATURE:
<223> OTHER INFORMATION: Synthetic heavy chain variable region of
      anti-idiotype antibody (EW16) against anti-c-Met antibody

<400> SEQUENCE: 208

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Tyr Met Ser Trp Val Arg Leu Ala Pro Gly Lys Gly Leu Glu Trp Val
            35                  40                  45

Ser Ala Ile Ser His Ser Ser Gly Asn Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Leu Gly Ala Gln Ser Asp Glu Pro Asp Ser Ser Asn
        100                 105                 110

Gly Met Asp Val Trp Gly Gln Gly Thr Leu Val Thr Val Ser Ser
        115                 120                 125

<210> SEQ ID NO 209
<211> LENGTH: 127
<212> TYPE: PRT
<213> ORGANISM: Artificial Sequence
<220> FEATURE:
<223> OTHER INFORMATION: Synthetic heavy chain variable region of
      anti-idiotype antibody (EW26) against anti-c-Met antibody

<400> SEQUENCE: 209

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Tyr Pro Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu Ser Thr His Ser Val Asp Glu Pro Ser Ser Asp Asn
            100                 105                 110

Ala Met Asp Val Trp Gly Gln Gly Thr Leu Val Thr Val Ser Ser
        115                 120                 125

<210> SEQ ID NO 210
<211> LENGTH: 127
<212> TYPE: PRT
<213> ORGANISM: Artificial Sequence
<220> FEATURE:
<223> OTHER INFORMATION: Synthetic heavy chain variable region of
      anti-idiotype antibody (EW28) against anti-c-Met antibody

<400> SEQUENCE: 210

Glu Val Gln Leu Leu Glu Ser Gly Gly Gly Leu Val Gln Thr Gly Gly
1               5                   10                  15

Ser Leu Arg Leu Ser Cys Ala Val Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Ser Ser Gly Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Leu Gly Thr Thr Ser Asp Glu Pro Ala Ser Tyr Ser Asn
            100                 105                 110

Gly Met Asp Val Trp Gly Gln Gly Thr Leu Val Thr Val Ser Ser
        115                 120                 125

<210> SEQ ID NO 211

```
<211> LENGTH: 127
<212> TYPE: PRT
<213> ORGANISM: Artificial Sequence
<220> FEATURE:
<223> OTHER INFORMATION: Synthetic heavy chain variable region of
      anti-idiotype antibody (EW34) against anti-c-Met antibody

<400> SEQUENCE: 211

Glu Val Gln Leu Leu Glu Ser Gly Gly Gly Leu Val Gln Thr Gly Gly
  1               5                  10                  15

Ser Leu Arg Leu Ser Cys Ala Ala Ser Gly Phe Thr Phe Ser Asp Tyr
             20                  25                  30

Ala Met Ser Trp Val Arg Gln Ala Pro Gly Lys Gly Leu Glu Trp Val
         35                  40                  45

Ser Ser Ile Tyr Pro Asp Asp Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Arg Leu Val Asp Arg Trp Glu Glu Pro Ser Ser Asp Tyr
            100                 105                 110

Gly Met Asp Val Trp Gly Gln Gly Thr Leu Val Thr Val Ser Ser
        115                 120                 125

<210> SEQ ID NO 212
<211> LENGTH: 116
<212> TYPE: PRT
<213> ORGANISM: Artificial Sequence
<220> FEATURE:
<223> OTHER INFORMATION: Synthetic heavy chain variable region of
      anti-idiotype antibody (EW37) against anti-c-Met antibody

<400> SEQUENCE: 212

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Ser Met Ser Trp Val Arg Gln Ala Pro Gly Lys Gly Leu Glu Trp Val
         35                  40                  45

Ser Ser Ile Ser Ser Ser Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val His Leu Tyr Phe Asp Tyr Trp Gly Gln Gly Thr Leu Val
            100                 105                 110

Thr Val Ser Ser
        115

<210> SEQ ID NO 213
<211> LENGTH: 126
<212> TYPE: PRT
<213> ORGANISM: Artificial Sequence
<220> FEATURE:
<223> OTHER INFORMATION: Synthetic heavy chain variable region of
      anti-idiotype antibody (HAL 7-1) against anti-c-Met antibody

<400> SEQUENCE: 213
```

Gln Val Gln Leu Gln Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Asn Thr Arg Tyr Phe Glu Glu Pro Asn Tyr Tyr Gly
            100                 105                 110

Met Asp Val Trp Gly Gln Gly Thr Thr Val Thr Val Ser Ser
        115                 120                 125

<210> SEQ ID NO 214
<211> LENGTH: 124
<212> TYPE: PRT
<213> ORGANISM: Artificial Sequence
<220> FEATURE:
<223> OTHER INFORMATION: Synthetic heavy chain variable region of
      anti-idiotype antibody (HAL 7-2) against anti-c-Met antibody

<400> SEQUENCE: 214

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Asn Ser Tyr Tyr Glu Glu Pro Met Tyr Tyr Phe Asp
            100                 105                 110

Tyr Trp Gly Gln Gly Thr Leu Val Thr Val Ser Ser
        115                 120

<210> SEQ ID NO 215
<211> LENGTH: 124
<212> TYPE: PRT
<213> ORGANISM: Artificial Sequence
<220> FEATURE:
<223> OTHER INFORMATION: Synthetic heavy chain variable region of
      anti-idiotype antibody (HAL 7-5) against anti-c-Met antibody

<400> SEQUENCE: 215

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

```
Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Arg Asn Ser Tyr Tyr Glu Glu Pro Met Tyr Tyr Phe Asp
                100                 105                 110

Tyr Trp Gly Gln Gly Thr Leu Val Thr Val Ser Ser
        115                 120

<210> SEQ ID NO 216
<211> LENGTH: 124
<212> TYPE: PRT
<213> ORGANISM: Artificial Sequence
<220> FEATURE:
<223> OTHER INFORMATION: Synthetic heavy chain variable region of
      anti-idiotype antibody (HAL 7-7) against anti-c-Met antibody

<400> SEQUENCE: 216

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Val Ala Asp Asp Tyr Gly Asp Tyr Gly Thr Val Asp
                100                 105                 110

Tyr Trp Gly Gln Gly Thr Leu Val Thr Val Ser Ser
        115                 120

<210> SEQ ID NO 217
<211> LENGTH: 120
<212> TYPE: PRT
<213> ORGANISM: Artificial Sequence
<220> FEATURE:
<223> OTHER INFORMATION: Synthetic heavy chain variable region of
      anti-idiotype antibody (HAL 7-12) against anti-c-Met antibody

<400> SEQUENCE: 217

Gln Leu Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Lys Glu Arg Leu Glu Glu Pro Gly Phe Phe Asp Tyr Trp Gly Gln
            100                 105                 110

Gly Thr Leu Val Thr Val Ser Ser
        115                 120
```

<210> SEQ ID NO 218
<211> LENGTH: 128
<212> TYPE: PRT
<213> ORGANISM: Artificial Sequence
<220> FEATURE:
<223> OTHER INFORMATION: Synthetic heavy chain variable region of
      anti-idiotype antibody (HAL 8-7) against anti-c-Met antibody

<400> SEQUENCE: 218

```
Glu Val Gln Leu Val Glu Thr Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Gly Tyr Ser Tyr Gly Tyr Glu Glu Pro Tyr Tyr Tyr
            100                 105                 110

Tyr Gly Met Asp Val Trp Gly Gln Gly Thr Thr Val Thr Val Ser Ser
        115                 120                 125
```

<210> SEQ ID NO 219
<211> LENGTH: 381
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW01) against
      anti-c-Met antibody

<400> SEQUENCE: 219

```
gaggtgcagc tgttggagtc tgggggaggc ttggtacagc ctggggggtc cctgagactc      60
tcctgtgcag tctctggatt cacctttagc gattattata tgagctgggt ccgccaggct     120
ccagggaagg ggctggagtg ggtctcaggg atcattccta gtagtagtaa tatatattac     180
gctgattctg taaaaggtcg gttcaccatc tccagagaca attccgagaa cacgctgtat     240
ctgcaaatga acagcctgag agccgaggac acggccgtgt attactgtgc gaaagctctt     300
ggtaatcagg agaatgagcc gacttcttat tctaatggta tggacgtctg gggccaggt     360 acactggtca ccgtgagctc a                                                 381
```

<210> SEQ ID NO 220
<211> LENGTH: 348
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW02) against
      anti-c-Met antibody

<400> SEQUENCE: 220

```
gaggtgcagc tgttggagtc tgggggaggc ttggtacagc ctggggggtc cctgagactc    60
tcctgtgcag cctctggatt cacctttagc aattatgcta tgagctgggt ccgccaggct   120
ccagggaagg ggctggagtg ggtctcatcg atctcttcta gtggtggtaa tacatattac   180
gctgattctg taaaaggtcg gttcaccatc tccagagaca attccaagaa cacgctgtat   240
ctgcaaatga acagcctggg agccgaggac acggccgtgt attactgtgc gaaatatcat   300
tcggttttcg actactgggg ccagggtaca ctggtcaccg tgagctca                348
```

<210> SEQ ID NO 221
<211> LENGTH: 381
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW03) against
      anti-c-Met antibody

<400> SEQUENCE: 221

```
gaggtgcagc tgttggagtc cgggggaggc ttggtacagc ctggggggtc cctgagactc    60
tcctgtgcag cctctggatt cacctttagc gattatgata tgagctgggt ccgccaggct   120
ccagggaagg ggctggagtg ggtctcattg atctcttatg gtggtagtaa tacatattac   180
gctgattctg taaaaggtcg gttcaccatc tccagagaca attccaagaa cacgctgtat   240
ctgcaaatga acagcctgag agccgaggac acggccgtgt attactgtgc gaaatttcgt   300
agtgagttta tgagaatgaa gccgtcttct tattatggta tggacgtctg ggggccaggt   360
acactggtca ccgtgagctc a                                              381
```

<210> SEQ ID NO 222
<211> LENGTH: 381
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW06) against
      anti-c-Met antibody

<400> SEQUENCE: 222

```
gaggtgcagc tgttggagtc gggggaggc ttggtacagc ctggggggtc cctgagactc     60
tcctgtgcag cctctggatt cacctttagc ggttatgata tgagctgggt ccgccaggct   120
ccagggaagg ggctggagtg ggtctcaggg atctctcatg gtgatggtaa tatatattac   180
gctgattctg taaaaggtcg gttcaccatc tccagagaca attccaagaa cacgctgtat   240
ctgcaaatga acagcctgag agccgaggac acggccgtgt attactgtgc gaaagttggt   300 cttcttttg tgcaggagga gccgtcttat tataatgcta tggacgtctg ggggccaggt   360
acactggtca ccgtgagctc a                                              381
```

<210> SEQ ID NO 223
<211> LENGTH: 348
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW09) against
      anti-c-Met antibody

<400> SEQUENCE: 223

```
gaggtgcagc tgttggagtc tgggggaggc ttggtacagc ctggggggtc cctgagactc    60
tcctgtgcag cctctggatt cacctttagc gattatgata tgagctgggt ccgccaggct   120
```

```
ccagggaagg ggctggagtg ggtctcatcg atctcttatg gtggtggtag tatatattac      180
gctgattctg taaaaggtcg gttcaccatc tccagagaca attccaagaa cacgctgtat      240
ctgcaaatga acagcctgag agccgaggac acggccatgt attactgtgc gagagatgct      300
gcttatttcg actactgggg ccagggtaca ctggtcaccg tgagctca                   348
```

<210> SEQ ID NO 224
<211> LENGTH: 381
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW10) against
      anti-c-Met antibody

<400> SEQUENCE: 224

```
gaggtgcagc tgttggagtc tgggggaggc ttggtacagc ctggggggtc cctgagactc       60
tcctgtgcag cctctggatt caccttagc ggttatgata tgagctgggt ccgccaggct      120
ccagggaagg ggctggagtg ggtctcaggg atctcttata atggtggtag taaatattac      180
gctgattctg taaaaggtcg gttcaccatc tccagagaca attccaagaa cacgctgtat      240
ctgcaaatga acagcctgag agccgaggac acggccgtgt attactgtgc gaaatatctt      300
cttccggttc tggaggagcc ggggtattct gctgatggta tggacgtctg ggccagggt      360 acactggtca ccgtgagctc a                                                381
```

<210> SEQ ID NO 225
<211> LENGTH: 381
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW16) against
      anti-c-Met antibody

<400> SEQUENCE: 225

```
gaggtgcagc tgttggagtc tgggggaggc ttggtacagc ctggggggtc cctgagactc       60
tcctgtgcag cctctggatt caccttagc gattattata tgagctgggt ccgcctggct      120
ccagggaagg ggctggagtg ggtctcagcg atctctcata gtagtggtaa tacatattac      180
gctgattctg taaaaggtcg gttcaccatc tccagagaca attccaagaa cacgctgtat      240
ctgcaaatga acagcctgag agccgaggac acggccgtgt attactgtgc gaaacatctt      300
ggtgcgcagt cggatgagcc ggattcttct tctaatggta tggacgtctg ggccagggt      360 acactggtca ccgtgagctc a                                                381
```

<210> SEQ ID NO 226
<211> LENGTH: 381
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW26) against
      anti-c-Met antibody

<400> SEQUENCE: 226

```
gaggtgcagc tgttggagtc tgggggaggc ttggtacagc ctggggggtc cctgagactc       60
tcctgtgcag cctctggatt caccttagc aattatgcta tgagctgggt ccgccaggct      120
ccagggaagg ggctggagtg ggtctcagcg atctatcctg gtggtggtaa tacatattac      180
```

```
gctgattctg taaaaggtcg gttcaccatc tccagagaca attccaagaa cacgctgtat    240
ctgcaaatga acagcctgag agccgaggac acggccgtgt attactgtgc gaaatctctt    300
agtactcata gtgtggatga gccgtcttct gataatgcta tggacgtctg gggccaggt     360 acactggtca ccgtgagctc a                                              381
```

<210> SEQ ID NO 227
<211> LENGTH: 381
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW28) against
      anti-c-Met antibody

<400> SEQUENCE: 227

```
gaggtgcagc tgttggagtc tgggggaggc ttggtacaga ctggggggtc cctgagactc    60
tcctgtgcag tctctggatt caccttagc gattatgcta tgagctgggt ccgccaggct    120
ccagggaagg ggctggagtg ggtctcagcg atctcttctg gtgatggtaa tacatattac   180
gctgattctg taaaaggtcg gttcaccatc tccagagaca attccaagaa cacgctgtat   240
ctgcaaatga acagcctgag agccgaggac acggccgtgt attactgtgc gagatatctt   300
ggtactacga gtgatgagcc ggcttcttat tctaatggta tggacgtctg gggccagggt   360
acactggtca ccgtgagctc a                                             381
```

<210> SEQ ID NO 228
<211> LENGTH: 381
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW34) against
      anti-c-Met antibody

<400> SEQUENCE: 228

```
gaggtgcagc tgttggagtc tgggggaggc ttggtacaga ctggggggtc cctgagactc    60
tcctgtgcag cctctggatt caccttagc gattatgcta tgagctgggt ccgccaggct    120
ccagggaagg ggctggagtg ggtctcatcg atctatcctg atgatggtaa tacatattac   180
gctgattctg taaaaggtcg gttcaccatc tccagagaca attccaagaa cacgctgtat   240
ctgcaaatga acagcctgag agccgaggac acggccgtgt attactgtgc gaaatatcgt   300
cttgtggata ggtgggagga gccgtcttct gattatggta tggacgtctg gggccaggt    360 acactggtca ccgtgagctc a                                             381
```

<210> SEQ ID NO 229
<211> LENGTH: 348
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (EW37) against
      anti-c-Met antibody

<400> SEQUENCE: 229

```
gaggtgcagc tgttggagtc cggggggaggc ttggtacagc ctggggggtc cctgagactc   60
tcctgtgcag cctctggatt caccttagc aattattcta tgagctgggt ccgccaggct    120
ccagggaagg ggctggagtg ggtctcatcg atctcttcta gtggtggtaa tacatattac   180
gctgattctg taaaaggtcg gttcaccatc tccagagaca attccaagaa cacgctgtat   240
```

```
ctgcaaatga acagcctgag agccgaggac acggccgtgt attactgtgc gagagtgcat    300
ttgtatttcg actactgggg ccagggtaca ctggtcaccg tgagctca                 348
```

<210> SEQ ID NO 230
<211> LENGTH: 378
<212> TYPE: DNA
<213> ORGANISM: Artificial Sequence
<220> FEATURE:
<223> OTHER INFORMATION: Synthetic nucleic acid sequence encoding heavy chain variable region of anti-idiotype antibody (HAL7-1) against anti-c-Met antibody

<400> SEQUENCE: 230

```
caggtacagc tgcagcagtc aggggggaggc gtggtccagc ctgggaggtc cctgagactc    60
tcctgtgcag cctctggatt caccttcagt agctatgcta tgcactgggt ccgccaggct   120
ccaggcaagg ggctggagtg ggtggcagtt atatcatatg atggaagcaa taaatactac   180
gcagactccg tgaagggccg attcaccatc tccagagaca attccaagaa cacgctgtat   240
ctgcaaatga acagcctgag agctgaggac acggctgtgt attactgtgc gagagaggat   300
aatacgcgat attttgaaga accgaactac tacggtatgg acgtctgggg ccaagggacc   360
acggtcaccg tctcctca                                                 378
```

<210> SEQ ID NO 231
<211> LENGTH: 372
<212> TYPE: DNA
<213> ORGANISM: Artificial Sequence
<220> FEATURE:
<223> OTHER INFORMATION: Synthetic nucleic acid sequence encoding heavy chain variable region of anti-idiotype antibody (HAL7-2) against anti-c-Met antibody

<400> SEQUENCE: 231

```
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagagatcgt   300
aatagctact acgaggagcc aatgtactac tttgactact ggggccaggg aaccctggtc   360
accgtctcct ca                                                       372
```

<210> SEQ ID NO 232
<211> LENGTH: 372
<212> TYPE: DNA
<213> ORGANISM: Artificial Sequence
<220> FEATURE:
<223> OTHER INFORMATION: Synthetic nucleic acid sequence encoding heavy chain variable region of anti-idiotype antibody (HAL7-5) against anti-c-Met antibody

<400> SEQUENCE: 232

```
caggttcagc tggtgcagtc tggagctgag gtgaagaagc ctggggcctc agtgaaggtc    60
tcctgcaagg cttctggagg caccttcagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagagatcgt   300
```

```
aatagctact acgaggagcc aatgtactac tttgactact ggggccaggg aaccctggtc    360
accgtctcct ca                                                         372
```

<210> SEQ ID NO 233
<211> LENGTH: 372
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (HAL7-7) against
      anti-c-Met antibody

<400> SEQUENCE: 233

```
caggtgcagc tggtggagtc tgggggaggc gtggtccagc ctggagggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gagagatctc   300
gtcgccgatg actacggtga ctacgggacc gttgactact ggggccaggg aaccctggtc   360
accgtctcct ca                                                        372
```

<210> SEQ ID NO 234
<211> LENGTH: 360
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (HAL7-12) against
      anti-c-Met antibody

<400> SEQUENCE: 234

```
cagctgcagc ttcaggagtc gggggggaggc ttggtacagc ctgggggtc cctgagactc    60 tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tggagggccg gttcaccatc tccagagaca attccaagaa cacgctgtat   240
ctgcaaatga acagcctgag agccgaggac acggccgtat attactgtgc gaaagagagg   300
cttgaggagc ccggtttctt tgattactgg ggccagggaa ccctggtcac cgtctcctca   360
```

<210> SEQ ID NO 235
<211> LENGTH: 384
<212> TYPE: DNA
<213> ORGANISM: Artificial Sequence
<220> FEATURE:
<223> OTHER INFORMATION: Synthetic nucleic acid sequence encoding heavy
      chain variable region of anti-idiotype antibody (HAL8-7) against
      anti-c-Met antibody

<400> SEQUENCE: 235

```
gaggtgcagc tggtggagac tgggggaggc ttggtacagc ctgggggtc cctgagactc    60 tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggctgtgt attactgtgc gagagggggt   300
ggatacagct atggttacga ggaaccctac tactactacg gtatggacgt ctggggccaa   360
gggaccacgg tcaccgtctc ctca                                           384
```

<210> SEQ ID NO 236
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW01) antibody against anti-c-Met antibody

<400> SEQUENCE: 236

```
Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Asn Asn
                 20                  25                  30

Ser Val Tyr Trp Tyr Gln Gln Leu Pro Gly Thr Ala Pro Lys Leu Leu
             35                  40                  45

Ile Tyr Ser Asp Ser Gln Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Tyr Ser Leu
                 85                  90                  95

Asn Gly Tyr Val Phe Gly Gly Gly Thr Lys Leu Thr Val Leu Gly
            100                 105                 110
```

<210> SEQ ID NO 237
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW02) antibody against anti-c-Met antibody

<400> SEQUENCE: 237

```
Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Asn Asn
                 20                  25                  30

Tyr Val Tyr Trp Tyr Gln Gln Leu Pro Gly Thr Ala Pro Lys Leu Leu
             35                  40                  45

Ile Tyr Ala Asn Asn Gln Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Asp Ser Leu
                 85                  90                  95

Ser Gly Tyr Val Phe Gly Gly Gly Thr Lys Leu Thr Val Leu Gly
            100                 105                 110
```

<210> SEQ ID NO 238
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW03) antibody against anti-c-Met antibody

<400> SEQUENCE: 238

```
Gln Ser Val Leu Thr Gln Pro Pro Ser Ala Ser Gly Thr Pro Gly Gln
  1               5                  10                  15
```

```
Arg Val Thr Ile Ser Cys Ser Gly Ser Ser Asn Ile Gly Asn Asn
             20                  25                  30

Asp Val Thr Trp Tyr Gln Gln Leu Pro Gly Thr Ala Pro Lys Leu Leu
         35                  40                  45

Ile Tyr Ser Asp Ser Asn Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Ser Ser Leu
                 85                  90                  95

Ser Ala Tyr Val Phe Gly Gly Gly Thr Lys Leu Thr Val Leu Gly
            100                 105                 110
```

<210> SEQ ID NO 239
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW06) antibody against anti-c-Met antibody

<400> SEQUENCE: 239

```
Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ser Asn
             20                  25                  30

Asn Val Thr Trp Tyr Gln Gln Leu Pro Gly Thr Ala Pro Lys Leu Leu
         35                  40                  45

Ile Tyr Ser Asn Ser His Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Gly Ala Asp Tyr Tyr Cys Gly Thr Trp Asp Asp Ser Leu
                 85                  90                  95

Asn Gly Tyr Val Phe Gly Gly Gly Thr Lys Leu Thr Val Leu Gly
            100                 105                 110
```

<210> SEQ ID NO 240
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW09) antibody against anti-c-Met antibody

<400> SEQUENCE: 240

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Asn Asn
             20                  25                  30

Ser Val Asn Trp Tyr Gln Gln Leu Pro Gly Thr Ala Pro Lys Leu Leu
         35                  40                  45

Ile Tyr Ala Asn Asn Asn Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ala Ser Leu
                 85                  90                  95
```

```
Asn Gly Tyr Val Phe Gly Gly Gly Thr Lys Leu Thr Val Leu Gly
            100                 105                 110
```

<210> SEQ ID NO 241
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW10) antibody against anti-c-Met antibody

<400> SEQUENCE: 241

```
Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ser Asn
                20                  25                  30

Tyr Val Ser Trp Tyr Arg Gln Leu Pro Gly Thr Ala Pro Lys Leu Leu
            35                  40                  45

Ile Tyr Ser Asp Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Ala Ser Leu
                85                  90                  95

Ser Ala Tyr Val Phe Gly Gly Gly Thr Lys Leu Thr Val Leu Gly
            100                 105                 110
```

<210> SEQ ID NO 242
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW16) antibody against anti-c-Met antibody

<400> SEQUENCE: 242

```
Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Asn Asn
                20                  25                  30

Asp Val Tyr Trp Tyr Gln Gln Leu Pro Gly Thr Ala Pro Lys Leu Leu
            35                  40                  45

Ile Tyr Ser Asp Ser Asn Arg Pro Ser Gly Ile Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Asp Ser Leu
                85                  90                  95

Asn Gly Tyr Val Phe Gly Gly Gly Thr Lys Leu Thr Val Leu Gly
            100                 105                 110
```

<210> SEQ ID NO 243
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW26) antibody against anti-c-Met antibody

<400> SEQUENCE: 243

```
Gln Ser Val Leu Thr Gln Pro Pro Ser Ala Ser Gly Thr Pro Gly Gln
```

```
                1               5                      10                     15
Arg Val Thr Ile Ser Cys Thr Gly Ser Ser Ser Asn Ile Gly Ser Asn
                        20                     25                     30

Ser Val Ser Trp Tyr Gln Gln Leu Pro Gly Thr Ala Pro Lys Leu Leu
                        35                     40                     45

Ile Tyr Asp Asp Ser Asn Arg Pro Ser Gly Val Pro Asp Arg Phe Ser
        50                     55                     60

Gly Ser Lys Ser Gly Thr Ser Ala Ser Leu Ala Ile Ser Gly Leu Arg
 65                             70                     75                     80

Ser Glu Asp Glu Ala Asp Tyr Tyr Cys Ala Ser Trp Asp Tyr Ser Leu
                        85                     90                     95

Asn Ala Tyr Val Phe Gly Gly Gly Thr Lys Leu Thr Val Leu Gly
                100                    105                    110
```

<210> SEQ ID NO 244
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW28) antibody against anti-c-Met antibody

<400> SEQUENCE: 244

```
Gln Ser Val Leu Thr Gln Pro Pro Ser Ala Ser Gly Thr Pro Gly Gln
 1               5                      10                     15

Arg Val Thr Ile Ser Cys Ser Gly Ser Ser Ser Asn Ile Gly Ser Asn
                        20                     25                     30

Asp Val Tyr Trp Tyr Gln Gln Leu Pro Gly Thr Ala Pro Lys Leu Leu
                        35                     40                     45

Ile Tyr Ser Asp Asn Asn Arg Pro Ser Gly Val Pro Asp Arg Phe Ser
        50                     55                     60

Gly Ser Lys Ser Gly Thr Ser Ala Ser Leu Ala Ile Ser Gly Leu Arg
 65                             70                     75                     80

Ser Glu Asp Glu Ala Asp Tyr Tyr Cys Gly Ala Trp Asp Asp Ser Leu
                        85                     90                     95

Ser Gly Tyr Val Phe Gly Gly Gly Thr Lys Leu Thr Val Leu Gly
                100                    105                    110
```

<210> SEQ ID NO 245
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW34) antibody against anti-c-Met antibody

<400> SEQUENCE: 245

```
Gln Ser Val Leu Thr Gln Pro Pro Ser Ala Ser Gly Thr Pro Gly Gln
 1               5                      10                     15

Arg Val Thr Ile Ser Cys Thr Gly Ser Ser Ser Asn Ile Gly Ser Asn
                        20                     25                     30

Asn Val Asn Trp Tyr Gln Gln Leu Pro Gly Thr Ala Pro Lys Leu Leu
                        35                     40                     45

Ile Tyr Ala Asp Ser Gln Arg Pro Ser Gly Val Pro Asp Arg Phe Ser
        50                     55                     60

Gly Pro Lys Ser Gly Thr Ser Ala Ser Leu Ala Ile Ser Gly Leu Arg
 65                             70                     75                     80

Ser Glu Asp Glu Ala Asp Tyr Tyr Cys Gly Ser Trp Asp Ser Ser Leu
```

```
                    85                  90                  95
Ser Gly Tyr Val Leu Gly Gly Gly Thr Lys Leu Thr Val Leu Gly
                100                 105                 110

<210> SEQ ID NO 246
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (EW37) antibody against anti-c-Met antibody

<400> SEQUENCE: 246

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Ser Asn
                 20                  25                  30

Ser Val Asn Trp Tyr Gln Gln Leu Pro Gly Thr Ala Pro Lys Leu Leu
             35                  40                  45

Ile Tyr Ser Asp Ser His Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Asp Ser Leu
                 85                  90                  95

Ser Gly Tyr Val Phe Gly Gly Gly Thr Lys Leu Thr Val Leu Gly
                100                 105                 110

<210> SEQ ID NO 247
<211> LENGTH: 112
<212> TYPE: PRT
<213> ORGANISM: Artificial Sequence
<220> FEATURE:
<223> OTHER INFORMATION: Synthetic light chain variable region of
      anti-idiotype (HAL7-1) antibody against anti-c-Met antibody

<400> SEQUENCE: 247

Gln Ala Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Ala
                 20                  25                  30

Tyr Glu Val His Trp Tyr Gln Gln Leu Pro Gly Thr Ala Pro Lys Leu
             35                  40                  45

Leu Ile Tyr Asp Thr Ser Asn Arg Pro Ser Gly Val Pro Asp Arg Phe
         50                  55                  60

Ser Gly Ser Lys Ser Gly Thr Ser Ala Ser Leu Ala Ile Ser Gly Leu
 65                  70                  75                  80

Gln Ser Glu Asp Glu Ala Leu Tyr Tyr Cys Ala Ala Trp Asp Asp Ser
                 85                  90                  95

Leu Asn Gly Pro Val Phe Arg Arg Asp Lys Leu Thr Val Leu Gly
                100                 105                 110

<210> SEQ ID NO 248
<211> LENGTH: 109
<212> TYPE: PRT
<213> ORGANISM: Artificial Sequence
<220> FEATURE:
<223> OTHER INFORMATION: Synthetic light chain variable region of
      anti-idiotype (HAL7-2) antibody against anti-c-Met antibody

<400> SEQUENCE: 248
```

```
Gln Ala Gly Leu Thr Gln Pro Pro Ser Val Ser Val Ser Pro Gly Gln
1               5                   10                  15

Thr Ala Ser Ile Thr Cys Ser Gly Asp Lys Leu Gly Asp Arg Tyr Val
            20                  25                  30

Phe Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asp Thr Ala Thr Leu Thr Ile Ser Arg Val Glu Ala Gly
65                  70                  75                  80

Asp Glu Ala Asp Tyr Tyr Cys Gln Val Trp Asp Ser Val Asn Asp His
                85                  90                  95

Pro Val Phe Gly Gly Gly Thr Lys Leu Thr Val Leu Gly
            100                 105

<210> SEQ ID NO 249
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (HAL7-5) antibody against anti-c-Met antibody

<400> SEQUENCE: 249

Gln Leu Val Leu Thr Gln Ser Ser Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Asn Trp Tyr Gln Gln Leu Pro Gly Ala Ala Pro Lys Leu Leu
        35                  40                  45

Ile His Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Pro Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110

<210> SEQ ID NO 250
<211> LENGTH: 109
<212> TYPE: PRT
<213> ORGANISM: Artificial Sequence
<220> FEATURE:
<223> OTHER INFORMATION: Synthetic light chain variable region of
      anti-idiotype (HAL7-7) antibody against anti-c-Met antibody

<400> SEQUENCE: 250

Gln Ser Val Leu Thr Gln Pro Pro Ser Val Ser Met Ala Pro Gly Gln
1               5                   10                  15

Thr Ala Arg Ile Thr Cys Gly Gly Asn Asn Ile Ala Thr Lys Gly Val
            20                  25                  30

His Trp Tyr Gln Gln Lys Ala Gly Gln Ala Pro Val Leu Val Val Tyr
        35                  40                  45

Asp Asp Ser Gly Arg Pro Ser Gly Ile Pro Asp Arg Phe Ser Gly Ser
    50                  55                  60

Lys Ser Gly Asn Thr Ala Thr Leu Thr Ile Ser Arg Val Glu Ala Gly
65                  70                  75                  80
```

```
Asp Glu Ala Asp Tyr Tyr Cys Gln Leu Trp Asp Gly Arg Ser Asp Gln
                85                  90                  95

Val Leu Phe Gly Gly Gly Thr Lys Leu Thr Val Leu Gly
            100                 105
```

<210> SEQ ID NO 251
<211> LENGTH: 111
<212> TYPE: PRT
<213> ORGANISM: Artificial Sequence
<220> FEATURE:
<223> OTHER INFORMATION: Synthetic light chain variable region of
      anti-idiotype (HAL7-12) antibody against anti-c-Met antibody

<400> SEQUENCE: 251

```
Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala His Tyr Tyr Cys Ser Ser Tyr Thr Thr Asp
                85                  90                  95

Asn Ala Trp Val Phe Gly Gly Gly Thr Gln Leu Thr Val Leu Gly
            100                 105                 110
```

<210> SEQ ID NO 252
<211> LENGTH: 114
<212> TYPE: PRT
<213> ORGANISM: Artificial Sequence
<220> FEATURE:
<223> OTHER INFORMATION: Synthetic light chain variable region of
      anti-idiotype (HAL8-7) antibody against anti-c-Met antibody

<400> SEQUENCE: 252

```
Ala Ile Gln Leu Thr Gln Ser Pro Leu Ser Leu Ser Val Ser Ala Gly
  1               5                  10                  15

Glu Lys Val Thr Met Ser Cys Lys Ser Ser Gln Ser Leu Leu Asn Ser
                20                  25                  30

Gly Asn Gln Lys Asn Asp Leu Ala Trp Tyr Gln Gln Lys Pro Gly Gln
            35                  40                  45

Arg Pro Lys Leu Leu Ile Tyr Gly Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Ile
            100                 105                 110

Lys Arg
```

<210> SEQ ID NO 253
<211> LENGTH: 333
<212> TYPE: DNA
<213> ORGANISM: Artificial Sequence
<220> FEATURE:

<223> OTHER INFORMATION: Synthetic nucleic acid sequence encoding light
      chain variable region of anti-idiotype antibody (EW01) against
      anti-c-Met antibody

<400> SEQUENCE: 253
cagtctgtgc tgactcagcc accctcagcg tctgggaccc ccgggcagag ggtcaccatc    60
tcttgtagtg gctcttcatc taatattggc aataattctg tctactggta ccagcagctc   120
ccaggaacgg cccccaaact cctcatctat tctgatagtc agcggccaag cggggtccct   180
gaccgattct ctggctccaa gtctggcacc tcagcctccc tggccatcag tgggctccgg   240
tccgaggatg aggctgatta ttactgtggt acttgggatt atagcctgaa tggttatgtc   300
ttcggcggag gcaccaagct tacggtccta ggc                                333

<210> SEQ ID NO 254
<211> LENGTH: 333
<212> TYPE: DNA
<213> ORGANISM: Artificial Sequence
<220> FEATURE:
<223> OTHER INFORMATION: Synthetic nucleic acid sequence encoding light
      chain variable region of anti-idiotype antibody (EW02) against
      anti-c-Met antibody

<400> SEQUENCE: 254
cagtctgtgc tgactcagcc accctcagcg tctgggaccc ccgggcagag ggtcaccatc    60
tcttgtagtg gctcttcatc taatattggc aataattatg tctactggta ccagcagctc   120
ccaggaacgg cccccaaact cctcatctat gctaataatc agcggccaag cggggtccct   180
gaccgattct ctggctccaa gtctggcacc tcagcctccc tggccatcag tgggctccgg   240
tccgaggatg aggctgatta ttactgtggt gcttgggatg atagcctgag tggttatgtc   300
ttcggcggag gcaccaagct gacggtccta ggc                                333

<210> SEQ ID NO 255
<211> LENGTH: 333
<212> TYPE: DNA
<213> ORGANISM: Artificial Sequence
<220> FEATURE:
<223> OTHER INFORMATION: Synthetic nucleic acid sequence encoding light
      chain variable region of anti-idiotype antibody (EW03) against
      anti-c-Met antibody

<400> SEQUENCE: 255
cagtctgtgc tgactcagcc accctcagcg tctgggaccc ccgggcagag ggtcaccatc    60
tcttgtagtg gctcttcatc taatattggc aataatgatg tcacctggta ccagcagctc   120
ccaggaacgg cccccaaact cctcatctat tctgatagta atcggccaag cggggtccct   180
gaccgattct ctggctccaa gtctggcacc tcagcctccc tggccatcag tgggctccgg   240
tccgaggatg aggctgatta ttactgtggt acttgggatt ctagcctgag tgcttatgtc   300
ttcggcggag gcaccaagct gacggtccta ggc                                333

<210> SEQ ID NO 256
<211> LENGTH: 333
<212> TYPE: DNA
<213> ORGANISM: Artificial Sequence
<220> FEATURE:
<223> OTHER INFORMATION: Synthetic nucleic acid sequence encoding light
      chain variable region of anti-idiotype antibody (EW06) against
      anti-c-Met antibody

<400> SEQUENCE: 256
cagtctgtgc tgactcagcc accctcagcg tctgggaccc ccgggcagag ggtcaccatc    60

```
tcttgtactg gctcttcatc taatattggc agtaataatg tcacctggta ccagcagctc      120
ccaggaacgg cccccaaact cctcatctat tctaatagtc atcggccaag cggggtccct      180
gaccgattct ctggctccaa gtctggcacc tcagcctccc tggccatcag tgggctccgg      240
tccgaggatg gggctgatta ttactgtggt acttgggatg atagcctgaa tggttatgtc      300
ttcggcggag gcaccaagct gacggtccta ggc                                   333
```

<210> SEQ ID NO 257
<211> LENGTH: 333
<212> TYPE: DNA
<213> ORGANISM: Artificial Sequence
<220> FEATURE:
<223> OTHER INFORMATION: Synthetic nucleic acid sequence encoding light
    chain variable region of anti-idiotype antibody (EW09) against
    anti-c-Met antibody

<400> SEQUENCE: 257

```
cagtctgtgc tgactcagcc accctcagcg tctgggaccc ccgggcagag ggtcaccatc       60
tcttgtagtg gctcttcatc taatattggc aataattctg tcaactggta ccagcagctc      120
ccaggaacgg cccccaaact cctcatctat gctaataata atcggccaag cggggtccct      180
gaccgattct ctggctccaa gtctggcacc tcagcctccc tggccatcag tgggctccgg      240
tccgaggatg aggctgatta ttactgtggt gcttgggatg ctagcctgaa tggttatgtc      300
ttcggcggag gcaccaagct gacggtccta ggc                                   333
```

<210> SEQ ID NO 258
<211> LENGTH: 333
<212> TYPE: DNA
<213> ORGANISM: Artificial Sequence
<220> FEATURE:
<223> OTHER INFORMATION: Synthetic nucleic acid sequence encoding light
    chain variable region of anti-idiotype antibody (EW10) against
    anti-c-Met antibody

<400> SEQUENCE: 258

```
cagtctgtgc tgactcagcc accctcagcg tctgggaccc ccgggcagag ggtcaccatc       60
tcttgtactg gctcttcatc taatattggc agtaattatg tctcctggta ccggcagctc      120
ccaggaacgg cccccaaact cctcatctat tctgatagta atcggccaag cggggtccct      180
gaccgattct ctggctccaa gtctggcacc tcagcctccc tggccatcag tgggctccgg      240
tccgaggatg aggctgatta ttactgtgct acttgggatg ctagcctgag tgcttatgtc      300
ttcggcggag gcaccaagct gacggtccta ggc                                   333
```

<210> SEQ ID NO 259
<211> LENGTH: 333
<212> TYPE: DNA
<213> ORGANISM: Artificial Sequence
<220> FEATURE:
<223> OTHER INFORMATION: Synthetic nucleic acid sequence encoding light
    chain variable region of anti-idiotype antibody (EW16) against
    anti-c-Met antibody

<400> SEQUENCE: 259

```
cagtctgtgc tgactcagcc accctcagcg tctgggaccc ccgggcagag ggtcaccatc       60
tcttgtactg gctcttcatc taatattggc aataatgatg tctactggta ccagcagctc      120
ccaggaacgg cacccaaact cctcatctat tctgatagta atcggccaag cgggatccct      180
gaccgattct ctggctccaa gtctggcacc tcagcctccc tggccatcag tgggctccgg      240
```

```
tccgaggatg aggctgatta ttactgtggt acttgggatg atagcctgaa tggttatgtc    300
ttcggcggag gcaccaagct gacggtccta ggc                                 333
```

<210> SEQ ID NO 260
<211> LENGTH: 333
<212> TYPE: DNA
<213> ORGANISM: Artificial Sequence
<220> FEATURE:
<223> OTHER INFORMATION: Synthetic nucleic acid sequence encoding light
      chain variable region of anti-idiotype antibody (EW26) against
      anti-c-Met antibody

<400> SEQUENCE: 260

```
cagtctgtgc tgactcagcc accctcagcg tctgggaccc ccgggcagag ggtcaccatc    60
tcttgtactg gctcttcatc taatattggc agtaattctg tctcctggta ccagcagctc    120
ccaggaacgg cccccaaact cctcatctat gatgatagta tcggccaag cggggtccct    180 gaccgattct ctggctccaa gtctggcacc tcagcctccc tggccatcag tgggctccgg    240
tccgaggatg aggctgatta ttactgtgct tcttgggatt atagcctgaa tgcttatgtc    300
ttcggcggag gcaccaagct gacggtccta ggc                                 333
```

<210> SEQ ID NO 261
<211> LENGTH: 333
<212> TYPE: DNA
<213> ORGANISM: Artificial Sequence
<220> FEATURE:
<223> OTHER INFORMATION: Synthetic nucleic acid sequence encoding light
      chain variable region of anti-idiotype antibody (EW28) against
      anti-c-Met antibody

<400> SEQUENCE: 261

```
cagtctgtgc tgactcagcc accctcagcg tctgggaccc ccgggcagag ggtcaccatc    60
tcttgtagtg gctcttcatc taatattggc agtaatgatg tctactggta ccagcagctc    120
ccaggaacgg cccccaaact cctcatctat tctgataata tcggccaag cggggtccct    180 gaccgattct ctggctccaa gtctggcacc tcagcctccc tggccatcag tgggctccgg    240
tccgaggatg aggctgatta ttactgtggt gcttgggatg atagcctgag tggttatgtc    300
ttcggcggag gcaccaagct gacggtccta ggc                                 333
```

<210> SEQ ID NO 262
<211> LENGTH: 333
<212> TYPE: DNA
<213> ORGANISM: Artificial Sequence
<220> FEATURE:
<223> OTHER INFORMATION: Synthetic nucleic acid sequence encoding light
      chain variable region of anti-idiotype antibody (EW34) against
      anti-c-Met antibody

<400> SEQUENCE: 262

```
cagtctgtgc tgactcagcc accctcagcg tctgggaccc ccgggcagag ggtcaccatc    60
tcttgtactg gctcttcatc taatattggc agtaataatg tcaactggta ccagcagctc    120
ccaggaacgg cccccaaact cctcatctat gctgatagtc agcggccaag cggggtccct    180
gaccgattct ctggcccaa gtctggcacc tcagcctccc tggccatcag tgggctccgg    240
tccgaggatg aggctgatta ttactgtggt tcttgggatt ctagcctgag tggttatgtc    300
ttaggcggag gcaccaagct gacggtccta ggc                                 333
```

<210> SEQ ID NO 263
<211> LENGTH: 333

<210> SEQ ID NO 263
<211> LENGTH: 333
<212> TYPE: DNA
<213> ORGANISM: Artificial Sequence
<220> FEATURE:
<223> OTHER INFORMATION: Synthetic nucleic acid sequence encoding light
chain variable region of anti-idiotype antibody (EW37) against
anti-c-Met antibody

<400> SEQUENCE: 263

```
cagtctgtgc tgactcagcc accctcagcg tctgggaccc ccgggcagag ggtcaccatc      60
tcttgtagtg gctcttcatc taatattggc agtaattctg tcaactggta ccagcagctc     120
ccaggaacgg cccccaaact cctcatctat tctgatagtc atcggccaag cggggtccct     180
gaccgattct ctggctccaa gtctggcacc tcagcctccc tggccatcag tgggctccgg     240
tccgaggatg aggctgatta ttactgtggt tcttgggatg atagcctgag tggttatgtc     300
ttcggcggag gcaccaagct gacggtccta ggc                                  333
```

<210> SEQ ID NO 264
<211> LENGTH: 336
<212> TYPE: DNA
<213> ORGANISM: Artificial Sequence
<220> FEATURE:
<223> OTHER INFORMATION: Synthetic nucleic acid sequence encoding light
chain variable region of anti-idiotype antibody (HAL7-1) against
anti-c-Met antibody

<400> SEQUENCE: 264

```
caggctgtgc tgactcagcc accctcagtg tctggggccc cagggcagag ggtcaccatc      60
tcctgcactg ggagcagctc caacatcggg gcagcttatg aggtgcattg gtatcagcag     120
cttccaggaa cagcccccaa acttctcatt tatgatactt ccaatcggcc ctcagggggtc     180 cctgaccgat tctctggctc caagtctggc acctcagcct ccctggccat cagtgggctc     240
cagtctgagg atgaggctct ttattactgt gcagcatggg atgacagcct gaatggtccg     300
gtctttcggc ggagggacaa gctgaccgtc ctaggt                                336
```

<210> SEQ ID NO 265
<211> LENGTH: 327
<212> TYPE: DNA
<213> ORGANISM: Artificial Sequence
<220> FEATURE:
<223> OTHER INFORMATION: Synthetic nucleic acid sequence encoding light
chain variable region of anti-idiotype antibody (HAL7-2) against
anti-c-Met antibody

<400> SEQUENCE: 265

```
caggcagggc tgactcagcc accctcagtg tccgtgtccc caggacaaac agccagcata      60
acctgctctg gagataaatt gggggataga tatgttttct ggtatcagca gaagccaggc     120
caggcccctg tgctggtcgt ccatgatgat agcgaccggc cctcagggat ccctgagcga     180
ttctctggct ccaactctgg ggacacggcc accctgacca tcagcagggt cgaggccggg     240
gatgaggccg actattactg tcaggtgtgg gatagtgtta atgatcatcc ggtgttcggc     300
ggagggacca agctgaccgt cctaggt                                         327
```

<210> SEQ ID NO 266
<211> LENGTH: 333
<212> TYPE: DNA
<213> ORGANISM: Artificial Sequence
<220> FEATURE:
<223> OTHER INFORMATION: Synthetic nucleic acid sequence encoding light
chain variable region of anti-idiotype antibody (HAL7-5) against
anti-c-Met antibody

<400> SEQUENCE: 266

```
cagcttgtgc tgactcaatc atcgtcagcg tctgggaccc ccgggcagag ggtcaccatc      60
tcttgttctg gaagcggctc caacatcgga agtaatgctg taaactggta ccagcagctc     120
ccaggagcgg cccccaaact cctcatccat agtaataatc agcggccctc agggtccct      180 gaccgattct ctggctccaa gtctggcacg tcagcctccc tggccatcag tgggcccag     240 tcagaggatg aggctgacta ttactgtgca gcttgggatg acagtttgaa tggtgtggtt    300
ttcggcggag ggaccaagct gaccgtcctc ggt                                  333
```

<210> SEQ ID NO 267
<211> LENGTH: 327
<212> TYPE: DNA
<213> ORGANISM: Artificial Sequence
<220> FEATURE:
<223> OTHER INFORMATION: Synthetic nucleic acid sequence encoding light
chain variable region of anti-idiotype antibody (HAL7-7) against
anti-c-Met antibody

<400> SEQUENCE: 267

```
cagtctgtgc tgactcagcc accctcggtg tcaatggccc caggacagac ggccaggatc      60
acctgtgggg gaaacaacat tgcaactaaa ggtgtgcact ggtaccagca gaaggcaggc     120
caggcccctg tgctggtcgt ctatgatgat agcggccggc cctcagggat ccctgaccga     180
ttctctggct ccaagtctgg gaacacggcc accctgacca tcagcagggt cgaagccggg     240
gatgaggccg actattactg tcagctgtgg gatggtagga gtgatcaagt gctattcggc     300
ggagggacca gctgaccgt cctaggt                                          327
```

<210> SEQ ID NO 268
<211> LENGTH: 333
<212> TYPE: DNA
<213> ORGANISM: Artificial Sequence
<220> FEATURE:
<223> OTHER INFORMATION: Synthetic nucleic acid sequence encoding light
chain variable region of anti-idiotype antibody (HAL7-12) against
anti-c-Met antibody

<400> SEQUENCE: 268

```
cagtctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca aagcccccaa actcatgatt tatgaggtca gtaatcggcc ctcaggggtt     180
tctaatcgct tctctggctc caagtctggc aacacggcct ccctgaccat ctctgggctc     240
caggctgagg acgaggctca ttattattgc agctcatata aaccgacaa cgcttgggtg     300 ttcggcggag ggacccagct gaccgtcctg ggt                                  333
```

<210> SEQ ID NO 269
<211> LENGTH: 342
<212> TYPE: DNA
<213> ORGANISM: Artificial Sequence
<220> FEATURE:
<223> OTHER INFORMATION: Synthetic nucleic acid sequence encoding light
chain variable region of anti-idiotype antibody (HAL8-7) against
anti-c-Met antibody

<400> SEQUENCE: 269

```
gccatccagt tgacccagtc tccactctcc ctaagtgtgt cagcaggaga gaaggtcact      60
atgagctgca gtccagtca gagtctgtta aacagtggaa atcaaaagaa cgacttggcc      120
tggtaccagc agaaaccagg gcaacgtcct aaactgttga tctacggggc atccactagg     180
```

```
gaatctgggg tccctgatcg cttcacaggc agtggatctg gaaccgattt cactcttacc    240
atcagcagtg tgcaggctga agacctggca gtttattact gtcagaatga tcatagttat    300
ccgttaacgt tcggtgctgg caccaagctg gaaatcaaac gt                       342
```

<210> SEQ ID NO 270
<211> LENGTH: 330
<212> TYPE: PRT
<213> ORGANISM: Artificial Sequence
<220> FEATURE:
<223> OTHER INFORMATION: Synthetic heavy chain constant region of anti-idiotype antibody against anti-c-Met antibody

<400> SEQUENCE: 270

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 271
<211> LENGTH: 990
<212> TYPE: DNA
<213> ORGANISM: Artificial Sequence
<220> FEATURE:
<223> OTHER INFORMATION: Synthetic nucleic acid sequence encoding heavy chain constant region of anti-idiotype antibody against anti-c-Met antibody

<400> SEQUENCE: 271

```
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990
```

<210> SEQ ID NO 272
<211> LENGTH: 104
<212> TYPE: PRT
<213> ORGANISM: Artificial Sequence
<220> FEATURE:
<223> OTHER INFORMATION: Synthetic light chain constant region of anti-idiotype antibody against anti-c-Met antibody

<400> SEQUENCE: 272

```
Gln Pro Lys Ala Ala Pro Ser Val Thr Leu Phe Pro Pro Ser Ser Glu
  1               5                  10                  15

Glu Leu Gln Ala Asn Lys Ala Thr Leu Val Cys Leu Ile Ser Asp Phe
             20                  25                  30

Tyr Pro Gly Ala Val Thr Val Ala Trp Lys Ala Asp Ser Ser Pro Val
         35                  40                  45

Lys Ala Gly Val Glu Thr Thr Thr Pro Ser Lys Gln Ser Asn Asn Lys
     50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys
            100
```

<210> SEQ ID NO 273
<211> LENGTH: 312
<212> TYPE: DNA
<213> ORGANISM: Artificial Sequence
<220> FEATURE:
<223> OTHER INFORMATION: Synthetic nucleic acid sequence encoding light
chain constant region of anti-idiotype antibody against anti-c-Met
antibody

<400> SEQUENCE: 273

```
cagcccaagg ctgcccccctc ggtcactctg ttcccgccct cctctgagga gcttcaagcc    60
aacaaggcca cactggtgtg tctcataagt gacttctacc cgggagccgt gacagtggcc   120
tggaaggcag atagcagccc cgtcaaggcg ggagtggaga ccaccacacc ctccaaacaa   180
agcaacaaca gtacgcggc cagcagctac ctgagcctga cgcccgagca gtggaagtcc    240
cacagaagct acagctgcca ggtcacgcat gaagggagca ccgtggagaa gacagtggcc   300
cctacagaat gt                                                       312
```

<210> SEQ ID NO 274
<211> LENGTH: 106
<212> TYPE: PRT
<213> ORGANISM: Artificial Sequence
<220> FEATURE:
<223> OTHER INFORMATION: Synthetic light chain constant region of
anti-idiotype antibody (HAL8-7) against anti-c-Met antibody

<400> SEQUENCE: 274

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 275
<211> LENGTH: 318
<212> TYPE: DNA
<213> ORGANISM: Artificial Sequence
<220> FEATURE:
<223> OTHER INFORMATION: Synthetic nucleic acid sequence encoding light
chain constant region of anti-idiotype antibody (HAL8-7) against
anti-c-Met antibody

<400> SEQUENCE: 275

```
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat caggggcctga gctcgcccgt cacaaagagc   300
```

```
ttcaacaggg gagagtgt                                              318

<210> SEQ ID NO 276
<211> LENGTH: 114
<212> TYPE: PRT
<213> ORGANISM: Artificial Sequence
<220> FEATURE:
<223> OTHER INFORMATION: Synthetic Synthetic (light chain variable
      region of anti c-Met antibody)

<400> SEQUENCE: 276

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```